(12) United States Patent
Lu et al.

(10) Patent No.: US 10,011,571 B2
(45) Date of Patent: Jul. 3, 2018

(54) PREPARATION METHOD FOR AROMATIC HETEROCYCLIC COMPOUND USED AS SELECTIVE JAK3 AND/OR JAK1 KINASE INHIBITOR AND APPLICATION OF AROMATIC HETEROCYCLIC COMPOUND

(71) Applicant: SHENZHEN CHIPSCREEN BIOSCIENCES, LTD., Shenzhen, Guangdong (CN)

(72) Inventors: Xianping Lu, Guangdong (CN); Jindi Yu, Guangdong (CN); Qianjiao Yang, Guangdong (CN); Zhibin Li, Guangdong (CN); Desi Pan, Guangdong (CN); Song Shan, Guangdong (CN); Jiangfei Zhu, Guangdong (CN); Xianghui Wang, Guangdong (CN); Xiangheng Liu, Guangdong (CN); Zhiqiang Ning, Guangdong (CN)

(73) Assignee: SHENZHEN CHIPSCREEN BIOSCIENCES, LTD., Shenzhen (CN)

(*) Notice: Subject to any disclaimer, the term of this patent is extended or adjusted under 35 U.S.C. 154(b) by 0 days.

(21) Appl. No.: 15/510,758

(22) PCT Filed: Sep. 14, 2015

(86) PCT No.: PCT/CN2015/089499
§ 371 (c)(1),
(2) Date: Apr. 11, 2017

(87) PCT Pub. No.: WO2016/041472
PCT Pub. Date: Mar. 24, 2016

(65) Prior Publication Data
US 2017/0253566 A1 Sep. 7, 2017

(30) Foreign Application Priority Data
Sep. 16, 2014 (CN) .......................... 2014 1 0471468

(51) Int. Cl.
*A61K 31/506* (2006.01)
*C07D 239/48* (2006.01)
*C07D 401/12* (2006.01)

(52) U.S. Cl.
CPC ......... *C07D 239/48* (2013.01); *C07D 401/12* (2013.01)

(58) Field of Classification Search
CPC ............................ C07D 239/48; C07D 401/12
See application file for complete search history.

(56) References Cited

U.S. PATENT DOCUMENTS

2010/0249092 A1 9/2010 Singh et al.

FOREIGN PATENT DOCUMENTS

| CN | 101421250 A | 4/2009 |
|---|---|---|
| CN | 102740847 A | 10/2012 |
| CN | 103073508 A | 5/2013 |
| DE | 102009001438 A1 | 9/2010 |
| JP | 2006508997 A | 3/2006 |
| WO | 2004/048343 A1 | 6/2004 |
| WO | 2008049123 A2 | 4/2008 |
| WO | 2008092199 A1 | 8/2008 |

OTHER PUBLICATIONS

J. Luo et al., 36 Cell, 823-837 (2009).*
T. Soussi 60 Cancer Research, 1777-1788 (2000).*
P. Lissoni et al, 7 Cancer Research, 397-401 (2009).*
F. Bunz, Principles of Cancer Genetics 1-47, 1 (2008).*
P.K. Kuppen et al., 115 Histochemistry and Cell Biology, 67-72 (2001).*
D. D'Ambrosio et al., 273 Journal of Immunological Methods 3-13 (2003).*
P.J. Koelink et al., 133 Pharmacology & Therapeutics, 1-18 (2012).*
E. R. Sutherland et al., 350 The New England Journal of Medicine, 2689-2697 (2004).*
S. Judge et al., 111 Pharmacology & Therapeutics, 224-259 (2006).*
V. Brinkmann et al., 9 Nature Reviews | Drug Discovery, 883-897 (2010).*
S.K. Bhatia et al., Autoimmunity and autoimmune disease in 6 Principles of Medical Biology 239-263, 244 (1996).*
S.M. Hayter et al., Autoimmunity Reviews, 754-765, 756 (2012).*
A. Ghigo et al., 32 BioEssays, 185-196 (2010) (see pp. 190-193).*
Z. Wang et al., 19 Drug Discovery Today, 145-150 (2014).*
U.K. Marelli et al., 3 Frontiers in Oncology, 1-12 (2013).*
Kinase Inhibitors Methods and Protocols (B. Kuster ed., 2012).*
R.J. Riese et al., 24 Best Practice & Research Clinical Rheumatology, 513-526 (2010).*
N.K. Williams et al., 387 Journal of Molecular Biology, 219-232 (2009).*
B.H. Kim et al., 7 Molecular Cancer Therapeutics, 2672-2680 (2008).*
S.N. Constantinescu et al., 33 Trends in Biochemical Sciences, 122-131 (2007).*
T. Diaz et al., 6 PLoS One, (2011); E. Derezini et al., 1 Blood Cancer Journal, 1-11 (2011).*
C.L. Sawyers, Nature, 548-552 (2008).*
M. Cetkovic-Cvrlje, 98 Blood, 1607-1613 (2001).*
H-B Park et al., 90 Transplantation, 825-835 (2010).*
R. Stupp et al., 25 Journal of Clinical Oncology, 1637-1638 (2007).*
A.M. Jubb et al., 6, Nature Reviews | Cancer 626-635 (2006).*
U. McDermott et al., 27 Journal of Clinical Oncology, 5650-5659 (2009).*
International Search Report for PCT/CN2015/089499, dated Dec. 1, 2015, ISA/CN.
First Office Action dated Mar. 13, 2018 for Japanese Application No. 2017-533675, 2 pages, English translation provided by https://globaldossier.uspto.gov/#/.
McIver Edward G et al., "Synthesis and structure-activity relationships of a novel series of pyrimidines as potent inhibitors of TBK1/IKKε kinases", Bioorganic & Medicinal Chemistry Letters, vol. 22, No. 23, Sep. 28, 2012, pp. 7169-7173.
Partial European Search Report dated Jan. 30, 2018 for European Application No. 15842179.2, 10 pages.

* cited by examiner

*Primary Examiner* — Alexander R Pagano
(74) *Attorney, Agent, or Firm* — U.S. Fairsky LLP; Yue Xu

(57) ABSTRACT

An application of a compound having general formula (I) as JAK3 and/or JAK1 kinase and a preparation method for the compound.

21 Claims, 1 Drawing Sheet

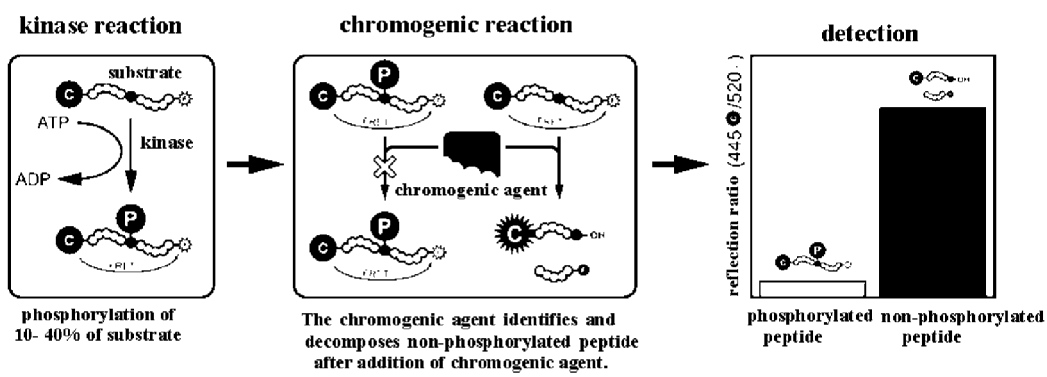

PREPARATION METHOD FOR AROMATIC HETEROCYCLIC COMPOUND USED AS SELECTIVE JAK3 AND/OR JAK1 KINASE INHIBITOR AND APPLICATION OF AROMATIC HETEROCYCLIC COMPOUND

This application is the national phase of International Application No. PCT/CN2015/089499, titled "PREPARATION METHOD FOR AROMATIC HETEROCYCLIC COMPOUND USED AS SELECTIVE JAK3 AND/OR JAK1 KINASE INHIBITOR AND APPLICATION OF AROMATIC HETEROCYCLIC COMPOUND", filed on Sep. 14, 2015, which claims the benefit of priority to Chinese Patent Application No. 201410471468.9 titled "PREPARATION METHOD FOR AROMATIC HETEROCYCLIC COMPOUND USED AS SELECTIVE JAK3 AND/OR JAK1 KINASE INHIBITOR AND APPLICATION OF AROMATIC HETEROCYCLIC COMPOUND", filed with the Chinese State Intellectual Property Office on Sep. 16, 2014, the entire disclosure of which application is incorporated herein by reference.

FIELD

The present invention belongs to the field of medicine, and relates to aromatic heterocyclic compounds having Janus kinase 3 (JAK3) and/or Janus kinase 1 (JAK1) inhibitory activity. The present invention also relates to the preparation method of the compounds, the pharmaceutical composition comprising the compound as an active ingredient, and the pharmaceutical use thereof. The compound of the present invention can be used as the inhibitor of JAK3 and/or JAK1 kinase, and used for the clinical applications, such as the treatment/prevention of diseases related to abnormal activities of these kinases, including autoimmune diseases, inflammatory diseases, cancers and other diseases.

BACKGROUND

In 2002, a total of 518 protein kinase genes in human kinome were identified by Manning et al., in which 218 genes are closely related to the occurrence and development of human diseases (Manning G, et al. 2002, *Science*, 298: 1912-1934). In the drugs obtained up to now, there are as many as 20% of pharmaceuticals using enzymes as the targets, and particularly, the drugs targeting protein kinases are of special value in clinical applications.

Protein kinase is a type of intracellular messenger-dependent enzyme that catalyzes the phosphorylation of particular proteins and implements signaling processes, which mainly includes tyrosine protein kinases (JAKs, Src, Abl, EGFR, FGFR, PDGFR etc.), serine/threonine protein kinases (PKC, MAPK, Rho kinases etc.), bispecific protein kinases (MAPKK) and phosphatidyl inositol kinase (PI3K). The phosphorylation/dephosphorylation process of a protein kinase is able to regulate various biological processes in different cells, such as metabolism, cell differentiation, cell survival, apoptosis, organogenesis, angiogenesis, and immune response etc. (Shchemelinin I., et al. 2006, *Folia Biol.*, 52: 81-100).

JAK kinases (Janus kinases, referred to as JAKs for short, including 4 known members: JAK3, JAK1, TYK2, and JAK2) are a small family in intracytoplasmic non-receptor tyrosine protein kinase superfamily. JAK3 is distributed in marrow and lymphatic system, while JAK1, TYK2, and JAK2 are widely distributed in a plurality of tissue cells. When JAKs bind to a cytokine receptor on the surface of cell, the receptor-coupled JAKs is activated and thereby the receptor is phosphorylated, which provides recruiting response sites, i.e., JAKs phosphorylated STAT proteins, for cytoplasmic signal transducers and activators of transcription, STAT proteins (STAT1~4, STAT5a, STAT5b, and STAT6). After dimerization, the JAKs phosphorylated STAT proteins are transferred to the nucleus and regulate gene expression. This pathway is called JAK/STAT signaling pathway (O'Shea J. J., et al. 2013, *N. Engl. J. Med.*, 368: 161-170).

The JAK/STAT signaling pathway is a signal transduction pathway stimulated by a plurality of cytokines and growth factor receptors. These factors include interleukins (IL-2~7, IL-9, IL-10, IL-15, and IL-21), interferons (IFN-α, IFN-β, and IFN-γ), erythropoietin (EPO), granulocyte-macrophage colony stimulating factor (GM-CSF), growth hormone (GH), prolactin (PRL), thrombopoietin (TPO) etc., which are involved in the proliferation of immune cells and hematopoietic stem cells, and play a key role in immuno-regulatory biological processes (Ghoreschi K., et al. 2009, *Immunol. Rev.*, 228: 273-287). Different subtypes of JAK kinases can be activated by diverse receptors, so as to achieve distinct biological functions.

JAK1 can bind to IL-10, IL-19, IL-20, IL-22, IL-26, IL-28, IFN-α, IFN-γ, IL-6 in gp130 family and other γc-containing receptors (Rodig S J., et al. 1998, *Cell*, 93: 373-383). The knock-off experiment of JAK1 gene in a mouse model has indicated that this enzyme plays a key role in the biological effects of such lots of cytokine receptors described above (Kisseleva T., et al. 2002, *Gene*, 285: 1-24). JAK1 is a novel target for diseases such as immune-related diseases, inflammation and cancers etc. JAK1 inhibitors can be used for the treatment/prevention of diseases, including but not limited to, autoimmune diseases, inflammation and tumors (Hornakova T., et al. 2010, *Blood*, 115:3287-3295), such as leukaemia, lymphomata, melanoma, arthritis, psoriasis, Crohn's disease, lupus erythematosus, acquired immunodeficiency syndrome, Behcet's disease (Hou S., et al. 2013, *Hum. Genet.*, 132:1049-1058), etc.

JAK2 was found to have significant role in the regulation processes of a plurality of receptors, including EPO, GH, PRL, IL-3, IFN-γ etc. (Kisseleva T., et al. 2002, *Gene*, 285: 1-24; Levy D. E., et al. 2002, *Nat. Rev. Mol. Cell Biol.*, 3: 651-662; O'Shea J. J., et al. 2002, *Cell*, 109 (suppl.): S121-S131). In a mouse model, JAK2 gene knock-off may result in death of anemic animals (Schindler C. et al. 2007, *J. Biol. Chem.*, 282: 20059-20063); While in human, a base mutation JAK2V617F in JAK2 gene is closely related to the occurrence of myeloproliferative diseases, including polycythemia vera (PV), essential thrombocythemia (ET), idiopathic myelofibrosis (IMF), and chronic myelogenous leukemia (CIVIL) etc. (Ghoreschi K., et al. 2009, *Immunol. Rev.*, 228: 273-287). Thus, JAK2 has become an exact target for the treatment/prevention of such diseases.

JAK3 regulates cell signaling via binding to the gamma common chain (γc) in the cytokine-receptor complexes, such as IL-2, IL-4, IL-7, IL-9, IL-15, and IL-21. Mutation in either JAK3 or γc may lead to severe combined immunodeficiency (SCID) (Villa A., et al. 1996, *Blood*, 88: 817-823). Abnormal activity of JAK3 is represented as significant reduction of T-cells and NK cells, and loss of functions of B-cells, which has a strong impact on the normal biological functions of immune system etc. Based on its functional characteristics and special tissue distribution, JAK3 has become a promising pharmaceutical target for immune system-related diseases, and thus its inhibitors will have great clinical value in the treatment/prevention of rheumatoid arthritis (RA), Crohn's disease, systemic lupus erythematosus, multiple sclerosis, type I diabetes, psoriasis, allergic diseases, asthma, chronic obstructive pulmonary disease, leukaemia, lymphoma, organ transplant and other diseases (Papageorgiou A. C., et al. 2004, *Trends Pharm. Sci.*, 2004, 25: 558-562).

TYK2 is the first member in JAK family, and it can be activated by a plurality of receptors, such as interferons (IFNs), IL-10, IL-6, IL-12, IL-23, and IL-27. In mice, the loss of function of TYK2 may lead to deficiency in the signaling pathways of many cytokine receptors, which may further result in virus infection, and decrease antibacterial immune function, and thus increase the possibility of infection in lung (Kisseleva T., et al. 2002, *Gene*, 285: 1-24). In addition, the research in the group of Lamer A. C. has demonstrated that TYK2 is helpful to suppress the growth and metastasis of breast cancer (Zhang Q., et al. 2011, *J. Interferon Cytokine Res.*, 31:671-677); recently, this group has also reported that TYK2 facilitates obesity regulation by the differentiation of brown adipose tissue (BAT) in mice and human, so that it may protect organisms from obesity, or even reverse it (Derecka M., et al., 2012, *Cell Metab.*, 16:814-824). This might provide a new opportunity for fat patients suffering from cancers.

In November 2012, pan-JAKs inhibitor Xeljanz (Tofacitinib) from Pfizer was approved by FDA for the treatment of RA. In October 2013, the phase III clinical data of Xeljanz for the treatment of psoriasis were disclosed by the company. Compared to the double-blind test of Enbrel (Etanercept), this drug satisfied the requirements for a non-inferiority trial. However, Xeljanz possesses some side-effects, for example, it may result in reduced amount of erythrocytes and leucocytes, and increased cholesterol level. This might be related to its high JAK2 inhibitory activity and low selectivity (Zak M., et al. 2012, *J. Med. Chem.*, 55: 6176-6193). Therefore, it is highly demanded for the research and discovery of selective JAK inhibitors.

There are several selective JAK inhibitors in different clinical phases used for the treatment of immune system-related diseases, such as RA, Crohn's disease, psoriasis, and myelofibrosis, including selective JAK3 inhibitor VX-509, selective JAK1 inhibitor GLPG0634 (Feist E., et al. 2013, *Rheumatology*, 52:1352-1357) and INCB39110 (http://www.incyte.com/research/pipeline) etc. Besides, some patents have been disclosed for the selective inhibitors with different structure types: 1) selective JAK3 inhibitors, such as pyrrolo[1,2-b]pyridazine (WO2012125887), pyrazolo[3,4-d]pyrimidine (WO2011048082, WO2011134861, WO2012022681), diaminopyrimidines (WO2011029807, WO2012015972), pyrrolo[2,3-b]pyridine (JP2012012332), diamino-pyridinyl-3-formamide (WO2010061971, US20120108566), pyrrolo[2,3-b]pyrazine (WO2011144584, WO2011144585); 2) selective JAK1 inhibitors, such as tricyclic compounds (WO2011086053), substituted pyrazoles and pyrroles (WO2010135650, WO2011112662), anilinophthalazines (WO2012037132). Additionally, patents have also been disclosed for the selective JAK2 inhibitors and selective TYK2 inhibitors, and the inhibitors with both two subtypes (JAK3/1, JAK1/2), which will not be further described herein.

Inducible T-cell kinase (ITK), also referred to as Emt or Tsk, is one of the non-receptor tyrosine kinases in Tec family. ITK is expressed in T-cells, NKT cells and mast cells. This kinase plays a key role in the signaling pathway regulation of T-cell receptor (TCR), CD28, CD2, chemokine receptor CXCR4 and FcεR etc. Secretion of Th2-type cytokines (including IL-4, IL-5, and IL-13 etc.) plays an important part in the regulation of immune inflammation. ITK deficiency has impact on Th2 cell response, and thereby alleviates chronic or late inflammatory reaction (Sahu N., et al. 2009, *Curr. Top. Med. Chem.*, 9: 690-703; Lin T. A., et al. 2004, *Biochemistry*, 43: 11056-11062). B-cell lymphocyte kinase (BLK) is one of the non-receptor tyrosine kinases in Src family, which is expressed in B lymphocytes, and relates to the growth and differentiation of B lymphocytes. Tight binding between BLK kinase, or phosphatase and corresponding co-receptors has important effect on the signaling pathway regulation of B-cell receptor (BCR), for example, such kinase may influence the apoptosis and formation retardation of BCR (Texido G, et al. 2000, *Mol. Cell Biol.*, 20: 1227-1233). BLK has also important influence on pre-B-cell receptor-mediated NF-κB activation (Saijo K., et al. 2003, *Nat. Immunol.*, 4: 274-279). Recent researches have demonstrated that BLK is related to the pathogenesis of RA, systemic lupus erythematosus and many other autoimmune diseases (Simpfendorfer K R., et al. 2012, *Hum. Mol. Genet.*, 21: 3918-3925; Génin E., et al. 2013, *PLoS One*, 8: e61044).

TANK-binding kinase1 (TBK1), also referred to as NAK (NF-κB activating kinase) or T2K, is a kind of Ser/Thr protein kinase in IKK family. TBK1 is widely expressed in the stomach, colon, lung, thymus and liver of mouse; and also expressed in the lymphoid and nonlymphoid organs of human, including spleen, brain and kidney etc. This kinase has influence on the regulation of immune response to bacteria and virus, and expression of inflammation-related factors, such as IL-6, TNF-α and IFN-β, etc. In the insulin signaling pathway, TBK1 can mediate the phosphorylation of Ser994 in the insulin receptor and the lipid metabolism. These results have indicated that TBK1 plays an important role in various immunobiological and immunopathological mechanisms (Yu T., et al. 2012, *Mediators Inflamm.*, 2012: 979105-979112; Hammaker D., et al. 2012, *Rheumatology*, 51: 610-618).

Vascular endothelial growth factor receptor (VEGFR) family including 3 members, i.e., VEGFR-1 (Flt1), VEGFR-2 (KDR/Flk1) and VEGFR-3 (Flt4), consists of 7 extracellular regions with immunoglobulin-like structure, a membrane region and a tyrosine kinase region, in which the tyrosine kinase activity is activated via binding between the receptor and the ligand, such as VEGFs A-F and placenta growth factor, further inducing various biological effects in cells, such as important effects on the growth and differentiation of cell (Shibuya M., et al. 2010, *Genes Cancer*, 1: 1119-1123). Other researches have demonstrated that VEGFR1 is expressed in endotheliocytes, monocytes and macrophages of a RA patient. VEGFA can activate VEGFR1, and result in the proliferation of endotheliocyte and angiopoiesis. VEGFA protein is highly expressed in synovia, lymph, serum and synovial tissue of a RA patient, and the level of VEGFA is positively correlated with RA. VEGFR2 is expressed in the synovial tissue of a RA patient. VEGF A, C, and D can activate VEGFR2 signaling, and enhance the vascular permeability and angiopoiesis. VEGFC can be detected in various types of cells in RA thickened synovial inner layer, especially in perivascular cells and smooth muscle cells. VEGFR3 can be expressed in monocytes, macrophages, some dendritic cells, capillary vessels of normal mammary tissue and neuroendocrine organs. It has been found in some researches that VEGFR3 contributes to the occurrence of autoimmune diseases, such as RA, inflammatory bowel disease, ulcer diseases and Crohn's disease etc., and lymphoangiogenesis-related tumors. However, relevant mechanism has not been completely understood (D'Aura Swanson C, et al. 2009, *Nat. Rev. Rheumatol.*, 5: 317-324; Aoki Y, et al. 2005, *J. Natl. Cancer Inst.*, 97: 2-3).

The protein kinase inhibitors disclosed herein can be used for the treatment and/or prevention of immune system-related diseases, including but not limited to, RA, psoriasis, Crohn's disease, systemic lupus erythematosus, multiple sclerosis, type I diabetes, allergic diseases, chronic obstructive lung disease, asthma, leukaemia, and lymphoma, etc. At the same time, these compounds or a pharmaceutical composition comprising the compounds as the active ingredients will have maximal clinical efficacy for these diseases in the safe therapeutic window.

SUMMARY

One aspect of the invention is directed to aromatic heterocyclic compounds having JAK3 and/or JAK1 inhibitory activity, including their derivatives, such as a pharmaceutically acceptable salt, hydrate, stereoisomer, and pro-drug thereof.

Another aspect of the invention relates to a preparation method of the compound described herein.

Yet another aspect of the invention relates to a pharmaceutical composition comprising the compound of the invention as the active ingredient, and clinical use of the compound or the pharmaceutical composition of the invention in the treatment/prevention of the diseases related to abnormal activities of kinases, such as JAKs, and use of the compound or the pharmaceutical composition of the invention in the preparation of a medicament used for the treatment/prevention of the diseases related to abnormal activities of kinases, such as JAKs.

The present invention provides a compound of general formula (I), including a pro-drug, stereoisomer, pharmaceutically acceptable salt or hydrate thereof.

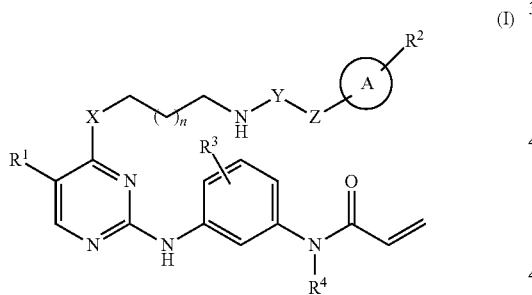

(I)

wherein,
$R^1$ is halogen or C1-C6 alkyl;
$R^2$ is one or more substituents selected from the group consisting of hydrogen, hydroxy, cyano, halo, C1-C6 alkyl, C1-C6 alkoxy, C1-C6 haloalkyl, C1-C6 alkylcarbonyl and C1-C6 alkyl amino;
$R^3$ is hydrogen or halogen;
$R^4$ is hydrogen or C1-C4 alkyl;
X is NH, O or S;
Y is CO or $S(O)_2$;
Z is a covalent bond, $CH_2$ or $(CH_2)_2$;
n is an integer from 1 to 4; and
Ring A is a benzene ring, pyridine ring or piperidine ring.

In one preferable aspect, the present invention provides a compound of general formula (I), including a pro-drug, stereoisomer, pharmaceutically acceptable salt or hydrate thereof, wherein,
$R^1$ is halogen or C1-C6 alkyl;
$R^2$ is one or more substituents selected from the group consisting of hydrogen, hydroxy, cyano, fluoro, methyl, ethyl, methoxyl, difluoromethyl, trifluoromethyl, acetyl and dimethylamino;
$R^3$ is hydrogen or halogen;
$R^4$ is hydrogen or methyl;
X is NH or O;
Y is CO or $S(O)_2$;
Z is a covalent bond, $CH_2$ or $(CH_2)_2$;
n is an integer from 1 to 4; and
Ring A is a benzene ring, pyridine ring or piperidine ring.

In one more preferable aspect, the present invention relates to a compound of general formula (I), including a pro-drug, stereoisomer, pharmaceutically acceptable salt or hydrate thereof, wherein,
$R^1$ is halogen or C1-C6 alkyl;
$R^2$ is one or more substituents selected from the group consisting of hydrogen, hydroxy, cyano, fluoro, methyl, ethyl, methoxyl, difluoromethyl, trifluoromethyl, acetyl and dimethylamino;
$R^3$ is hydrogen or fluoro;
$R^4$ is methyl;
X is NH;
Y is CO;
Z is a covalent bond;
n is an integer from 1 to 4; and
Ring A is a benzene ring, pyridine ring.

In one more preferable aspect, the present invention relates to a compound of general formula (I), including a pro-drug, stereoisomer, pharmaceutically acceptable salt or hydrate thereof, wherein,
$R^1$ is chloro, fluoro or methyl;
$R^2$ is one or more substituents selected from the group consisting of hydrogen, hydroxy, cyano, fluoro, methyl, ethyl, methoxyl, difluoromethyl, trifluoromethyl, acetyl and dimethylamino;
$R^3$ is hydrogen or fluoro;
$R^4$ is methyl;
X is NH;
Y is CO;
Z is a covalent bond;
n is an integer from 1 to 4; and
Ring A is a benzene ring.

In one more preferable aspect, the present invention relates to a compound of general formula (I), including a pro-drug, stereoisomer, pharmaceutically acceptable salt or hydrate thereof, wherein,
$R^1$ is chloro;
$R^2$ is one or more substituents selected from the group consisting of hydrogen, hydroxy, cyano, fluoro, methyl, ethyl, methoxyl, difluoromethyl, trifluoromethyl, acetyl and dimethylamino;
$R^3$ is hydrogen or fluoro;
$R^4$ is methyl;
X is NH;
Y is CO;
Z is a covalent bond;
n is an integer from 1 to 4; and
Ring A is a benzene ring.

In one particularly preferable aspect, the present invention relates to a compound of general formula (I), including a pro-drug, stereoisomer, pharmaceutically acceptable salt or hydrate thereof, wherein,
$R^1$ is chloro;
$R^2$ is one or more substituents selected from the group consisting of cyano, fluoro and trifluoromethyl;
$R^3$ is hydrogen or fluoro;
$R^4$ is methyl;
X is NH;
Y is CO;
Z is a covalent bond;
n=1;
Ring A is a benzene ring.

In one particularly preferable aspect, the present invention relates to a compound of general formula (I), including a pro-drug, stereoisomer, pharmaceutically acceptable salt or hydrate thereof, wherein, $R^1$ is chloro;
$R^2$ is one or more substituents selected from the group consisting of cyano;
$R^3$ is hydrogen or fluoro;
$R^4$ is methyl;
X is NH;
Y is CO;
Z is a covalent bond;
n=1; and
Ring A is a benzene ring.

BRIEF DESCRIPTION OF THE DRAWINGS

FIG. 1 is a schematic diagram showing the principle of Z'-LYTE kinase activity assay, which reflects the steps involved in the test, including the reaction between the kinase and its substrate, the chromogenic reaction and the detection.

DETAILED DESCRIPTION OF EMBODIMENTS

The "Halogen" described herein refers to fluorine, chlorine, bromine, or iodine, and particularly to fluorine, chlorine or bromine.

The "alkyl" described herein includes linear, branched or cyclic alkyl. Preferably, the alkyl is C1-C8 alkyl, or C1-C6 alkyl; and particularly preferably, the alkyl is C1-C4 alkyl; and more particularly preferably, the alkyl is methyl, ethyl, propyl or isopropyl, n-butyl, isobutyl or t-butyl. The alkyl in the compound of the present invention can be optionally substituted or unsubstituted, and the substituent may include alkyl, halogen, alkoxy, hydrocarbyl, and hydroxyl, etc. Examples of the alkyl of the present invention include methyl, ethyl, n-propyl, isopropyl, n-butyl, isobutyl, t-butyl, n-pentyl, isopentyl, n-hexyl, isohexyl, cyclopropyl, cyclobutyl, cyclopentyl, and cyclohexyl, etc.

The "alkoxy" described herein refers to the group formed by attaching the above alkyl to an oxygen atom, in which the oxygen atom is able to form a bond freely, such as methoxyl, ethoxy, propoxy, butoxy, pentoxy, isopropoxy, t-butoxy, cyclopropoxy, and cyclohexyloxy, etc.

The "alkylcarbonyl" described herein refers to the group formed by attaching the above alkyl to a carbonyl, such as acetyl, propionyl, isopropionyl, butyryl, t-butyryl, cyclopropionyl, and cyclohexanoyl, etc.

The "alkylamino" described herein refers to the group formed by attaching the above alkyl to an amino group, such as methylamino, ethylamino, and 4-dimethylamino, etc.

The term "pharmaceutical" or "pharmaceutically acceptable" described herein can be understood as suitable for the use in human and animals in a reasonable scope of medicine, and tolerable with no unacceptable side-effects, including toxicity, allergy, stimulation, complications and so on.

The present invention relates to a pharmaceutical composition, which comprises the compound of formula (I) mentioned above, including a pro-drug, stereoisomer, pharmaceutically acceptable salt or hydrate thereof, as the active ingredient, and a pharmaceutically acceptable carrier, adjuvant or excipient, etc. The pharmaceutically acceptable carrier, adjuvant or excipient refers to any diluent, auxiliary and carrier that can be used in the pharmaceutical field, such as, but not limit to, the materials listed in "Handbook of Pharmaceutical Excipients", $8^{th}$ ed, 2013.

The compound described in the present invention can be optionally used in combination with one or more active ingredients, in which the dosage of each component and the ratio of them can be determined by a person skilled in the art based on specific disorder, specific condition of the patient and clinical requirements.

The compound or pharmaceutical composition described in the present invention can be prepared into any dosage forms, which comprise common excipient in the pharmaceutical field, such as, but not limited to, oral formulation (tablet, capsule, powder, granule, syrup, pill etc.), injection, topical formulation etc. The formulation of the present invention usually contains 0.5-70% of active ingredient by weight, and preferably, 1-20% of active ingredient by weight.

The compound of formula (I) described herein can be administrated to mammals (including human) by oral or injection route in clinical practice, and preferably, by oral route. The dosage is 0.0001-200 mg/kg body weight per day, and more preferably, 0.01-100 mg/kg body weight per day, and the most preferably, 0.1-50 mg/kg body weight per day. At the same time, the best dosage is determined based on individual's condition, usually beginning at a lower dosage, and gradually increasing to a higher dosage.

In the examples and preparative examples of the present invention, the compounds described herein and the preparation methods thereof are further described and illustrated. It should be understood that the preparative examples and examples below will not by any means limit the scope of the invention.

The preparation method of the derivative of formula (I) of the invention will be described in the following synthetic route. The raw materials, reagents, catalysts, and solvents etc. used in the schematic synthetic route can be prepared by the methods well-known to a person skilled in the organic chemistry or can be commercially available. All final derivatives of the invention can be prepared by the methods described in the schematic diagram or other similar methods. These methods are well-known to a person skilled in the organic chemistry. All variable factors used in these schematic diagrams are defined as follows or according to the claims.

Preparation Method:

(a) Intermediate III(a) can be purchased directly or prepared according to the following illustrative synthetic method:

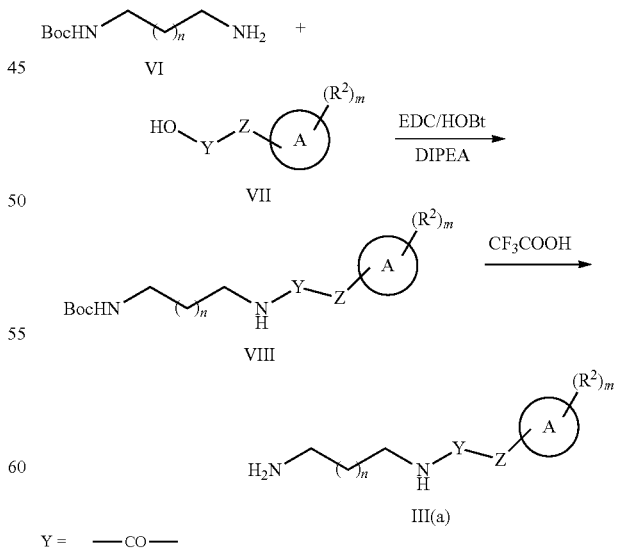

Compound VIII is obtained by condensation between unilaterally protected diamine VI and compound VII. In the condensation reaction, a peptide condensing agent is used as the catalyst, such as 1-ethyl-3-(3-dimethylaminopropyl)carbodiimide (EDC), N,N'-dicyclohexylcarbodiimide (DCC), and N,N'-carbonyldiimidazole (CDI) etc. The reaction is carried out at temperature ranging from 0-60° C. for 2-72 h. The solvent used in the reaction is a common solvent, such as benzene, toluene, tetrahydrofuran, dioxane, dichloromethane, chloroform, N,N'-dimethylformamide etc. Alkali, such as sodium hydroxide, triethylamine or pyridine, etc., can be added, if necessary.

Compound III(a) is obtained after removal of Boc from the resultant compound VIII under the action of acid (preferably, trifluoroacetic acid). The reaction is carried out at a temperature ranging from 0-60° C. for 0.5-2 h. The solvent used in the reaction is dichloromethane, tetrahydrofuran, N,N'-dimethyl formamide, etc.

(b) Intermediate III(b) can be purchased directly or prepared according to the following illustrative synthetic method:

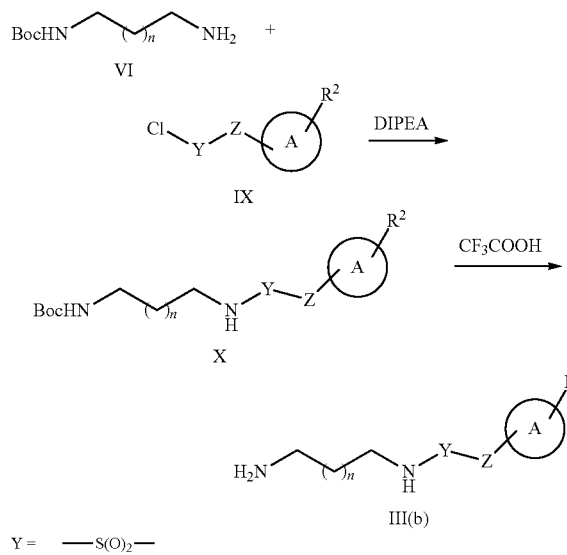

Y = —S(O)$_2$—

Compound X is obtained by condensation between unilaterally protected diamine VI and compound VX. The reaction is carried out at a temperature ranging from 0-60° C. for 0.5-2 h. The solvent used in the reaction is a common solvent, such as benzene, toluene, tetrahydrofuran, dioxane, dichloromethane, chloroform, N,N'-dimethylformamide etc. Triethylamine, diisopropylethylamine, or pyridine is commonly used as the acid-binding agent; optionally, inorganic base, such as NaOH, Na$_2$CO$_3$, NaOAc, etc., can be added.

Compound III(b) is obtained after removal of Boc from the resultant compound X under the action of an acid (preferably, trifluoroacetic acid). The reaction is carried out at a temperature ranging from 0-60° C. for 0.5-2 h. Common solvent used in the reaction is dichloromethane, tetrahydrofuran, N,N'-dimethylformamide, and water, etc. The acid used can be trifluoroacetic acid, hydrochloric acid etc.

(C) Intermediate V can be prepared by the following illustrative synthetic method below:

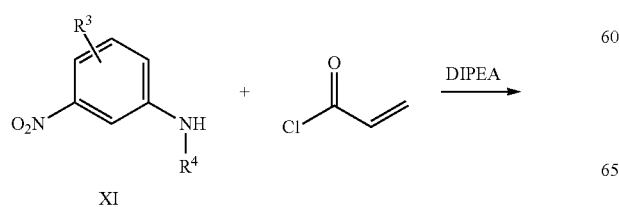

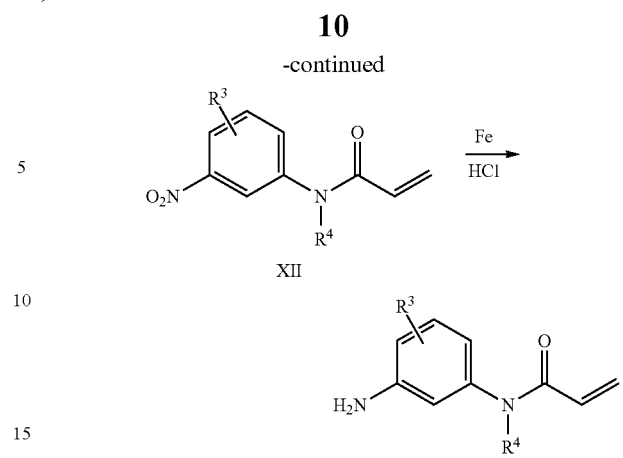

Compound XII is obtained by condensation between Compound XI (commercially available or prepared) and acryloyl chloride in the presence of an alkali (preferably, diisopropylethylamine). The nitro group in the resultant compound XII is then reduced by iron powder to give the target intermediate V. The alkali used can be diisopropylethylamine, or triethylamine, etc.

(D) The compound of formula (I) described herein can be prepared by the following illustrative synthetic method below:

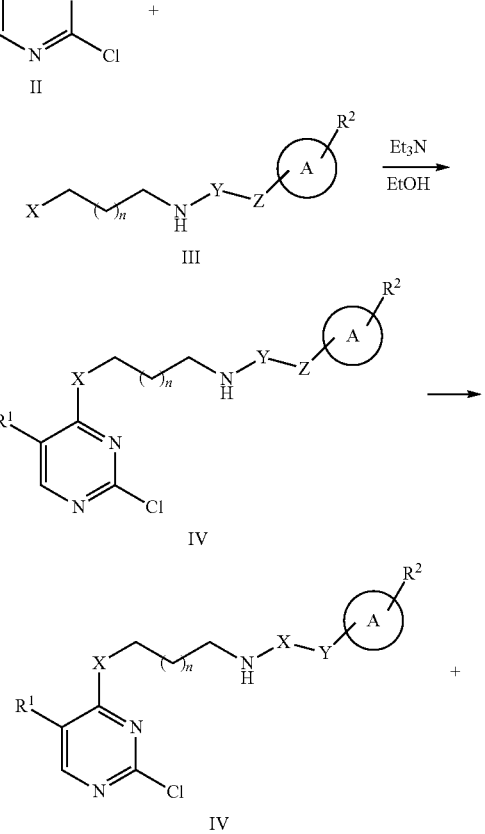

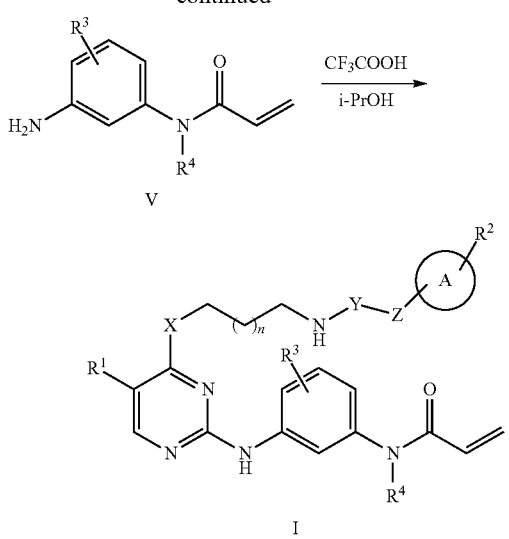

Compound IV is obtained by substitution reaction of compound II and compound III in the presence of triethylamine, in which both compounds II and III can be purchased directly. The reaction temperature is reflux for 8-16 h. The solvent used in the reaction is ethanol, methanol, or n-butanol, etc. The alkali used is triethylamine, or diisopropylethylamine, etc.

Compound I is obtained by substitution reaction of compound IV and the resultant compound V catalyzed by an acid (preferably, trifluoroacetic acid). The reaction temperature is reflux with a duration of 8-16 h. The solvent used in the reaction is isopropanol, or n-butanol, etc.; and the acid used in the reaction is trifluoroacetic acid, or hydrochloric acid etc.

The compound of formula I can be purified by common separation methods, such as extraction, recrystallization, or column chromatography, etc.

The representative compounds described in the present invention are listed in Table 1. The number of compound is consistent with the "number of example" in the Section of Examples, i.e., the synthesis of compound 1 in Table 1 is described in "Example 1", and the synthesis of compound 30 in Table 1 is described in "Example 30".

TABLE 1

Representative compounds of the invention

| Example | Structural formula | Chemical name |
|---|---|---|
| 7 | | N-(3-(5-chloro-2-(4-fluoro-3-(N-methylacrylamido)phenylamino)pyrimidinyl-4-amino)propyl)-4-cyanobenzamide |
| 13 | | N-(3-(2-(3-acrylamido-4-fluoro-phenylamino)-5-chloropyrimidinyl-4-amino)propyl)-4-trifluoromethyl-benzamide |
| 17 | | N-(3-(2-(3-acrylamido-4-fluoro-phenylamino)-5-chloropyrimidinyl-4-amino)propyl)-4-fluorobenzamide |
| 19 | | 4-fluoro-N-(3-(2-(4-fluoro-3-(N-methylacrylamido)phenylamino)-5-methylpyrimidinyl-4-amino)propyl)benzamide |

TABLE 1-continued

Representative compounds of the invention

| Example | Structural formula | Chemical name |
|---|---|---|
| 21 | | N-(3-(2-(4-fluoro-3-(N-methyl-acrylamido)phenylamino)-5-methyl-pyrimidinyl-4-amino)propyl)-4-trifluoromethylbenzamide |
| 22 | | N-(3-(5-chloro-2-(4-fluoro-3-(N-methylacrylamido)phenylamino)pyrimidinyl-4-amino)propyl)-4-trifluoromethylbenzamide |
| 23 | | N-(3-(5-chloro-2-(4-fluoro-3-(N-methylacrylamido)phenylamino)pyrimidinyl-4-amino)propyl)-4-fluorobenzamide |
| 27 | | N-(3-(5-chloro-2-(4-fluoro-3-(N-methylacrylamido)phenylamino)pyrimidinyl-4-amino)propyl)-N-methylpiperidinyl-4-formamide |
| 28 | | N-(3-(2-(3-acrylamido-4-fluoro-phenylamino)-5-chloropyrimidinyl-4-amino)propyl)-4-cyanobenzamide |

TABLE 1-continued

Representative compounds of the invention

| Example | Structural formula | Chemical name |
|---|---|---|
| 32 | | N-(3-(5-chloro-2-(4-fluoro-3-(N-methylacrylamido)phenylamino)pyrimidinyl-4-amino)propyl)-4-N,N-dimethylaminobenzamide |
| 36 | | N-(3-(5-chloro-2-(4-fluoro-3-(N-methylacrylamido)phenylamino)pyrimidinyl-4-amino)propyl)-2,4,6-trifluorobenzamide |
| 40 | | N-(3-(5-chloro-2-(4-fluoro-3-(N-methylacrylamido)phenylamino)pyrimidinyl-4-amino)propyl)-4-methoxylbenzamide |
| 44 | | N-(3-(5-chloro-2-(4-fluoro-3-(N-methylacrylamido)phenylamino)pyrimidinyl-4-amino)propyl)-6-cyanonicotinamide |
| 48 | | N-(3-(5-chloro-2-(4-fluoro-3-(N-methylacrylamido)phenylamino)pyrimidinyl-4-amino)propyl)-4-hydroxybenzamide |

TABLE 1-continued

Representative compounds of the invention

| Example | Structural formula | Chemical name |
|---|---|---|
| 52 | 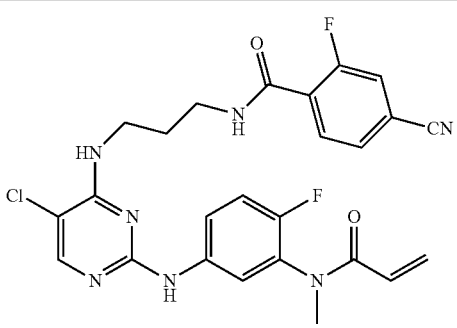 [SMILES: C=CC(=O)N(C)c1cc(Nc2ncc(Cl)c(NCCCNC(=O)c3ccc(C#N)cc3F)n2)ccc1F] | N-(3-(5-chloro-2-(4-fluoro-3-(N-methylacrylamido)phenylamino)pyrimidinyl-4-amino)propyl)-4-cyano-2-fluorobenzamide |
| 56 | 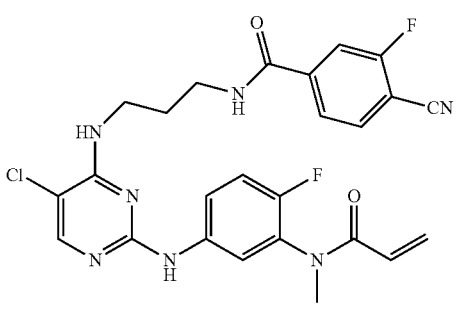 [SMILES: C=CC(=O)N(C)c1cc(Nc2ncc(Cl)c(NCCCNC(=O)c3ccc(C#N)c(F)c3)n2)ccc1F] | N-(3-(5-chloro-2-(4-fluoro-3-(N-methylacrylamido)phenylamino)pyrimidinyl-4-amino)propyl)-4-cyano-3-fluorobenzamide |
| 58 | 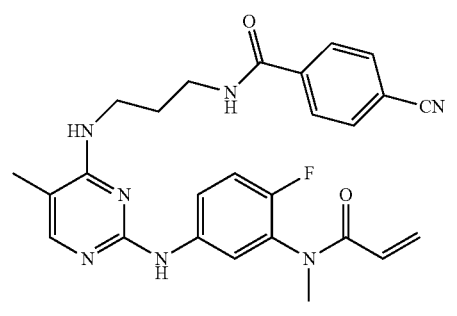 [SMILES: C=CC(=O)N(C)c1cc(Nc2ncc(C)c(NCCCNC(=O)c3ccc(C#N)cc3)n2)ccc1F] | 4-cyano-N-(3-(2-(4-fluoro-3-(N-methylacrylamido)phenylamino)-5-methylpyrimidinyl-4-amino)propyl)benzamide |
| 60 | 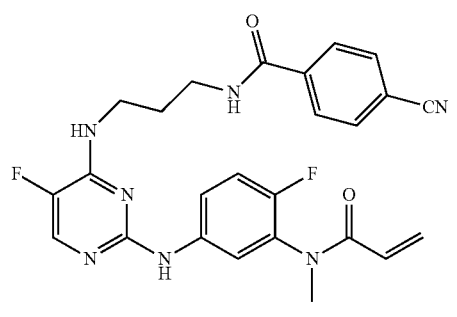 [SMILES: C=CC(=O)N(C)c1cc(Nc2ncc(F)c(NCCCNC(=O)c3ccc(C#N)cc3)n2)ccc1F] | 4-cyano-N-(3-5-fluoro-2-(4-fluoro-3-(N-methylacrylamido)phenylamino)pyrimidinyl-4-amino)propyl)benzamide |

TABLE 1-continued

Representative compounds of the invention

| Example | Structural formula | Chemical name |
|---|---|---|
| 64 | | N-(5-(5-chloro-4-(3-(2-(4-cyano-phenyl)acetamino)propylamino)pyrimidinyl-2-amino)-2-fluorophenyl)-N-methylacrylamide |
| 68 | | N-(5-(5-chloro-4-(3-(4-cyanophenyl-sulfonamino)propylamino)pyrimidinyl-2-amino)-2-fluorophenyl)-N-methylacryloyl |
| 71 | | N-(3-(5-chloro-2-(4-fluoro-3-(N-methylacrylamido)phenylamino)pyrimidinyl-4-oxo)propyl)-4-cyano-benzamide |
| 75 | | N-(3-(5-chloro-2-(4-fluoro-3-(N-methylacrylamido)phenylamino)pyrimidinyl-4-amino)propyl)-isonicotinamide |
| 79 | | N-(3-(5-chloro-2-(4-fluoro-3-(N-methylacrylamido)phenylamino)pyrimidinyl-4-amino)propyl)-4-ethylbenzamide |

TABLE 1-continued

Representative compounds of the invention

| Example | Structural formula | Chemical name |
|---|---|---|
| 83 | | N-(3-(5-chloro-2-(4-fluoro-3-(N-methylacrylamido)phenylamino)pyrimidinyl-4-amino)propyl)-4-methylbenzamide |
| 87 | | N-(3-(5-chloro-2-(4-fluoro-3-(N-methylacrylamido)phenylamino)pyrimidinyl-4-amino)propyl)benzamide |
| 91 | | N-(3-(5-chloro-2-(4-fluoro-3-(N-methylacrylamido)phenylamino)pyrimidinyl-4-amino)propyl)-3-trifluoromethylbenzamide |
| 95 | | N-(3-(5-chloro-2-(4-fluoro-3-(N-methylacrylamido)phenylamino)pyrimidinyl-4-amino)propyl)-3-cyanobenzamide |
| 103 | | N-(3-(5-chloro-2-(4-fluoro-3-(N-methylacrylamido)phenylamino)pyrimidinyl-4-amino)propyl)-3-fluoro-4-trifluoromethylbenzamide |

TABLE 1-continued

Representative compounds of the invention

| Example | Structural formula | Chemical name |
|---|---|---|
| 107 | | N-(3-(5-chloro-2-(4-fluoro-3-(N-methylacrylamido)phenylamino)pyrimidinyl-4-amino)propyl)-2,3,4,5-tetrafluorobenzamide |
| 111 | | 4-acetyl-N-(3-(5-chloro-2-(4-fluoro-3-(N-methylacrylamido)phenylamino)pyrimidinyl-4-amino)propyl)benzamide |
| 115 | | N-(3-(5-chloro-2-(4-fluoro-3-(N-methylacrylamido)phenylamino)pyrimidinyl-4-amino)propyl)-4-difluoromethylbenzamide |
| 123 | | N-(6-(5-chloro-2-(4-fluoro-3-(N-methylacrylamido)phenylamino)pyrimidinyl-4-amino)hexyl)-4-cyanobenzamide |

The present invention will be further described by reference to the Examples below. However, the scope of the invention is not limited to these examples. The percentage described herein refers to the weight percentage, unless otherwise indicated. All numerical ranges, such as measurement units, reaction conditions, and the physical states or percentages of compounds, described in the specification are provided for clear reference. Expected results can also be achieved by the skilled person in the art when the patent is practiced with temperatures, concentrations, quantities, and number of carbon atoms and the like outside the range or different from individual values.

Example 1

Preparation of 2-fluoro-N-methyl-5-nitroaniline

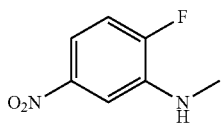

Yellow solid of 2-fluoro-N-methyl-5-nitroaniline (19.0 g, yield of 87.0%) was prepared as follows. 2-fluoro-5-nitroaniline (20.0 g, 128.2 mmol) and paraformaldehyde (16.0 g, 533.3 mmol) were dissolved in 500 ml methanol and stirred at room temperature. Subsequently, 100 ml sodium methoxide (3.4 g, 63 mmol) solution in methanol was added dropwise. After stirred at room temperature for 16 hours, the reaction solution was divided into two equal parts, to which NaBH₄ (9.7 g, 255.2 mmol) was added. The mixture was stirred for 15 min. The reaction was monitored by LC-MS. After the reaction, the mixture was poured into 1 M KOH aqueous solution, and stirred to precipitate the solid. The target intermediate was obtained by filtration. LC-MS (m/z) 171 (M+1).

Example 2

Preparation of N-(2-fluoro-5-nitrophenyl)-N-methylacrylamide

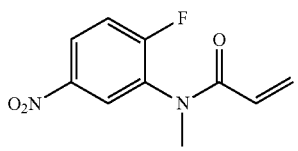

Yellow oil of N-(2-fluoro-5-nitrophenyl)-N-methylacrylamide (12.0 g, yield of 83.0%) was prepared as follows. 2-fluoro-N-methyl-5-nitroaniline (11.0 g, 64.7 mmol) and DIPEA (23 ml, 129.4 mmol) were dissolved in 100 ml THF, and stirred at room temperature. Subsequently, acryloyl chloride (11 ml, 129.4 mmol) was added dropwise. After stirred at room temperature for 1 h, most of the reaction solvent was removed by evaporation. The solution was then diluted by adding 100 ml ethyl acetate, washed by saturated saline solution, dried, filtered and concentrated under reduced pressure to give the target intermediate. LC-MS (m/z) 225 (M+1).

Example 3

Preparation of N-(5-amino-2-fluorophenyl)-N-methylacrylamide

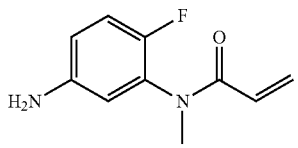 [SMILES: C=CC(=O)N(C)c1cc([N+](=O)[O-])ccc1F]

Brown oil of N-(5-amino-2-fluorophenyl)-N-methylacrylamide (5.6 g, yield of 54.0%) was prepared as follows. Iron powder (20.0 g, 357 mmol) and NH₄Cl (20.0 g, 374 mmol) were dissolved in 200 ml water, heated to 80° C., and stirred for 0.5 h. Subsequently, 20 ml solution of N-(2-fluoro-5-nitrophenyl)-N-methylacrylamide (12.0 g, 53.6 mmol) in ethyl acetate was added. After stirred at 80° C. for 1 h, the reaction solution was adjusted to alkaline pH by NaHCO₃ aqueous solution. The iron mud was filtered, and the filtrate was extracted with ethyl acetate. The organic phases were combined and concentrated at reduced pressure to give the target intermediate. LC-MS (m/z) 195 (M+1).

Example 4

Preparation of t-butyl ester of N-(4-cyano-benzamino)propylaminoformic acid

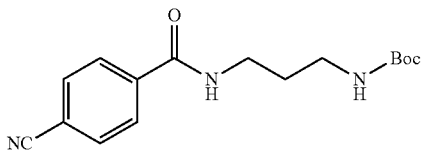 [SMILES: CC(C)(C)OC(=O)NCCCNC(=O)c1ccc(C#N)cc1]

White solid of t-butyl ester of N-(4-cyano-benzamino)propylaminoformic acid (850 mg, yield of 98.0%) was prepared as follows. The t-butyl ester of 3-aminopropylaminoformic acid (500 mg, 2.87 mmol) was dissolved in 20 ml THF, to which 1-ethyl-3-(3-dimethylaminopropyl)carbodiimide hydrochloride (1.0 g, 5.24 mmol), 1-hydroxybenztriazole (580 mg, 4.30 mmol), DIPEA (1 ml, 5.63 mmol) and 4-cyanobenzoic acid (425 mg, 2.89 mmol) were added. The mixture was stirred at room temperature for 20 h. Subsequently, the pH value of the mixture was adjusted to 8-10 by NaHCO₃ aqueous solution. The mixture was then extracted with ethyl acetate. The organic phases were combined and concentrated at reduced pressure to give the target intermediate. LC-MS (m/z) 304 (M+1).

Example 5

Preparation of N-(3-aminopropyl)-4-cyano-benzamide

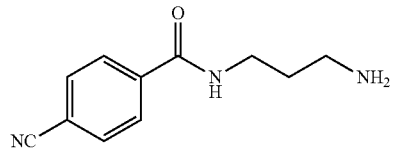 [SMILES: N#Cc1ccc(C(=O)NCCCN)cc1]

White solid of N-(3-aminopropyl)-4-cyano-benzamide (350 mg, yield of 62.0%) was prepared as follows. The t-butyl ester of 3-(4-cyano-benzamino)propylaminoformic acid (850 mg, 2.8 mmol) was dissolved in 10 ml dichloromethane, to which trifluoroacetic acid (500 μl, 6.7 mmol) was added. After stirred at room temperature for 16 h, the reaction solution was adjusted to alkaline pH by NaHCO₃ aqueous solution. After evaporated to dryness, a mixed solution of dichloromethane/methanol (10:1) was added and then subjected to ultrasound. After the solid was filtered, the filtrate was evaporated to dryness to give the target intermediate. LC-MS (m/z) 204 (M+1).

Example 6

Preparation of 4-cyano-N-(3-(2,5-dichloropyrimidinyl-4-amino)propyl)benzamide

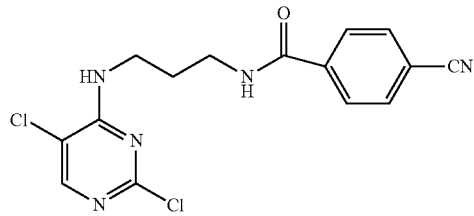 [SMILES: N#Cc1ccc(C(=O)NCCCNc2nc(Cl)ncc2Cl)cc1]

White solid of N-(3-aminopropyl)-4-cyano-benzamide (3.5 g, yield of 78.0%) was prepared as follows. 2,4,5- trichloropyrimidine (2.6 g, 14.2 mmol), N-(3-aminopropyl)-4-cyano-benzamide (2.6 g, 12.8 mmol) and triethylamine (2 ml, 14 mmol) were dissolved in 50 ml ethanol. After the reaction solution was heated to 70° C. and stirred for 4 h, the reaction was finished. The solution was evaporated to dryness, and then washed by diethyl ether. The target intermediate was obtained by filtration. LC-MS (m/z) 351 (M+1).

Example 7

Preparation of N-(3-(5-chloro-2-(4-fluoro-3-(N-methylacrylamido)phenylamino)pyrimidinyl-4-amino)propyl)-4-cyano-benzamide

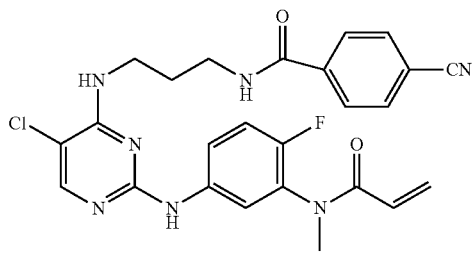 [SMILES: C=CC(=O)N(C)c1cc(Nc2ncc(Cl)c(NCCCNC(=O)c3ccc(C#N)cc3)n2)ccc1F]

White solid of N-(3-(5-chloro-2-(4-fluoro-3-(N-methylacrylamido)phenylamino)pyrimidinyl-4-amino)propyl)-4-cyano-benzamide (3.1 g, yield of 60.0%) was prepared as follows. N-(3-aminopropyl)-4-cyano-benzamide (4.0 g, 11.4 mmol), N-(5-amino-2-fluorophenyl)-N-methylacrylamide (2.7 g, 13.9 mmol) and trifluoroacetic acid (1 ml, 7 mmol) were dissolved in 60 ml isopropanol. After the reaction solution was heated to 90° C. and stirred for 24 h, the reaction was finished. The reaction solution was poured into NaHCO$_3$ aqueous solution to precipitate the solid. The mixture stood and was then filtered. The crude product was dissolved in ethyl acetate and subjected to ultrasound. After filtration, the target compound was obtained. $^1$H-NMR (DMSO-d$_6$) δ 1.80-1.83 (m, 2H, CH$_2$), 3.10-3.12 (m, 2H, CH$_2$), 3.32 (s, 3H, CH$_3$), 3.44-3.46 (m, 2H, CH$_2$), 5.59 (d, J=9.4 Hz, 1H, CH), 6.02-6.08 (m, 1H, CH), 6.18 (d, J=16.0 Hz, 1H, CH), 7.21-7.23 (m, 1H, Ar—H), 7.26-7.27 (m, 1H, Ar—H), 7.64 (s, 1H, pyrimidine-NH), 7.91 (s, 1H, Ar—H), 7.93 (s, 1H, pyrimidine-H), 7.95-7.96 (m, 2H, Ar—H), 7.97-7.98 (m, 2H, Ar—H), 8.72 (s, 1H, NH), 9.43 (s, 1H, benzene ring-NH). LC-MS (m/z) 508 (M+1).

Example 8

Preparation of N-(2-fluoro-5-nitrophenyl)acrylamide

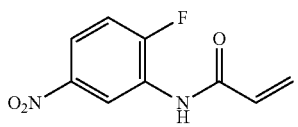

Yellow solid of N-(2-fluoro-5-nitrophenyl)acrylamide (0.3 g, yield of 71.4%) was prepared from 2-fluoro-5-nitroaniline (0.3 g, 2.0 mmol) and acryloyl chloride (0.27 g, 3 mmol) based on the similar steps according to Example 2. LC-MS (m/z) 211 (M+1).

Example 9

Preparation of N-(5-amino-2-fluorophenyl)acrylamide

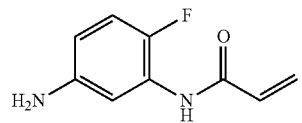

Brown solid of N-(5-amino-2-fluorophenyl)acrylamide (0.1 g, yield of 46.7%) was prepared from N-(2-fluoro-5-nitrophenyl)acrylamide (0.125 g, 4.7 mmol) based on the similar steps according to Example 3. LC-MS (m/z) 181 (M+1).

Example 10

Preparation of t-butyl ester of 3-(4-trifluoromethylbenzamino)propylamino formic acid

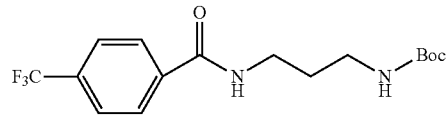 [SMILES: CC(C)(C)OC(=O)NCCCNC(=O)c1ccc(C(F)(F)F)cc1]

White solid of t-butyl ester of 3-(4-trifluoromethylbenzamino)propylamino formic acid (0.22 g, yield of 90%) was prepared from t-butyl ester of 3-aminopropylamino formic acid (0.4 g, 2.4 mmol) and 4-trifluoromethyl benzoic acid (0.38 g, 2 mmol) based on the similar steps according to Example 4. LC-MS (m/z) 347 (M+1).

Example 11

Preparation of N-(3-aminopropyl)-4-trifluoromethylbenzamide

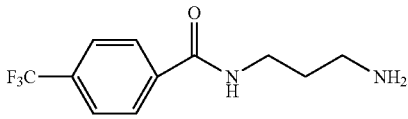 [SMILES: NCCCNC(=O)c1ccc(C(F)(F)F)cc1]

Yellow liquid of N-(3-aminopropyl)-4-trifluoromethylbenzamide (1.1 g, yield of 53%) was prepared from t-butyl ester of 3-(4-trifluoromethylbenzamino)propylamino formic acid (2.8 g, 8 mmol) based on the similar steps according to Example 5. LC-MS (m/z) 247 (M+1).

Example 12

Preparation of N-(3-(2,5-dichloropyrimidinyl-4-amino)propyl)-4-trifluoromethylbenzamide

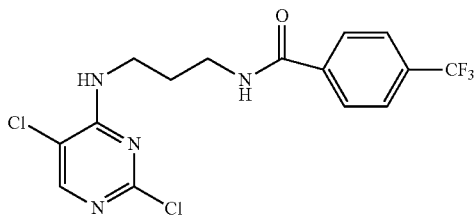 [SMILES: O=C(NCCCNc1nc(Cl)ncc1Cl)c1ccc(C(F)(F)F)cc1]

White solid of N-(3-(2,5-dichloropyrimidinyl-4-amino)propyl)-4-trifluoromethylbenzamide (1.9 g, yield of 57%) was prepared from 2,4,5-trichloropyrimidine (1.46 g, 8 mmol) and N-(3-aminopropyl)-4-trifluoromethylbenzamide (1.9 g, 8 mmol) based on the similar steps according to Example 6. LC-MS (m/z) 393 (M+1).

Example 13

Preparation of N-(3-(2-(3-acrylamido-4-fluoro-phenylamino)-5-chloropyrimidinyl-4-amino)propyl)-4-trifluoromethylbenzamide

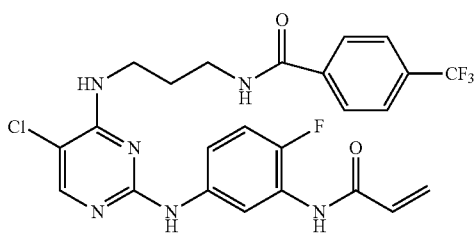 [SMILES: C=CC(=O)Nc1cc(Nc2ncc(Cl)c(NCCCNC(=O)c3ccc(C(F)(F)F)cc3)n2)ccc1F]

Grey solid of N-(3-(2-(3-acrylamido-4-fluoro-phenylamino)-5-chloropyrimidinyl-4-amino)propyl)-4-trifluoromethylbenzamide (18 mg, yield of 33%) was prepared from N-(3-(2,5-dichloropyrimidinyl-4-amino)propyl)-4-trifluoromethylbenzamide (39 mg, 0.1 mmol) and N-(5-amino-2-fluorophenyl)acrylamide (20 mg, 0.11 mmol) based on the similar steps according to Example 7. $^1$H-NMR (DMSO-$d_6$) δ 1.85-1.88 (m, 2H, CH$_2$), 3.32-3.37 (m, 2H, CH$_2$), 3.55-3.58 (m, 2H, CH$_2$), 5.76-5.79 (m, 1H, CH), 6.27-6.32 (m, 1H, CH), 6.61-6.68 (m, 1H, CH), 7.21 (t, J=10.04 Hz, 1H, pyrimidine-NH), 7.36-7.40 (m, 1H, Ar—H), 7.82 (d, J=8.16 Hz, 2H, Ar—H), 8.02 (d, J=8.1 Hz, 2H, Ar—H), 8.16 (s, 1H, pyrimidine-H), 8.28 (s, 1H, Ar—H), 8.37-8.38 (m, 1H, NH), 8.73-8.76 (m, 1H, NH), 9.99 (s, 1H, benzene ring-NH), 10.28 (s, 1H, benzene ring-NH). LC-MS (m/z) 537 (M+1).

Example 14

Preparation of t-butyl ester of 3-(4-fluorobenzamino)propylamino formic acid

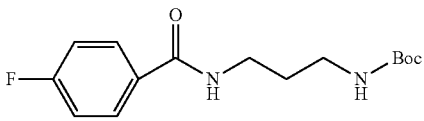 [SMILES: CC(C)(C)OC(=O)NCCCNC(=O)c1ccc(F)cc1]

White solid of t-butyl ester of 3-(4-fluorobenzamino)propylaminoformic acid (800 mg, yield of 94.1%) was prepared from t-butyl ester of 3-aminopropylamino formic acid (500 mg, 2.87 mmol) and 4-fluorobenzoic acid (400 mg, 2.86 mmol) based on the similar steps according to Example 4. LC-MS (m/z) 297 (M+1).

Example 15

Preparation of N-(3-aminopropyl)-4-fluorobenzamide

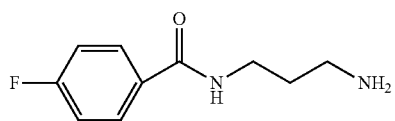 [SMILES: NCCCNC(=O)c1ccc(F)cc1]

White solid of N-(3-aminopropyl)-4-fluorobenzamide (400 mg, yield of 75.2%) was prepared from t-butyl ester of 3-(4-fluorobenzamino)propylamino formic acid (800 mg, 2.70 mmol) based on the similar steps according to Example 5. LC-MS (m/z) 197 (M+1).

Example 16

Preparation of N-(3-(2,5-dichloropyrimidinyl-4-amino)propyl)-4-fluorobenzamide

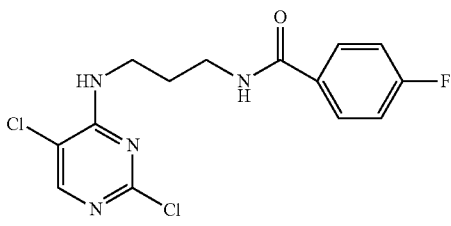 [SMILES: O=C(NCCCNc1nc(Cl)ncc1Cl)c1ccc(F)cc1]

White solid of N-(3-(2,5-dichloropyrimidinyl-4-amino)propyl)-4-fluorobenzamide (440 mg, yield of 63.2%) was prepared from 2,4,5-trichloropyrimidine (400 mg, 2.19 mmol) and N-(3-aminopropyl)-4-fluorobenzamide (400 mg, 2.03 mmol) based on the similar steps according to Example 6. LC-MS (m/z) 343 (M+1).

Example 17

Preparation of N-(3-(2-(3-acrylamido-4-fluoro-phenylamino)-5-chloropyrimidinyl-4-amino)propyl)-4-fluorobenzamide

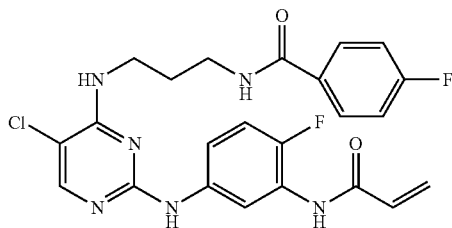 [SMILES: C=CC(=O)Nc1cc(Nc2ncc(Cl)c(NCCCNC(=O)c3ccc(F)cc3)n2)ccc1F]

White solid of N-(3-(2-(3-acrylamido-4-fluoro-phenylamino)-5-chloropyrimidinyl-4-amino)propyl)-4-fluorobenzamide (8 mg, yield of 9.41%) was prepared from N-(3-(2,5-dichloropyrimidinyl-4-amino)propyl)-4-fluorobenzamide (60 mg, 0.17 mmol) and N-(5-amino-2-fluorophenyl)acrylamide (40 mg, 0.22 mmol) based on the similar steps according to Example 7. $^1$H-NMR (DMSO-$d_6$) δ 1.79-1.83 (m, 2H, $CH_2$), 3.31-3.33 (m, 2H, $CH_2$), 3.49-3.51 (m, 2H, $CH_2$), 5.75 (d, J=11.2 Hz, 1H, CH), 6.26 (d, J=16.99 Hz, 1H, CH), 6.55-6.62 (m, 1H, CH), 7.11 (t, J=9.92 Hz, 1H, Ar—H), 7.22 (t, J=5.66 Hz, 1H, pyrimidine-NH), 7.28 (t, J=8.73 Hz, 2H, Ar—H), 7.47 (t, J=4.93 Hz, 1H, Ar—H), 7.88-7.93 (m, 3H, Ar—H, pyrimidine-H), 8.31 (d, J=5.12 Hz, 1H, Ar—H), 8.50-8.52 (m, 1H, NH), 9.26 (s, 1H, benzene ring-NH), 9.85 (s, 1H, benzene ring-NH). LC-MS (m/z) 487 (M+1).

Example 18

Preparation of N-(3-(2-chloro-5-methylpyrimidinyl-4-amino)propyl)-4-fluorobenzamide

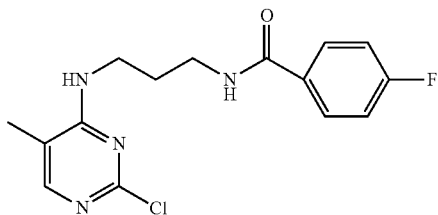 [SMILES: Cc1cnc(Cl)nc1NCCCNC(=O)c1ccc(F)cc1]

White solid of N-(3-(2-chloro-5-methylpyrimidinyl-4-amino)propyl)-4-fluorobenzamide (40 mg, yield of 52.3%) was prepared from 2,4-dichloro-5-methylpyrimidine (40 mg, 0.25 mmol) and N-(3-aminopropyl)-4-fluorobenzamide (40 mg, 0.20 mmol) based on the similar steps according to Example 6. LC-MS (m/z) 323 (M+1).

Example 19

Preparation of 4-fluoro-N-(3-(2-(4-fluoro-3-(N-methylacrylamido)phenylamino)-5-methylpyrimidinyl-4-amino)propyl)benzamide

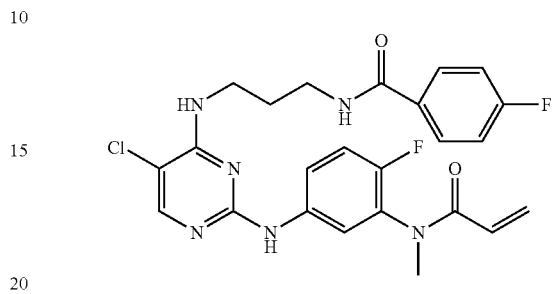

White solid of 4-fluoro-N-(3-(2-(4-fluoro-3-(N-methylacrylamido)phenylamino)-5-methylpyrimidinyl-4-amino)propyl)benzamide (5 mg, yield of 8.68%) was prepared from N-(3-(2-chloro-5-methylpyrimidinyl-4-amino)propyl)-4-fluorobenzamide (40 mg, 0.12 mmol) and N-(5-amino-2-fluorophenyl)-N-methylacrylamide (40 mg, 0.21 mmol) based on the similar steps according to Example 7. $^1$H-NMR (DMSO-$d_6$) δ 1.80-1.83 (m, 2H, $CH_2$), 1.92 (s, 3H, $CH_3$), 3.19 (s, 3H, $CH_3$), 3.30-3.32 (m, 2H, $CH_2$), 3.42-3.44 (m, 2H, $CH_2$), 5.58-5.61 (m, 1H, CH), 6.04-6.11 (m, 1H, CH), 6.16-6.21 (m, 1H, CH), 6.72 (t, J=5.17 Hz, 1H, Ar—H), 7.21 (t, J=9.44 Hz, 1H, pyrimidine-NH), 7.28 (t, J=8.8 Hz, 2H, Ar—H), 7.66-7.68 (m, 2H, Ar—H, pyrimidine-H), 7.88-7.92 (m, 2H, Ar—H), 7.98-7.99 (m, 1H, Ar—H), 8.51 (t, J=5.26 Hz, 1H, NH), 9.09 (s, 1H, benzene ring-NH). LC-MS (m/z) 481 (M+1).

Example 20

Preparation of N-(3-(2-chloro-5-methylpyrimidinyl-4-amino)propyl)-4-trifluoromethylbenzamide

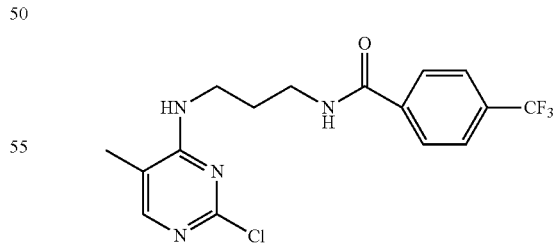

White solid of N-(3-(2-chloro-5-methylpyrimidinyl-4-amino)propyl)-4-trifluoromethylbenzamide (0.26 g, yield of 72%) was prepared from 2,4-dichloro-5-methylpyrimidine (0.16 g, 1 mmol) and N-(3-aminopropyl)-4-trifluoromethylbenzamide (0.24 g, 1 mmol) based on the similar steps according to Example 6. LC-MS (m/z) 373 (M+1).

Example 21

Preparation of N-(3-(2-(4-fluoro-3-(N-methylacrylamido)phenylamino)-5-methylpyrimidinyl-4-amino)propyl)-4-trifluoromethylbenzamide

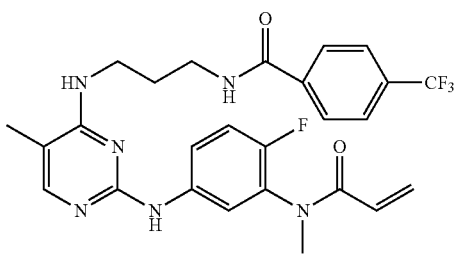 [SMILES: C=CC(=O)N(C)c1cc(Nc2ncc(C)c(NCCCNC(=O)c3ccc(C(F)(F)F)cc3)n2)ccc1F]

White solid of N-(3-(2-(4-fluoro-3-(N-methylacrylamido)phenylamino)-5-methylpyrimidinyl-4-amino)propyl)-4-trifluoromethylbenzamide (0.26 g, yield of 72%) was prepared from N-(3-(2-chloro-5-methylpyrimidinyl-4-amino)propyl)-4-trifluoromethylbenzamide (75 mg, 0.2 mmol) and N-(5-amino-2-fluorophenyl)-N-methylacrylamide (70 mg, 0.3 mmol) based on the similar steps according to Example 7. $^1$H-NMR (DMSO-$d_6$) δ 1.81-1.87 (m, 2H, CH$_2$), 1.93 (s, 3H, CH$_3$), 3.19 (s, 3H, CH$_3$), 3.36-3.38 (m, 2H, CH$_2$), 3.44-3.46 (m, 2H, CH$_2$), 5.58-5.61 (m, 1H, CH), 6.04-6.11 (m, 1H, CH), 6.16-6.21 (m, 1H, CH), 6.73 (t, J=5.64 Hz, 1H, Ar—H), 7.21 (t, J=9.4 Hz, 1H, pyrimidine-NH), 7.66-7.68 (m, 2H, Ar—H, pyrimidine-H), 7.84 (d, J=8.3 Hz, 2H, Ar—H), 7.98-8.00 (m, 1H, Ar—H), 8.03 (d, J=8.1 Hz, 2H, Ar—H), 8.71-9.74 (m, 1H, NH), 9.10 (s, 1H, benzene ring-NH). LC-MS (m/z) 531 (M+1).

Example 22

Preparation of N-(3-(5-chloro-2-(4-fluoro-3-(N-methylacrylamido)phenylamino)pyrimidinyl-4-amino)propyl)-4-trifluoromethylbenzamide

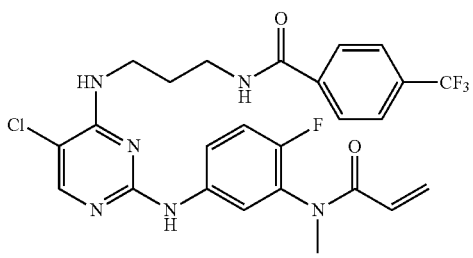 [SMILES: C=CC(=O)N(C)c1cc(Nc2ncc(Cl)c(NCCCNC(=O)c3ccc(C(F)(F)F)cc3)n2)ccc1F]

Grey solid of N-(3-(5-chloro-2-(4-fluoro-3-(N-methylacrylamido)phenylamino)pyrimidinyl-4-amino)propyl)-4-trifluoromethylbenzamide (0.23 g, yield of 42%) was prepared from N-(3-(2,5-dichloropyrimidinyl-4-amino)propyl)-4-trifluoromethylbenzamide (0.39 g, 1 mmol) and N-(5-amino-2-fluorophenyl)-N-methylacrylamide (0.28 g, 1.5 mmol) based on the similar steps according to Example 7. $^1$H-NMR (DMSO-$d_6$) δ 1.81-1.84 (m, 2H, CH$_2$), 3.31-3.33 (m, 2H, CH$_2$), 3.45-3.47 (m, 2H, CH$_2$), 5.60 (d, J=9.6 Hz, 1H, CH), 6.02-6.08 (m, 1H, CH), 6.18 (d, J=15.1 Hz, 1H, CH), 7.25-7.29 (m, 1H, Ar—H), 7.61-7.67 (m, 3H, Ar—H, pyrimidine-NH), 7.82-7.84 (m, 3H, Ar—H, pyrimidine-H), 8.00-8.03 (m, 3H, Ar—H, NH), 8.71 (s, 1H, benzene ring-NH), 9.71 (s, 1H, benzene ring-NH). LC-MS (m/z) 551 (M+1).

Example 23

Preparation of N-(3-(5-chloro-2-(4-fluoro-3-(N-methylacrylamido)phenylamino)pyrimidinyl-4-amino)propyl)-4-fluorobenzamide

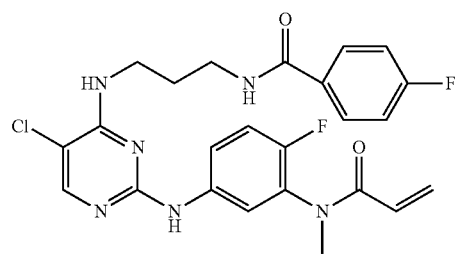 [SMILES: C=CC(=O)N(C)c1cc(Nc2ncc(Cl)c(NCCCNC(=O)c3ccc(F)cc3)n2)ccc1F]

White solid of N-(3-(5-chloro-2-(4-fluoro-3-(N-methylacrylamido)phenylamino)pyrimidinyl-4-amino)propyl)-4-fluorobenzamide (117 mg, yield of 40.3%) was prepared from N-(3-(2,5-dichloropyrimidinyl-4-amino)propyl)-4-fluorobenzamide (200 mg, 0.58 mmol) and N-(5-amino-2-fluorophenyl)-N-methylacrylamide (150 mg, 0.77 mmol) based on the similar steps according to Example 7. $^1$H-NMR (DMSO-$d_6$) δ 1.78-1.81 (m, 2H, CH$_2$), 3.28-3.29 (m, 2H, CH$_2$), 3.32 (s, 3H, CH$_3$), 3.43-3.45 (m, 2H, CH$_2$), 5.59 (d, J=9.8 Hz, 1H, CH), 6.05-6.09 (m, 1H, CH), 6.15-6.20 (m, 1H, CH), 7.22-7.30 (m, 4H, Ar—H), 7.64-7.66 (m, 1H, pyrimidine-NH), 7.87-7.91 (m, 3H, Ar—H), 7.96 (s, 1H, pyrimidine-H), 8.50 (t, J=5.2 Hz, 1H, NH), 9.43 (s, 1H, benzene ring-NH). LC-MS (m/z) 501 (M+1).

Example 24

Preparation of t-butyl ester of 3-(1-methylpiperidinyl-4-formamino)propylamino formic acid

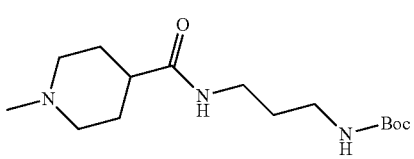 [SMILES: CN1CCC(C(=O)NCCCNC(=O)OC(C)(C)C)CC1]

White solid of t-butyl ester of 3-(1-methylpiperidinyl-4-formamino)propylamino formic acid (220 mg, yield of 25.6%) was prepared from t-butyl ester of 3-aminopropylamino formic acid (500 mg, 2.87 mmol) and 1-methylpiperidinyl-4-carboxylic acid (410 mg, 2.87 mmol) based on the similar steps according to Example 4. LC-MS (m/z) 300 (M+1).

Example 25

Preparation of N-(3-aminopropyl)-N-methylpiperidinyl-4-formamide

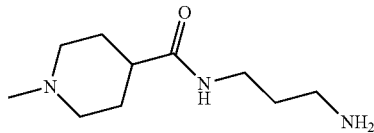

White solid of N-(3-aminopropyl)-1-methylpiperidinyl-4-formamide (130 mg, yield of 80.1%) was prepared from t-butyl ester of 3-(1-methylpiperidinyl-4-formamino)propylamino formic acid (220 mg, 0.74 mmol) based on the similar steps according to Example 5. LC-MS (m/z) 200 (M+1).

Example 26

Preparation of N-(3-(2,5-dichloropyrimidinyl-4-amino)propyl)-1-methylpiperidinyl-4-formamide

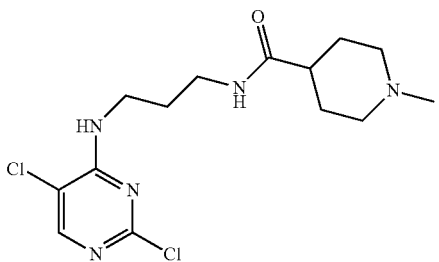 [SMILES: CN1CCC(C(=O)NCCCNc2nc(Cl)ncc2Cl)CC1]

White solid of N-(3-(2,5-dichloropyrimidinyl-4-amino)propyl)-1-methylpiperidinyl-4-formamide (200 mg, yield of 79.6%) was prepared from 2,4,5-trichloropyrimidine (130 mg, 0.71 mmol) and N-(3-aminopropyl)-1-methylpiperidinyl-4-formamide (130 mg, 0.65 mmol) based on the similar steps according to Example 6. LC-MS (m/z) 346 (M+1).

Example 27

Preparation of N-(3-(5-chloro-2-(4-fluoro-3-(N-methylacrylamido)phenylamino)pyrimidinyl-4-amino)propyl)-1-methylpiperidinyl-4-formamide

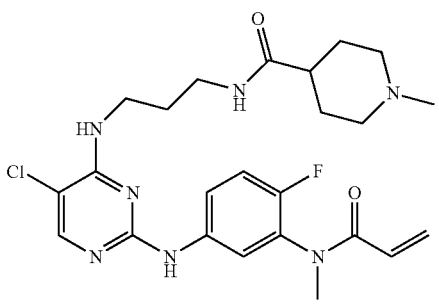 [SMILES: C=CC(=O)N(C)c1cc(Nc2ncc(Cl)c(NCCCNC(=O)C3CCN(C)CC3)n2)ccc1F]

White solid of N-(3-(5-chloro-2-(4-fluoro-3-(N-methylacrylamido)phenylamino)pyrimidinyl-4-amino)propyl)-1-methylpiperidinyl-4-formamide (12 mg, yield of 11.6%) was prepared from N-(3-(2,5-dichloropyrimidinyl-4-amino)propyl)-1-methylpiperidinyl-4-formamide (80 mg, 0.23 mmol) and N-(5-amino-2-fluorophenyl)-N-methylacrylamide (40 mg, 0.20 mmol) based on the similar steps according to Example 7. $^1$H-NMR (DMSO-$d_6$) δ 1.52-1.58 (m, 4H, 2×CH$_2$), 1.74-1.79 (m, 2H, CH$_2$), 1.96-1.99 (m, 1H, CH), 2.11 (s, 3H, CH$_3$), 3.05-3.12 (m, 4H, 2×CH$_2$), 3.13-3.16 (m, 4H, 2×CH$_2$), 3.18 (s, 3H, CH$_3$), 5.60 (d, J=9.7 Hz, 1H, CH), 6.03-6.09 (m, 1H, CH), 6.15-6.21 (m, 1H, CH), 7.25-7.30 (m, 2H, Ar—H, pyrimidine-NH), 7.64-7.69 (m, 1H, Ar—H), 7.76 (t, J=5.45 Hz, 1H, NH), 7.84-7.88 (m, 1H, Ar—H), 7.96 (s, 1H, pyrimidine-H), 9.43 (s, 1H, benzene ring-NH). LC-MS (m/z) 504 (M+1).

Example 28

Preparation of N-(3-(2-(3-acrylamido-4-fluorophenylamino)-5-chloropyrimidinyl-4-amino)propyl)-4-cyano-benzamide

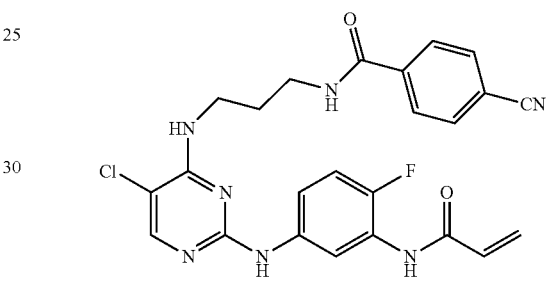

Black solid of N-(3-(2-(3-acrylamido-4-fluorophenylamino)-5-chloropyrimidinyl-4-amino)propyl)-4-cyano-benzamide (20 mg, yield of 40%) was prepared from 4-cyano-N-(3-(2,5-dichloropyrimidinyl-4-amino)propyl)benzamide (35 mg, 0.1 mmol) and N-(5-amino-2-fluorophenyl)acrylamide (22 mg, 0.12 mmol) based on the similar steps according to Example 7. $^1$H-NMR (DMSO-$d_6$) δ 1.81-1.87 (m, 2H, CH$_2$), 3.30-3.34 (m, 2H, CH$_2$), 3.52-3.57 (m, 2H, CH$_2$), 5.75-5.78 (m, 1H, CH), 6.25-6.30 (m, 1H, CH), 6.59-6.66 (m, 1H, CH), 7.19 (t, J=10.48 Hz, 1H, pyrimidine-NH), 7.36-7.40 (m, 1H, Ar—H), 7.92-7.97 (m, 4H, Ar—H), 8.11 (s, 1H, pyrimidine-H), 8.34 (d, J=4.6 Hz, 1H, Ar—H), 8.73 (t, J=5.44 Hz, 1H, NH), 9.95 (s, 1H, benzene ring-NH), 10.05 (s, 1H, benzene ring-NH). LC-MS (m/z) 494 (M+1).

Example 29

Preparation of t-butyl ester of 3-(4-dimethylaminobenzamino)propylamino formic acid

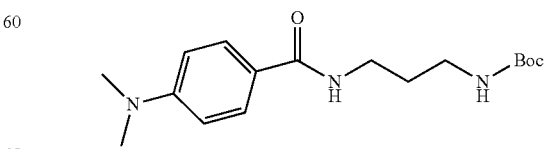

White solid of t-butyl ester of 3-(4-dimethylaminobenzamino)propylamino formic acid (840 mg, yield of 91.1%)

was prepared from t-butyl ester of 3-aminopropylamino formic acid (500 mg, 2.87 mmol) and 4-dimethylaminobenzoic acid (475 mg, 2.87 mmol) based on the similar steps according to Example 4. LC-MS (m/z) 322 (M+1).

Example 30

Preparation of N-(3-aminopropyl)-4-dimethylaminobenzamide

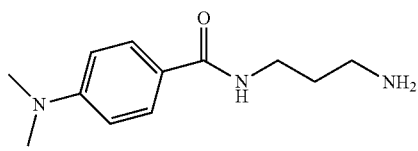 [SMILES: CN(C)c1ccc(C(=O)NCCCN)cc1]

White solid of N-(3-aminopropyl)-4-dimethylaminobenzamide (500 mg, yield of 86.5%) was prepared from t-butyl ester of 3-(4-dimethylaminobenzamino)propylamino formic acid (840 mg, 2.62 mmol) based on the similar steps according to Example 5. LC-MS (m/z) 222 (M+1).

Example 31

Preparation of N-(3-(2,5-dichloropyrimidinyl-4-amino)propyl)-4-dimethylaminobenzamide

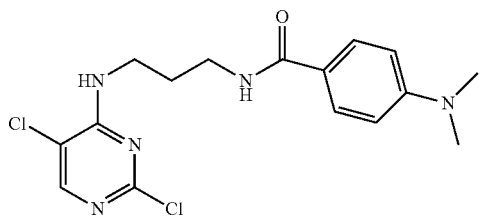 [SMILES: CN(C)c1ccc(C(=O)NCCCNc2nc(Cl)ncc2Cl)cc1]

White solid of N-(3-(2,5-dichloropyrimidinyl-4-amino)propyl)-4-dimethylaminobenzamide (700 mg, yield of 84.3%) was prepared from 2,4,5-trichloropyrimidine (550 mg, 3.00 mmol) and N-(3-aminopropyl)-4-dimethylaminobenzamide (500 mg, 2.26 mmol) based on the similar steps according to Example 6. LC-MS (m/z) 368 (M+1).

Example 32

Preparation of N-(3-(5-chloro-2-(4-fluoro-3-(N-methylacrylamido)phenylamino)

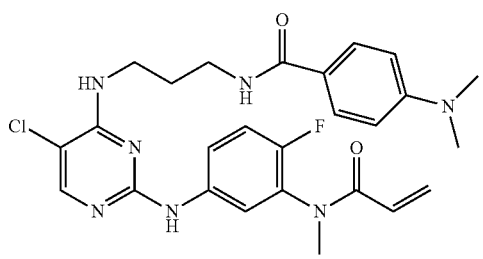 [SMILES: C=CC(=O)N(C)c1cc(Nc2ncc(Cl)c(NCCCNC(=O)c3ccc(N(C)C)cc3)n2)ccc1F]

White solid of N-(3-(5-chloro-2-(4-fluoro-3-(N-methylacrylamido)phenylamino)pyrimidinyl-4-amino)propyl)-4-dimethylamino benzamide (49 mg, yield of 58.3%) was prepared from N-(3-(2,5-dichloropyrimidinyl-4-amino)propyl)-4-dimethylaminobenzamide (50 mg, 0.14 mmol) and N-(5-amino-2-fluorophenyl)-N-methylacrylamide (30 mg, 0.15 mmol) based on the similar steps according to Example 7. $^1$H-NMR (DMSO-d$_6$) δ 1.74-1.78 (m, 2H, CH$_2$), 2.95 (s, 6H, 2×CH$_3$), 3.25-3.60 (m, 2H, CH$_2$), 3.32 (s, 3H, CH$_3$), 3.41-3.43 (m, 2H, CH$_2$), 5.59 (d, J=9.8 Hz, 1H, CH), 6.02-6.09 (m, 1H, CH), 6.16-6.20 (m, 1H, CH), 6.68 (d, J=9.8 Hz, 2H, Ar—H), 7.22-7.27 (m, 1H, Ar—H), 7.31-7.34 (m, 1H, Ar—H), 7.64-7.67 (m, 1H, pyrimidine-NH), 7.70 (d, J=8.7 Hz, 2H, Ar—H), 7.89-7.90 (m, 1H, Ar—H), 7.96 (s, 1H, pyrimidine-H), 8.14 (t, J=5.6 Hz, 1H, NH), 9.43 (s, 1H, benzene ring-NH). LC-MS (m/z) 526 (M+1).

Example 33

Preparation of t-butyl ester of 3-(2,4,6-trifluorobenzamino)propylamino formic acid

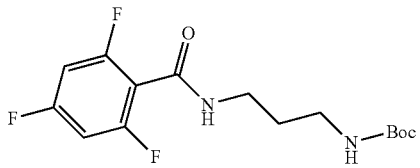 [SMILES: CC(C)(C)OC(=O)NCCCNC(=O)c1c(F)cc(F)cc1F]

White solid of t-butyl ester of 3-(2,4,6-trifluorobenzamino)propylamino formic acid (200 mg, yield of 60.1%) was prepared from t-butyl ester of 3-aminopropylamino formic acid (174 mg, 1.0 mmol) and 2,4,6-trifluorobenzoic acid (176 mg, 1.0 mmol) based on the similar steps according to Example 4. LC-MS (m/z) 333 (M+1).

Example 34

Preparation of N-(3-aminopropyl)-2,4,6-trifluorobenzamide

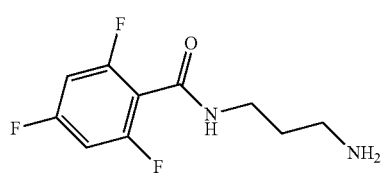 [SMILES: NCCCNC(=O)c1c(F)cc(F)cc1F]

White solid of N-(3-aminopropyl)-2,4,6-trifluorobenzamide (100 mg, yield of 43.1%) was prepared from t-butyl ester of 3-(2,4,6-trifluorobenzamino)propylamino formic acid (200 mg, 0.6 mmol) based on the similar steps according to Example 5. LC-MS (m/z) 233 (M+1).

Example 35

Preparation of N-(3-(2,5-dichloropyrimidinyl-4-amino)propyl)-2,4,6-trifluorobenzamide

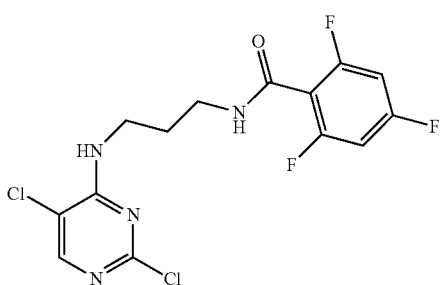 [SMILES: O=C(NCCCNc1nc(Cl)ncc1Cl)c1c(F)cc(F)cc1F]

Yellow solid of N-(3-(2,5-dichloropyrimidinyl-4-amino)propyl)-2,4,6-trifluorobenzamide (120 mg, yield of 73.6%) was prepared from 2,4,5-trichloropyrimidine (100 mg, 0.55 mmol) and N-(3-aminopropyl)-2,4,6-trifluorobenzamide (100 mg, 0.43 mmol) based on the similar steps according to Example 6. LC-MS (m/z) 379 (M+1).

Example 36

Preparation of N-(3-(5-chloro-2-(4-fluoro-3-(N-methylacrylamido)phenylamino)pyrimidinyl-4-amino)propyl)-2,4,6-trifluorobenzamide

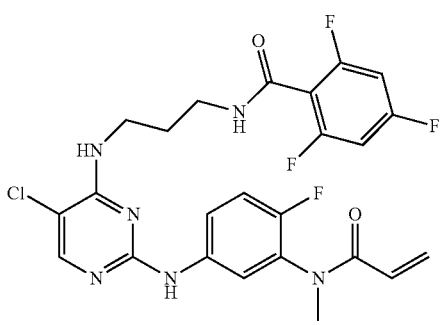 [SMILES: C=CC(=O)N(C)c1cc(Nc2ncc(Cl)c(NCCCNC(=O)c3c(F)cc(F)cc3F)n2)ccc1F]

Yellow solid of N-(3-(5-chloro-2-(4-fluoro-3-(N-methylacrylamido)phenylamino)pyrimidinyl-4-amino)propyl)-2,4,6-trifluorobenzamide (80 mg, yield of 58.3%) was prepared from N-(3-(2,5-dichloropyrimidinyl-4-amino)propyl)-2,4,6-trifluorobenzamide (120 mg, 0.32 mmol) and N-(5-amino-2-fluorophenyl)-N-methylacrylamide (110 mg, 0.56 mmol) based on the similar steps according to Example 7. $^1$H-NMR (DMSO-$d_6$) δ 1.75-1.82 (m, 2H, CH$_2$), 3.19 (s, 3H, CH$_3$), 3.25-3.31 (m, 2H, CH$_2$), 3.44-3.45 (m, 2H, CH$_2$), 5.61 (d, J=9.5 Hz, 1H, CH), 6.04-6.11 (m, 1H, CH), 6.16-6.22 (m, 1H, CH), 7.22-7.28 (m, 4H, Ar—H, pyrimidine-NH), 7.67-7.69 (m, 1H, Ar—H), 7.87 (d, J=5.2 Hz, 1H, Ar—H), 7.96 (s, 1H, pyrimidine-H), 8.71 (t, J=5.4 Hz, 1H, NH), 9.40 (s, 1H, benzene ring-NH). LC-MS (m/z) 537 (M+1).

Example 37

Preparation of t-butyl ester of 3-(4-methoxybenzamino)propylamino formic acid

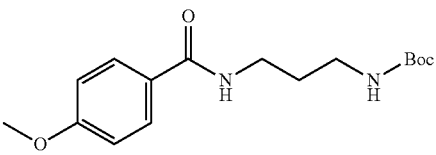 [SMILES: COc1ccc(C(=O)NCCCNC(=O)OC(C)(C)C)cc1]

White solid of t-butyl ester of 3-(4-methoxybenzamino)propylamino formic acid (800 mg, yield of 90.4%) was prepared from t-butyl ester of 3-aminopropylamino formic acid (500 mg, 2.87 mmol) and 4-methoxybenzoic acid (437 mg, 2.87 mmol) based on the similar steps according to Example 4. LC-MS (m/z) 309 (M+1).

Example 38

Preparation of N-(3-aminopropyl)-4-methoxylbenzamide

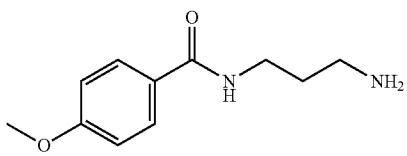

White solid of N-(3-aminopropyl)-4-methoxylbenzamide (500 mg, yield of 92.6%) was prepared from t-butyl ester of 3-(4-methoxylbenzamino)propylamino formic acid (800 mg, 2.60 mmol) based on the similar steps according to Example 5. LC-MS (m/z) 209 (M+1).

Example 39

Preparation of N-(3-(2,5-dichloropyrimidinyl-4-amino)propyl)-4-methoxylbenzamide

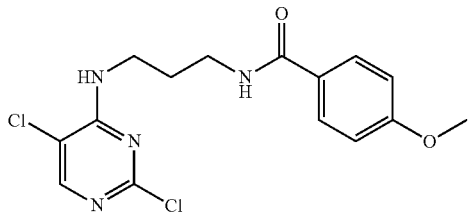 [SMILES: COc1ccc(C(=O)NCCCNc2nc(Cl)ncc2Cl)cc1]

White solid of N-(3-(2,5-dichloropyrimidinyl-4-amino)propyl)-4-methoxylbenzamide (600 mg, yield of 70.3%) was prepared from 2,4,5-trichloropyrimidine (690 mg, 3.74 mmol) and N-(3-aminopropyl)-4-methoxylbenzamide (500 mg, 2.40 mmol) based on the similar steps according to Example 6. LC-MS (m/z) 355 (M+1).

Example 40

Preparation of N-(3-(5-chloro-2-(4-fluoro-3-(N-methylacrylamido)phenylamino)pyrimidinyl-4-amino)propyl)-4-methoxylbenzamide

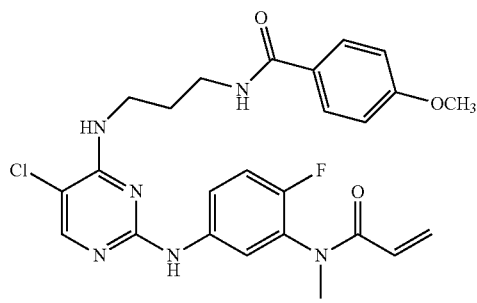 [SMILES: C=CC(=O)N(C)c1cc(Nc2ncc(Cl)c(NCCCNC(=O)c3ccc(OC)cc3)n2)ccc1F]

White solid of N-(3-(5-chloro-2-(4-fluoro-3-(N-methylacrylamido)phenylamino)pyrimidinyl-4-amino)propyl)-4-methoxylbenzamide (10 mg, yield of 13.9%) was prepared from N-(3-(2,5-dichloropyrimidinyl-4-amino)propyl)-4-methoxylbenzamide (50 mg, 0.14 mmol) and N-(5-amino-2-fluorophenyl)-N-methylacrylamide (30 mg, 0.15 mmol) based on the similar steps according to Example 7. $^1$H-NMR (DMSO-d$_6$) δ 1.77-1.80 (m, 2H, CH$_2$), 3.19 (s, 3H, CH$_3$), 3.28-3.31 (m, 2H, CH$_2$), 3.43-3.45 (m, 2H, CH$_2$), 3.80 (s, 3H, CH$_3$), 5.59 (d, J=9.5 Hz, 1H, CH), 6.03-6.09 (m, 1H, CH), 6.16-6.21 (m, 1H, CH), 6.97 (d, J=8.7 Hz, 2H, Ar—H), 7.21-7.27 (m, 2H, Ar—H, pyrimidine-NH), 7.65-7.67 (m, 1H, Ar—H), 7.81 (d, J=8.7 Hz, 2H, Ar—H), 7.89 (d, J=6.4 Hz, 1H, Ar—H), 7.96 (s, 1H, pyrimidine-H), 8.31 (t, J=5.2 Hz, 1H, NH), 9.40 (s, 1H, benzene ring-NH). LC-MS (m/z) 513 (M+1).

Example 41

Preparation of t-butyl ester of 3-(2-cyano-nicotinamino)propylamino formic acid

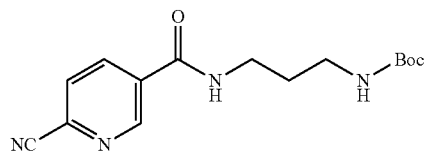 [SMILES: CC(C)(C)OC(=O)NCCCNC(=O)c1ccc(C#N)nc1]

White solid of t-butyl ester of 3-(2-cyano-nicotinamino)propylamino formic acid (400 mg, yield of 91.3%) was prepared from t-butyl ester of 3-aminopropylamino formic acid (250 mg, 1.44 mmol) and 6-cyano-nicotinic acid (212 mg, 1.44 mmol) based on the similar steps according to Example 4. LC-MS (m/z) 305 (M+1).

Example 42

Preparation of N-(3-aminopropyl)-6-cyano-nicotinamide

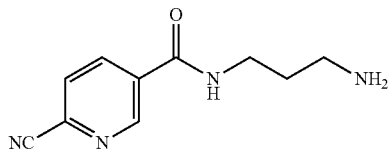 [SMILES: N#Cc1ccc(C(=O)NCCCN)cn1]

White solid of N-(3-aminopropyl)-6-cyano-nicotinamide (240 mg, yield of 89.6%) was prepared from t-butyl ester of 3-(2-cyano-nicotinamino)propylamino formic acid (400 mg, 1.32 mmol) based on the similar steps according to Example 5. LC-MS (m/z) 205 (M+1).

Example 43

Preparation of 6-cyano-N-(3-(2,5-dichloropyrimidinyl-4-amino)propyl)nicotinamide

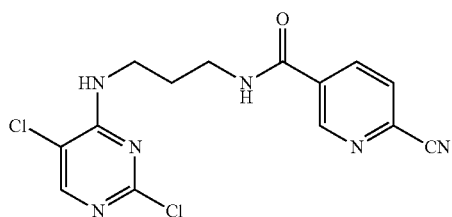 [SMILES: N#Cc1ccc(C(=O)NCCCNc2nc(Cl)ncc2Cl)cn1]

White solid of 6-cyano-N-(3-(2,5-dichloropyrimidinyl-4-amino)propyl)nicotinamide (80 mg, yield of 19.3%) was prepared from 2,4,5-trichloropyrimidine (280 mg, 1.53 mmol) and N-(3-aminopropyl)-6-cyano-nicotinamide (240 mg, 1.18 mmol) based on the similar steps according to Example 6. LC-MS (m/z) 351 (M+1).

Example 44

Preparation of N-(3-(5-chloro-2-(4-fluoro-3-(N-methylacrylamido)phenylamino)pyrimidinyl-4-amino)propyl)-6-cyanonicotinamide

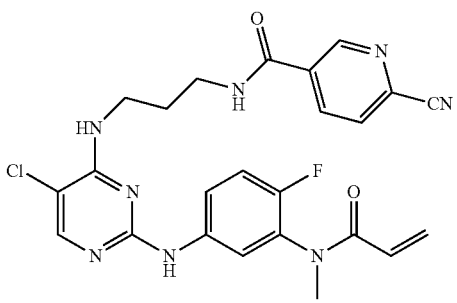 [SMILES: C=CC(=O)N(C)c1cc(Nc2ncc(Cl)c(NCCCNC(=O)c3ccc(C#N)nc3)n2)ccc1F]

White solid of N-(3-(5-chloro-2-(4-fluoro-3-(N-methyl-acrylamido)phenylamino)pyrimidinyl-4-amino)propyl)-6-cyano-nicotinamide (15 mg, yield of 17.4%) was prepared from 6-cyano-N-(3-(2,5-dichloropyrimidinyl-4-amino)propyl)nicotinamide (60 mg, 0.17 mmol) and N-(5-amino-2-fluorophenyl)-N-methylacrylamide (46 mg, 0.24 mmol) based on the similar steps according to Example 7. $^1$H-NMR (DMSO-$d_6$) δ 1.81-1.88 (m, 2H, $CH_2$), 3.21 (s, 3H, $CH_3$), 3.32-3.36 (m, 2H, $CH_2$), 3.46-3.51 (m, 2H, $CH_2$), 5.61 (d, J=9.8 Hz, 1H, CH), 6.04-6.1 (m, 1H, CH), 6.17-6.22 (m, 1H, CH), 7.29 (t, J=9.3 Hz, 1H, pyrimidine-NH), 7.61-7.62 (m, 1H, Ar—H), 7.78 (s, 1H, Ar—H), 7.83 (d, J=5.3 Hz, 1H, Ar—H), 8.06 (s, 1H, pyrimidine-H), 8.17 (d, J=7.4 Hz, 1H, Ar—H), 8.36-8.41 (m, 1H, Ar—H), 8.89 (t, J=5.4 Hz, 1H, NH), 9.09 (s, 1H, Ar—H), 9.85 (s, 1H, benzene ring-NH). LC-MS (m/z) 509 (M+1).

Example 45

Preparation of t-butyl ester of 3-(4-hydroxybenzamino)propylamino formic acid

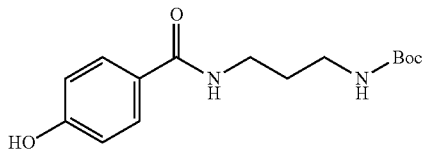 [SMILES: CC(C)(C)OC(=O)NCCCNC(=O)c1ccc(O)cc1]

White solid of t-butyl ester of 3-(4-hydroxybenzamino)propylamino formic acid (600 mg, yield of 71.1%) was prepared from t-butyl ester of 3-aminopropyl t-butylamino formic acid (500 mg, 2.87 mmol) and 4-hydroxybenzoic acid (440 mg, 2.87 mmol) based on the similar steps according to Example 4. LC-MS (m/z) 295 (M+1).

Example 46

Preparation of N-(3-aminopropyl)-4-hydroxybenzamide

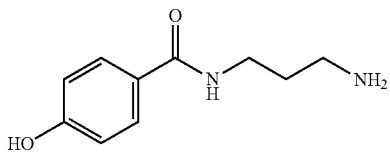 [SMILES: NCCCNC(=O)c1ccc(O)cc1]

White solid of N-(3-aminopropyl)-4-hydroxybenzamide (300 mg, yield of 75.8%) was prepared from t-butyl ester of 3-(4-hydroxybenzamino)propylamino formic acid (600 mg, 2.04 mmol) based on the similar steps according to Example 5. LC-MS (m/z) 195 (M+1).

Example 47

Preparation of N-(3-(2,5-dichloropyrimidinyl-4-amino)propyl)-4-hydroxy benzamide

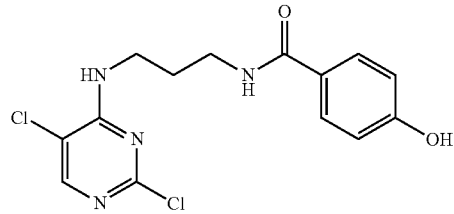

White solid of N-(3-(2,5-dichloropyrimidinyl-4-amino)propyl)-4-hydroxy benzamide (200 mg, yield of 84.3%) was prepared from 2,4,5-trichloropyrimidine (300 mg, 1.64 mmol) and N-(3-aminopropyl)-4-hydroxybenzamide (300 mg, 1.54 mmol) based on the similar steps according to Example 6. LC-MS (m/z) 341 (M+1).

Example 48

Preparation of N-(3-(5-chloro-2-(4-fluoro-3-(N-methylacrylamido)phenylamino)pyrimidinyl-4-amino)propyl)-4-hydroxybenzamide

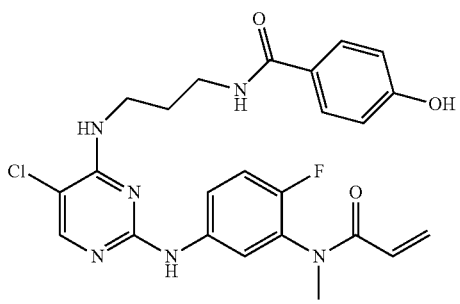

White solid of N-(3-(5-chloro-2-(4-fluoro-3-(N-methyl-acrylamido)phenylamino)pyrimidinyl-4-amino)propyl)-4-hydroxybenzamide (3 mg, yield of 1.3%) was prepared from N-(3-(2,5-dichloropyrimidinyl-4-amino)propyl)-4-hydroxybenzamide (200 mg, 0.47 mmol) and N-(5-amino-2-fluorophenyl)-N-methylacrylamide (100 mg, 0.52 mmol) based on the similar steps according to Example 7. $^1$H-NMR (DMSO-$d_6$) δ 1.75-1.81 (m, 2H, $CH_2$), 3.19 (s, 3H, $CH_3$), 3.27-3.29 (m, 2H, $CH_2$), 3.42-3.44 (m, 2H, $CH_2$), 5.59 (d, J=9.4 Hz, 1H, CH), 6.03-6.09 (m, 1H, CH), 6.16-6.20 (m, 1H, CH), 6.78 (d, J=7.9 Hz, 2H, Ar—H), 7.24-7.27 (m, 2H, Ar—H, pyrimidine-NH), 7.67-7.69 (m, 1H, Ar—H), 7.70 (d, J=8.1 Hz, 2H, Ar—H), 7.88-7.90 (m, 1H, Ar—H), 7.96 (s, 1H, pyrimidine-H), 8.20 (s, 1H, NH), 9.40 (s, 1H, benzene ring-NH), 9.89 (s, 1H, OH). LC-MS (m/z) 499 (M+1).

Example 49

Preparation of t-butyl ester of 3-(4-cyano-2-fluorobenzamino)propylamino formic acid

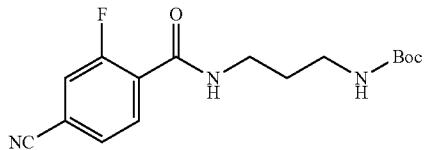 [SMILES: CC(C)(C)OC(=O)NCCCNC(=O)c1ccc(C#N)cc1F]

White solid of t-butyl ester of 3-(4-cyano-2-fluorobenzamino)propylamino formic acid (450 mg, yield of 70.1%) was prepared from t-butyl ester of 3-aminopropylamino formic acid (348 mg, 2.0 mmol) and 4-cyano-2-fluobenzoic acid (330 mg, 2.0 mmol) based on the similar steps according to Example 4. LC-MS (m/z) 322 (M+1).

Example 50

Preparation of N-(3-aminopropyl)-4-cyano-2-fluorobenzamide

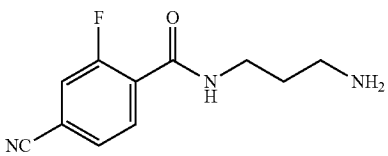 [SMILES: N#Cc1ccc(C(=O)NCCCN)c(F)c1]

White solid of N-(3-aminopropyl)-4-cyano-2-fluorobenzamide (278 mg, yield of 90.0%) was prepared from t-butyl ester of 3-(4-cyano-2-fluorobenzamino)propylamino formic acid (450 mg, 1.4 mmol) based on the similar steps according to Example 5. LC-MS (m/z) 222 (M+1).

Example 51

Preparation of 4-cyano-N-(3-(2,5-dichloropyrimidinyl-4-amino)propyl)-2-fluorobenzamide

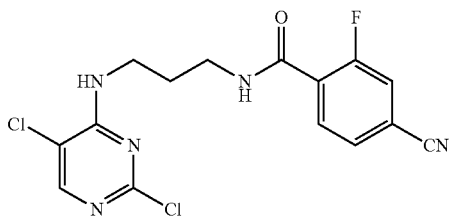 [SMILES: N#Cc1ccc(C(=O)NCCCNc2nc(Cl)ncc2Cl)c(F)c1]

White solid of 4-cyano-N-(3-(2,5-dichloropyrimidinyl-4-amino)propyl)-4-fluorobenzamide (312 mg, yield of 67.4%) was prepared from 2,4,5-trichloropyrimidine (238 mg, 1.3 mmol) and N-(3-aminopropyl)-4-cyano-2-fluorobenzamide (278 mg, 1.26 mmol) based on the similar steps according to Example 6. LC-MS (m/z) 368 (M+1).

Example 52

Preparation of N-(3-(5-chloro-2-(4-fluoro-3-(N-methylacrylamido)phenylamino)pyrimidinyl-4-amino)propyl)-4-cyano-2-fluorobenzamide

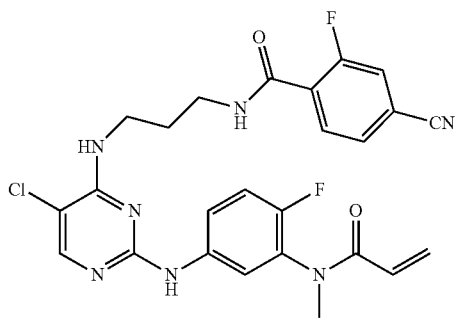 [SMILES: C=CC(=O)N(C)c1cc(Nc2ncc(Cl)c(NCCCNC(=O)c3ccc(C#N)cc3F)n2)ccc1F]

White solid of N-(3-(5-chloro-2-(4-fluoro-3-(N-methylacrylamido)phenylamino)pyrimidinyl-4-amino)propyl)-4-cyano-2-fluorobenzamide (106 mg, yield of 49.3%) was prepared from 4-cyano-N-(3-(2,5-dichloropyrimidinyl-4-amino)propyl)-2-fluorobenzamide (150 mg, 0.41 mmol) and N-(5-amino-2-fluorophenyl)-N-methylacrylamide (87 mg, 0.45 mmol) based on the similar steps according to Example 7. $^1$H-NMR (DMSO-$d_6$) δ 1.80-1.83 (m, 2H, CH$_2$), 3.20 (s, 3H, CH$_3$), 3.30-3.31 (m, 2H, CH$_2$), 3.45-3.47 (m, 2H, CH$_2$), 5.61 (d, J=9.7 Hz, 1H, CH), 6.04-6.10 (m, 1H, CH), 6.15-6.21 (m, 1H, CH), 7.20-7.25 (m, 2H, Ar—H, pyrimidine-NH), 7.62-7.65 (m, 1H, Ar—H), 7.75-7.76 (m, 2H, Ar—H), 7.88-7.94 (m, 2H, Ar—H), 7.96 (s, 1H, pyrimidine-H), 8.57 (s, 1H, NH), 9.41 (s, 1H, benzene ring-NH). LC-MS (m/z) 526 (M+1).

Example 53

Preparation of t-butyl ester of 3-(4-cyano-3-fluorobenzamino)propylamino formic acid

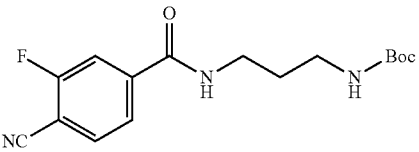 [SMILES: CC(C)(C)OC(=O)NCCCNC(=O)c1ccc(C#N)c(F)c1]

White solid of t-butyl ester of 3-(4-cyano-3-fluorobenzamino)propylamino formic acid (462 mg, yield of 71.9%) was prepared from t-butyl ester of 3-aminopropyl t-butylamino formic acid (348 mg, 2.0 mmol) and 4-cyano-3-fluobenzoic acid (330 mg, 2.0 mmol) based on the similar steps according to Example 4. LC-MS (m/z) 322 (M+1).

Example 54

Preparation of N-(3-aminopropyl)-4-cyano-3-fluorobenzamide

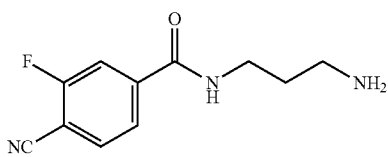 [SMILES: N#Cc1ccc(C(=O)NCCCN)cc1F]

White solid of N-(3-aminopropyl)-4-cyano-3-fluorobenzamide (275 mg, yield of 86.5%) was prepared from t-butyl ester of 3-(4-cyano-3-fluorobenzamino)propylamino formic acid (462 mg, 1.44 mmol) based on the similar steps according to Example 5. LC-MS (m/z) 222 (M+1).

Example 55

Preparation of 4-cyano-N-(3-(2,5-dichloropyrimidinyl-4-amino)propyl)-3-fluorobenzamide

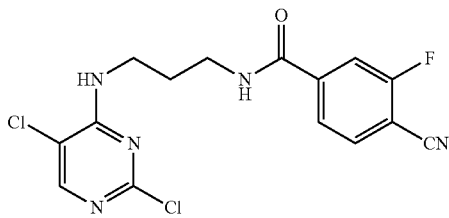 [SMILES: N#Cc1ccc(C(=O)NCCCNc2nc(Cl)ncc2Cl)cc1F]

White solid of 4-cyano-N-(3-(2,5-dichloropyrimidinyl-4-amino)propyl)-4-fluorobenzamide (340 mg, yield of 74.6%) was prepared from 2,4,5-trichloropyrimidine (229 mg, 1.25 mmol) and N-(3-aminopropyl)-4-cyano-3-fluorobenzamide (275 mg, 1.24 mmol) based on the similar steps according to Example 6. LC-MS (m/z) 368 (M+1).

Example 56

Preparation of N-(3-(5-chloro-2-(4-fluoro-3-(N-methylacrylamido)phenylamino)pyrimidinyl-4-amino)propyl)-4-cyano-3-fluorobenzamide

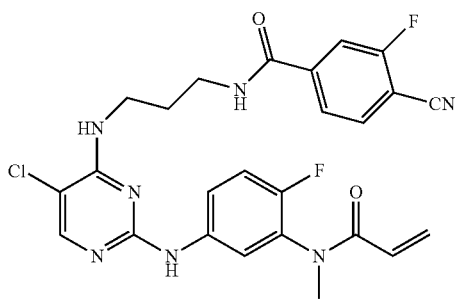 [SMILES: C=CC(=O)N(C)c1cc(Nc2ncc(Cl)c(NCCCNC(=O)c3ccc(C#N)c(F)c3)n2)ccc1F]

White solid of N-(3-(5-chloro-2-(4-fluoro-3-(N-methylacrylamido)phenylamino)pyrimidinyl-4-amino)propyl)-4-cyano-3-fluorobenzamide (98 mg, yield of 45.6%) was prepared from 4-cyano-N-(3-(2,5-dichloropyrimidinyl-4-amino)propyl)-3-fluorobenzamide (150 mg, 0.41 mmol) and N-(5-amino-2-fluorophenyl)-N-methylacrylamide (87 mg, 0.45 mmol) based on the similar steps according to Example 7. $^1$H-NMR (DMSO-d$_6$) δ 1.81-1.84 (m, 2H, CH$_2$), 3.19 (s, 3H, CH$_3$), 3.33-3.35 (m, 2H, CH$_2$), 3.45-3.46 (m, 2H, CH$_2$), 5.59 (d, J=9.7 Hz, 1H, CH), 6.02-6.09 (m, 1H, CH), 6.21-6.20 (m, 1H, CH), 7.21-7.25 (m, 2H, Ar—H, pyrimidine-NH), 7.63-7.65 (m, 1H, Ar—H), 7.81-7.89 (m, 2H, Ar—H), 7.95 (s, 1H, pyrimidine-H), 8.04-8.12 (m, 2H, Ar—H), 8.76 (t, J=5.6 Hz, 1H, NH), 9.45 (s, 1H, benzene ring-NH). LC-MS (m/z) 526 (M+1).

Example 57

Preparation of N-(3-(2-chloro-5-methylpyrimidinyl-4-amino)propyl)-4-cyanobenzamide

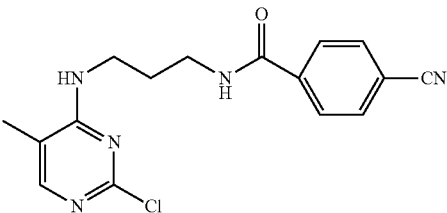 [SMILES: Cc1cnc(Cl)nc1NCCCNC(=O)c1ccc(C#N)cc1]

Yellow solid of N-(3-(2-chloro-5-methylpyrimidinyl-4-amino)propyl)-4-cyano-benzamide (100 mg, yield of 60.6%) was prepared from 2,4-dichloro-5-methylpyrimidine (82 mg, 0.5 mmol) and N-(3-aminopropyl)-4-cyano-benzamide (100 mg, 0.5 mmol) based on the similar steps according to Example 6. LC-MS (m/z) 330 (M+1).

Example 58

Preparation of 4-cyano-N-(3-(2-(4-fluoro-3-(N-methylacrylamido)phenylamino)-5-methylpyrimidinyl-4-amino)propyl)benzamide

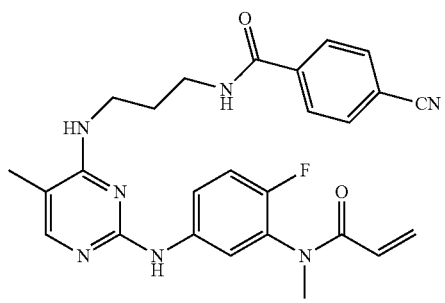 [SMILES: C=CC(=O)N(C)c1cc(Nc2ncc(C)c(NCCCNC(=O)c3ccc(C#N)cc3)n2)ccc1F]

Black solid of 4-cyano-N-(3-(2-(4-fluoro-3-(N-methylacrylamido)phenylamino)-5-methylpyrimidinyl-4-amino)propyl)-benzamide (10 mg, yield of 3.3%) was prepared from N-(3-(2-chloro-5-methylpyrimidinyl-4-amino)propyl)-4-cyano-benzamide (100 mg, 0.61 mmol) and N-(5-amino-2-fluorophenyl)-N-methylacrylamide (128 mg, 0.66 mmol) based on the similar steps according to Example 7. $^1$H-NMR (DMSO-d$_6$) δ 1.82-1.85 (m, 2H, CH$_2$), 1.92 (s, 3H, CH$_3$), 3.19 (s, 3H, CH$_3$), 3.35-3.37 (m, 2H, CH$_2$), 3.43-3.46 (m, 2H, CH$_2$), 5.59 (d, J=9.8 Hz, 1H, CH), 6.04-6.1 (m, 1H, CH), 6.15-6.20 (m, 1H, CH), 6.68 (t, J=5.5 Hz, 1H, Ar—H), 7.19 (t, J=9.5 Hz, 1H, pyrimidine-NH), 7.65-7.67 (m, 2H, Ar—H), 7.93-7.99 (m, 5H, Ar—H, pyrimidine-H), 8.69 (t, J=5.5 Hz, 1H, NH), 9.04 (s, 1H, benzene ring-NH). LC-MS (m/z) 488 (M+1).

Example 59

Preparation of N-(3-(2-chloro-5-fluoro-pyrimidinyl-4-amino)propyl)-4-cyano-benzamide

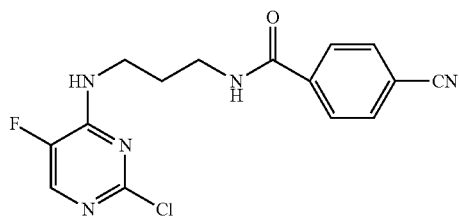 [SMILES: N#Cc1ccc(C(=O)NCCCNc2nc(Cl)ncc2F)cc1]

Yellow solid of N-(3-(2-chloro-5-fluoro-pyrimidinyl-4-amino)propyl)-4-cyano-benzamide (100 mg, yield of 60.0%) was prepared from 2,4-dichloro-5-fluoro-pyrimidine (83 mg, 0.5 mmol) and N-(3-aminopropyl)-4-cyano-benzamide (100 mg, 0.5 mmol) based on the similar steps according to Example 6. LC-MS (m/z) 334 (M+1).

Example 60

Preparation of 4-cyano-N-(3-(5-fluoro-2-(4-fluoro-3-(N-methylacrylamido)phenylamino)pyrimidinyl-4-amino)propyl)benzamide

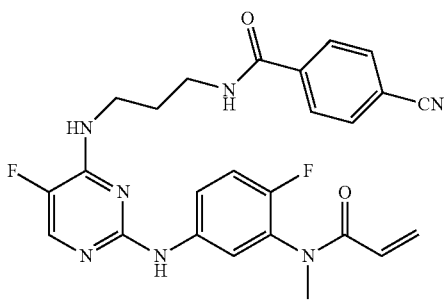 [SMILES: C=CC(=O)N(C)c1cc(Nc2ncc(F)c(NCCCNC(=O)c3ccc(C#N)cc3)n2)ccc1F]

Grey solid of 4-cyano-N-(3-(5-fluoro-2-(4-fluoro-3-(N-methylacrylamido)phenylamino)pyrimidinyl-4-amino)propyl)benzamide (49 mg, yield of 58.3%) was prepared from N-(3-(2-chloro-5-fluoropyrimidinyl-4-amino)propyl)-4-cyano-benzamide (100 mg, 0.30 mmol) and N-(5-amino-2-fluorophenyl)-N-methylacrylamide (110 mg, 0.56 mmol) based on the similar steps according to Example 7. $^1$H-NMR (DMSO-d$_6$) δ 1.84-1.85 (m, 2H, CH$_2$), 3.18 (s, 3H, CH$_3$), 3.33-3.35 (m, 2H, CH$_2$), 3.42-3.43 (m, 2H, CH$_2$), 5.59 (d, J=8.6 Hz, 1H, CH), 6.02-6.09 (m, 1H, CH), 6.15-6.20 (m, 1H, CH), 7.20 (t, J=9.1 Hz, 1H, pyrimidine-NH), 7.47-7.49 (m, 1H, Ar—H), 7.63-7.64 (m, 1H, Ar—H), 7.88-7.89 (m, 2H, Ar—H), 7.92-7.96 (m, 4H, pyrimidine-H, Ar—H), 8.68 (s, 1H, NH), 9.23 (s, 1H, benzene ring-NH). LC-MS (m/z) 492 (M+1).

Example 61

Preparation of t-butyl ester of 3-(2-(4-cyanophenyl)acetamino)propylamino formic acid

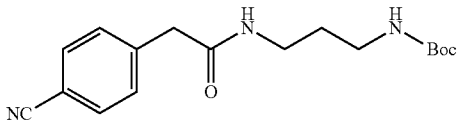 [SMILES: CC(C)(C)OC(=O)NCCCNC(=O)Cc1ccc(C#N)cc1]

White solid of t-butyl ester of 3-(2-(4-cyanophenyl)acetamino)propylamino formic acid (511 mg, yield of 80.6%) was prepared from t-butyl ester of 3-aminopropylamino formic acid (348 mg, 2.0 mmol) and 2-(4-cyano-phenyl) acetic acid (322 mg, 2.0 mmol) based on the similar steps according to Example 4. LC-MS (m/z) 318 (M+1).

Example 62

Preparation of N-(3-aminopropyl)-2-(4-cyanophenyl)acetamide

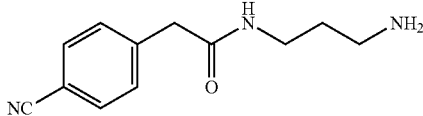 [SMILES: N#Cc1ccc(CC(=O)NCCCN)cc1]

White solid of N-(3-aminopropyl)-2-(4-cyanophenyl)acetamide (312 mg, yield of 89.4%) was prepared from t-butyl ester of 3-(2-(4-cyanophenyl)acetamino)propylamino formic acid (511 mg, 1.61 mmol) based on the similar steps according to Example 5. LC-MS (m/z) 218 (M+1).

Example 63

Preparation of 2-(4-cyanophenyl)-N-(3-(2,5-dichloropyrimidinyl-4-amino)propyl)acetamide

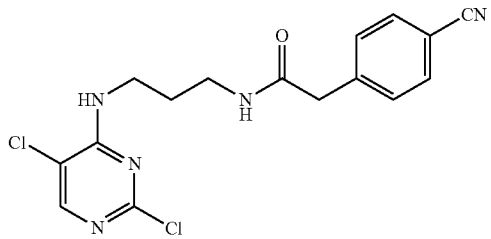 [SMILES: N#Cc1ccc(CC(=O)NCCCNc2nc(Cl)ncc2Cl)cc1]

White solid of 2-(4-cyanophenyl)-N-(3-(2,5-dichloropyrimidinyl-4-amino)propyl)acetamide (360 mg, yield of 68.9%) was prepared from 2,4,5-trichloropyrimidine (265 mg, 1.45 mmol) and N-(3-aminopropyl)-2-(4-cyanophenyl) acetamide (312 mg, 1.44 mmol) based on the similar steps according to Example 6. LC-MS (m/z) 364 (M+1).

Example 64

Preparation of N-(5-(5-chloro-4-(3-(2-(4-cyanophenyl)acetamino)propylamino)pyrimidinyl-2-amino)-2-fluorophenyl)-N-methylacrylamide

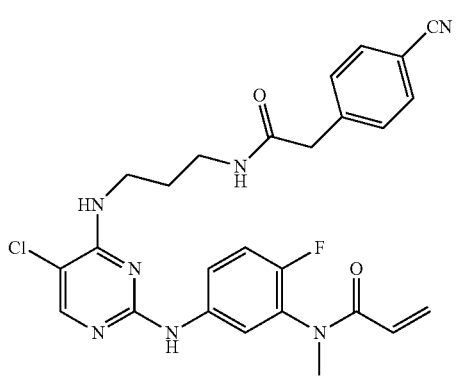 [SMILES: C=CC(=O)N(C)c1cc(Nc2ncc(Cl)c(NCCCNC(=O)Cc3ccc(C#N)cc3)n2)ccc1F]

White solid of N-(5-(5-chloro-4-(3-(2-(4-cyanophenyl)acetamino)propylamino)pyrimidinyl-2-amino)-2-fluorophenyl)-N-methylacrylamide (113 mg, yield of 53.1%) was prepared from 2-(4-cyanophenyl)-N-(3-(2,5-dichloropyrimidinyl-4-amino)propyl) acetamide (150 mg, 0.41 mmol) and N-(5-amino-2-fluorophenyl)-N-methylacrylamide (87 mg, 0.45 mmol) based on the similar steps according to Example 7. $^1$H-NMR (DMSO-d$_6$) δ 1.67-1.72 (m, 2H, CH$_2$), 3.08-3.11 (m, 2H, CH$_2$), 3.18 (s, 3H, CH$_3$), 3.37-3.38 (m, 2H, CH$_2$), 3.52 (s, 2H, CH$_2$), 5.60 (d, J=10.2 Hz, 1H, CH), 6.03-6.09 (m, 1H, CH), 6.16-6.21 (m, 1H, CH), 7.19-7.22 (m, 1H, Ar—H), 7.26 (t, J=9.3 Hz, 1H, pyrimidine-NH), 7.44 (d, J=8.1 Hz, 2H, Ar—H), 7.64-7.66 (m, 1H, Ar—H), 7.74 (d, J=8.2 Hz, 2H, Ar—H), 7.88-7.89 (m, 1H, Ar—H), 7.95 (s, 1H, pyrimidine-H), 8.13 (t, J=5.6 Hz, 1H, NH), 9.39 (s, 1H, benzene ring-NH). LC-MS (m/z) 522 (M+1).

Example 65

Preparation of t-butyl ester of 3-(4-cyano-phenylsulfonamino)propylamino formic acid

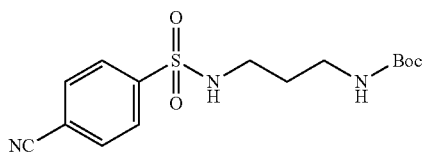 [SMILES: CC(C)(C)OC(=O)NCCCNS(=O)(=O)c1ccc(C#N)cc1]

White solid of t-butyl ester of 3-(4-cyano-phenylsulfonamino)propylamino formic acid (0.25 g, yield of 73.7%) was prepared as follows. 4-cyano-benzene sulfonyl chloride (0.2 g, 1.0 mmol) and N-Boc-1,3-propane diamine (0.18 g, 1.03 mmol) were dissolved in 5 ml THF and stirred at room temperature. Subsequently, DIPEA (0.26 g, 2.0 mmol) was added and reacted for 4 h. The reaction was monitored by LC-MS. After the reaction, saturated aqueous NaHCO$_3$ solution was added, and the mixture was stirred to precipitate the solid. The target intermediate was obtained by filtration. LC-MS (m/z) 340 (M+1).

Example 66

Preparation of N-(3-aminopropyl)-4-cyano phenylsulfonamide

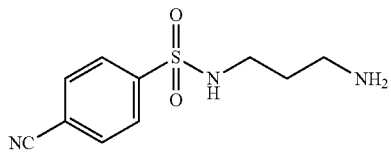 [SMILES: N#Cc1ccc(S(=O)(=O)NCCCN)cc1]

White solid of N-(3-aminopropyl)-4-cyano-phenylsulfonamide (150 mg, yield of 85.2%) was prepared from t-butyl ester of 3-(4-cyano-phenylsulfonamino)propylamino formic acid (250 mg, 0.74 mmol) based on the similar steps according to Example 5. LC-MS (m/z) 240 (M+1).

Example 67

Preparation of 4-cyano-N-(3-(2,5-dichloropyrimidinyl-4-amino)propyl)phenylsulfonamide

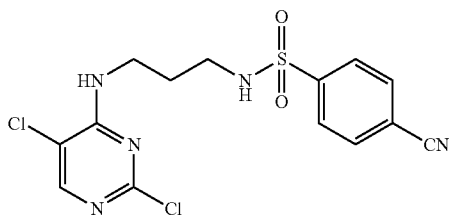 [SMILES: N#Cc1ccc(S(=O)(=O)NCCCNc2nc(Cl)ncc2Cl)cc1]

White solid of 4-cyano-N-(3-(2,5-dichloropyrimidinyl-4-amino)propyl)phenylsulfonamide (150 mg, yield of 61.9%) was prepared from 2,4,5-trichloropyrimidine (128 mg, 0.7 mmol) and N-(3-aminopropyl)-4-cyano-phenylsulfonamide (150 mg, 0.63 mmol) based on the similar steps according to Example 6. LC-MS (m/z) 386 (M+1).

Example 68

Preparation of 4-cyano-N-(3-(5-chloro-2-(4-fluoro-3-(N-methylacrylamido)phenylamino)pyrimidinyl-4-amino)propyl)benzenesulfonamide

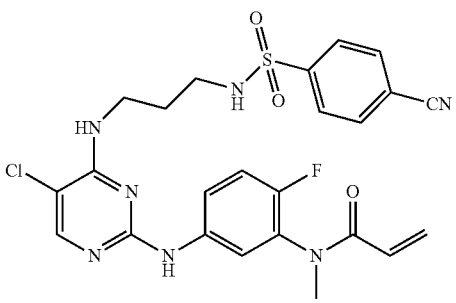 [SMILES: C=CC(=O)N(C)c1cc(Nc2ncc(Cl)c(NCCCNS(=O)(=O)c3ccc(C#N)cc3)n2)ccc1F]

White solid of N-(5-(5-chloro-4-(3-(4-cyano-phenylsulfonamino)propylamino)pyrimidinyl-2-amino)-2-fluorophenyl)-N-methylacrylamide (35 mg, yield of 30.7%) was prepared from 4-cyano-N-(3-(2,5-dichloropyrimidinyl-4-amino)propyl)phenylsulfonamide (80 mg, 0.21 mmol) and N-(5-amino-2-fluorophenyl)-N-methylacrylamide (43 mg, 0.22 mmol) based on the similar steps according to Example 7. $^1$H-NMR (DMSO-d$_6$) δ 1.63-1.70 (m, 2H, CH$_2$), 2.80-2.85 (m, 2H, CH$_2$), 3.17 (s, 3H, CH$_3$), 3.34-3.35 (m, 2H, CH$_2$), 5.60 (d, J=10.3 Hz, 1H, CH), 6.02-6.09 (m, 1H, CH), 6.15-6.20 (m, 1H, CH), 7.13-7.16 (m, 1H, Ar—H), 7.25 (t, J=9.4 Hz, 1H, pyrimidine-NH), 7.65-7.67 (m, 1H, Ar—H), 7.81-7.82 (m, 1H, Ar—H), 7.88 (t, J=5.9 Hz, 1H, NH), 7.91 (d, J=8.4 Hz, 2H, Ar—H), 7.94 (s, 1H, pyrimidine-H), 8.03 (d, J=8.4 Hz, 2H, Ar—H), 9.38 (s, 1H, benzene ring-NH). LC-MS (m/z) 544 (M+1).

Example 69

Preparation of 4-cyano-N-(3-hydroxypropyl)benzamide

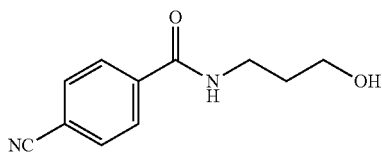 [SMILES: N#Cc1ccc(C(=O)NCCCO)cc1]

Yellow liquid of 4-cyano-N-(3-hydroxypropyl)benzamide (400 mg, yield of 99%) was prepared from 3-amino-1-propanol (150 mg, 2 mmol) and 4-cyanobenzoic acid (294 mg, 2 mmol) based on the similar steps according to Example 4. LC-MS (m/z) 205 (M+1).

Example 70

Preparation of 4-cyano-N-(3-(2,5-dichloropyrimidinyl-4-oxo)propyl)benzamide

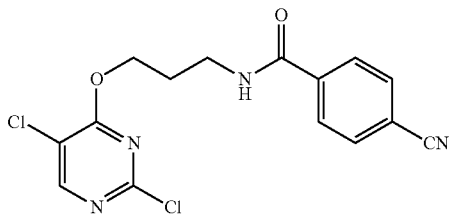 [SMILES: N#Cc1ccc(C(=O)NCCCOc2nc(Cl)ncc2Cl)cc1]

Yellow solid of 4-cyano-N-(3-(2,5-dichloropyrimidinyl-4-oxo)propyl)benzamide (120 mg, yield of 17%) was prepared as follows. 4-cyano-N-(3-hydroxypropyl)benzamide (408 mg, 2 mmol) was dissolved in 3 ml DMF and stirred in an ice bath. After 10 min, NaH (48 mg, 2 mmol) was added, and the mixture was kept stirring. 10 min later, 2,4,5-trichloropyrimidine (366 mg, 2 mmol) was added, and the mixture was taken out of the ice bath and reacted at room temperature. The reaction was monitored by LC-MS. After the reaction, the mixture was poured into 200 ml brine to precipitate yellow viscous substance. The water layer was then decanted, and 200 mL PE was added. Subsequently, the mixture was subjected to ultrasound. The target intermediate was obtained by filtration. LC-MS (m/z) 351 (M+1).

Example 71

Preparation of N-(3-(5-chloro-2-(4-fluoro-3-(N-methylacrylamido)phenylamino)pyrimidinyl-4-oxo) propyl)-4-cyano-benzamide

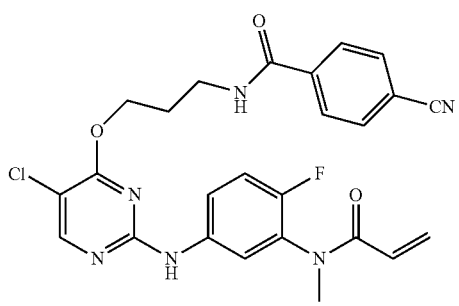 [SMILES: C=CC(=O)N(C)c1cc(Nc2ncc(Cl)c(OCCCNC(=O)c3ccc(C#N)cc3)n2)ccc1F]

Brown solid of N-(3-(5-chloro-2-(4-fluoro-3-(N-methylacrylamido)phenylamino)pyrimidinyl-4-oxo)propyl)-4-cyano-benzamide (20 mg, yield of 20.0%) was prepared from 4-cyano-N-(3-(2,5-dichloropyrimidinyl-4-oxo)propyl)benzamide (70 mg, 0.2 mmol) and N-(5-amino-2-fluorophenyl)-N-methylacrylamide (50 mg, 0.24 mmol) based on the similar steps according to Example 7. $^1$H-NMR (DMSO-d$_6$) δ 1.98-2.06 (m, 2H, CH$_2$), 3.18 (s, 3H, CH$_3$), 3.40-3.47 (m, 2H, CH$_2$), 4.45-4.51 (m, 2H, CH$_2$), 5.60 (d, J=9.5 Hz, 1H, CH), 6.03-6.09 (m, 1H, CH), 6.16-6.21 (m, 1H, CH), 7.28 (t, J=9.4 Hz, 1H, pyrimidine-NH), 7.64-7.67 (m, 1H, Ar—H), 7.78-7.80 (m, 1H, Ar—H), 7.93 (d, J=8.3 Hz, 2H, Ar—H), 7.98 (d, J=8.3 Hz, 2H, Ar—H), 8.32 (s, 1H, pyrimidine-H), 8.77 (t, J=5.3 Hz, 1H, NH), 9.85 (s, 1H, benzene ring-NH). LC-MS (m/z) 509 (M+1).

Example 72

Preparation of t-butyl ester of 3-(isonicotinamino)propylamino formic acid

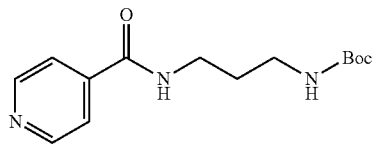 [SMILES: CC(C)(C)OC(=O)NCCCNC(=O)c1ccncc1]

White solid of t-butyl ester of 3-(isonicotinamino)propylamino formic acid (1.0 g, yield of 78.0%) was prepared from t-butyl ester of 3-aminopropylamino formic acid (800 mg, 4.60 mmol) and isonicotinoyl chloride (900 mg, 6.38 mmol) based on the similar steps according to Example 4. LC-MS (m/z) 280 (M+1).

Example 73

Preparation of N-(3-aminopropyl)-isonicotinamide

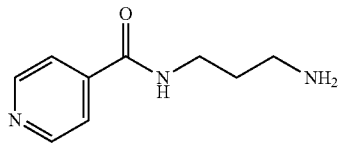 [SMILES: NCCCNC(=O)c1ccncc1]

White solid of N-(3-aminopropyl)-isonicotinamide (180 mg, yield of 28.1%) was prepared from t-butyl ester of 3-(isonicotinamino)propylamino formic acid (1.0 g, 3.58 mmol) based on the similar steps according to Example 5. LC-MS (m/z) 180 (M+1).

Example 74

Preparation of N-(3-(2,5-dichloropyrimidiny-4-amino)propyl)isonicotinamide

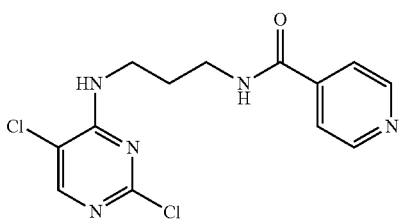 [SMILES: O=C(NCCCNc1nc(Cl)ncc1Cl)c1ccncc1]

White solid of N-(3-(2,5-dichloropyrimidinyl-4-amino)propyl)isonicotinamide (120 mg, yield of 32.8%) was prepared from 2,4,5-trichloropyrimidine (276 mg, 1.51 mmol) and N-(3-aminopropyl)-isonicotinamide (180 mg, 1.00 mmol) based on the similar steps according to Example 6. LC-MS (m/z) 326 (M+1).

Example 75

Preparation of N-(3-(5-chloro-2-(4-fluoro-3-(N-methylacrylamido)phenylamino)pyrimidinyl-4-amino)propyl)isonicotinamide

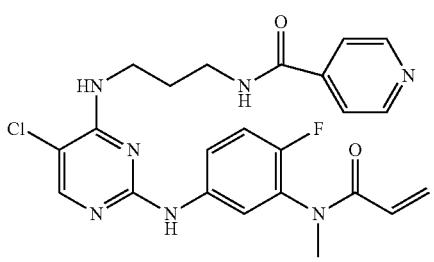 [SMILES: C=CC(=O)N(C)c1cc(Nc2ncc(Cl)c(NCCCNC(=O)c3ccncc3)n2)ccc1F]

White solid of N-(3-(5-chloro-2-(4-fluoro-3-(N-methylacrylamido)phenylamino)pyrimidinyl-4-amino)propyl) isonicotinamide (4.2 mg, yield of 2.3%) was prepared from N-(3-(2,5-dichloropyrimidinyl-4-amino)propyl)isonicotinamide (120 mg, 0.36 mmol) and N-(5-amino-2-fluorophenyl)-N-methylacrylamide (70 mg, 0.36 mmol) based on the similar steps according to Example 7. $^1$H-NMR (DMSO-$d_6$) δ 1.80-1.84 (m, 2H, CH$_2$), 3.19 (s, 3H, CH$_3$), 3.26-3.33 (m, 2H, CH$_2$), 3.45-3.47 (m, 2H, CH$_2$), 5.59 (d, J=10.1 Hz, 1H, CH), 6.03-6.09 (m, 1H, CH), 6.15-6.20 (m, 1H, CH), 7.23-7.27 (m, 2H, Ar—H, pyrimidine-NH), 7.64-7.66 (m, 1H, Ar—H), 7.72 (d, J=5.6 Hz, 2H, Ar—H), 7.89 (d, J=5.2 Hz, 1H, Ar—H), 7.96 (s, 1H, pyrimidine-H), 7.70 (d, J=5.5 Hz, 2H, Ar—H), 8.73 (s, 1H, NH), 9.40 (s, 1H, benzene ring-NH). LC-MS (m/z) 484 (M+1).

Example 76

Preparation of t-butyl ester of 3-(4-ethylphenylformamino)propylamino formic acid

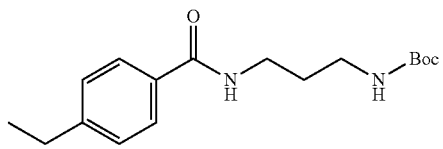 [SMILES: CCc1ccc(C(=O)NCCCNC(=O)OC(C)(C)C)cc1]

White solid of 3-(4-ethylbenzamino)propyl t-butyl carbamate (800 mg, yield of 91.1%) was prepared from t-butyl ester of 3-aminopropyl t-butylamino formic acid (500 mg, 2.87 mmol) and 4-ethylbenzoyl chloride (530 mg, 3.15 mmol) based on the similar steps according to Example 4. LC-MS (m/z) 307 (M+1).

Example 77

Preparation of N-(3-aminopropyl)-4-ethylbenzamide

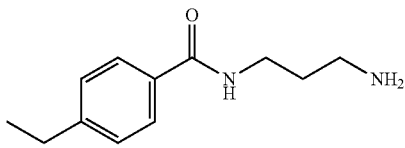

White solid of N-(3-aminopropyl)-4-ethylbenzamide (300 mg, yield of 55.7%) was prepared from t-butyl ester of 3-(4-ethylbenzamino)propylamino formic acid (800 mg, 2.61 mmol) based on the similar steps according to Example 5. LC-MS (m/z) 207 (M+1).

Example 78

Preparation of N-(3-(2,5-dichloropyrimidinyl-4-amino)propyl)-4-ethylbenzamide

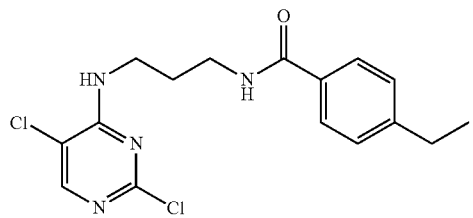 [SMILES: CCc1ccc(C(=O)NCCCNc2nc(Cl)ncc2Cl)cc1]

White solid of N-(3-(2,5-dichloropyrimidinyl-4-amino) propyl)-4-ethylbenzamide (500 mg, yield of 97.5%) was prepared from 2,4,5-trichloropyrimidine (300 mg, 1.64 mmol) and N-(3-aminopropyl)-4-ethylbenzamide (300 mg, 1.46 mmol) based on the similar steps according to Example 6. LC-MS (m/z) 353 (M+1).

Example 79

Preparation of N-(3-(5-chloro-2-(4-fluoro-3-(N-methylacrylamido)phenylamino)pyrimidinyl-4-amino)propyl)-4-ethylbenzamide

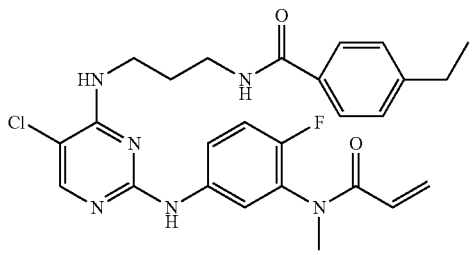 [SMILES: C=CC(=O)N(C)c1cc(Nc2ncc(Cl)c(NCCCNC(=O)c3ccc(CC)cc3)n2)ccc1F]

White solid of N-(3-(5-chloro-2-(4-fluoro-3-(N-methylacrylamido)phenylamino)pyrimidinyl-4-amino)propyl)-4-ethylbenzamide (86 mg, yield of 59.4%) was prepared from N-(3-(2,5-dichloropyrimidinyl-4-amino)propyl)-4-hydroxybenzamide (100 mg, 0.28 mmol) and N-(5-amino-2-fluorophenyl)-N-methylacrylamide (71 mg, 0.37 mmol) based on the similar steps according to Example 7. $^1$H-NMR (DMSO-$d_6$) δ 1.19 (t, J=7.6 Hz, 3H, $CH_3$), 1.78-1.81 (m, 2H, $CH_2$), 2.62-2.67 (m, 2H, $CH_2$), 3.19 (s, 3H, $CH_3$), 3.30-3.33 (m, 2H, $CH_2$), 3.44-3.45 (m, 2H, $CH_2$), 5.59 (d, J=10.1 Hz, 1H, CH), 6.03-6.09 (m, 1H, CH), 6.16-6.21 (m, 1H, CH), 7.22-7.29 (m, 4H, Ar—H, pyrimidine-NH), 7.65-7.67 (m, 1H, Ar—H), 7.76 (m, J=8.0 Hz, 2H, Ar—H), 7.89 (d, J=5.2 Hz, 1H, Ar—H), 7.96 (s, 1H, pyrimidine-H), 8.37 (t, J=5.5 Hz, 1H, NH), 9.39 (s, 1H, benzene ring-NH). LC-MS (m/z) 511 (M+1).

Example 80

Preparation of t-butyl ester of 3-(4-methylbenzamino)propylamino formic acid

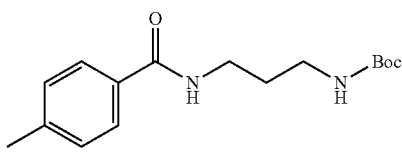 [SMILES: Cc1ccc(C(=O)NCCCNC(=O)OC(C)(C)C)cc1]

White solid of t-butyl ester of 3-(4-methylbenzamino) propylamino formic acid (0.45 g, yield of 79%) was prepared from t-butyl ester of 3-aminopropylamino formic acid (0.3 g, 1.95 mmol) and 4-methylbenzoyl chloride (0.34 g, 1.95 mmol) based on the similar steps according to Example 76. LC-MS (m/z) 293 (M+1).

Example 81

Preparation of N-(3-aminopropyl)-4-methylbenzamide

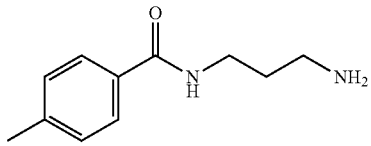

White solid of N-(3-aminopropyl)-4-methylbenzamide (290 mg, yield of 99%) was prepared from t-butyl ester of 3-(4-methylbenzamino)propylamino formic acid (450 mg, 1.54 mmol) based on the similar steps according to Example 5. LC-MS (m/z) 193 (M+1).

Example 82

Preparation of N-(3-(2,5-dichloropyrimidinyl-4-amino)propyl)-4-methylbenzamide

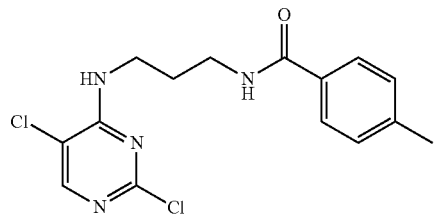 [SMILES: Cc1ccc(C(=O)NCCCNc2nc(Cl)ncc2Cl)cc1]

White solid of N-(3-(2,5-dichloropyrimidinyl-4-amino) propyl)-4-methylbenzamide (400 mg, yield of 78.1%) was prepared from 2,4,5-trichloropyrimidine (300 mg, 1.64 mmol) and N-(3-aminopropyl)-4-methylbenzamide (290 mg, 1.51 mmol) based on the similar steps according to Example 6. LC-MS (m/z) 339 (M+1).

Example 83

Preparation of N-(3-(5-chloro-2-(4-fluoro-3-(N-methylacrylamido)phenylamino)pyrimidinyl-4-amino)propyl)-4-methylbenzamide

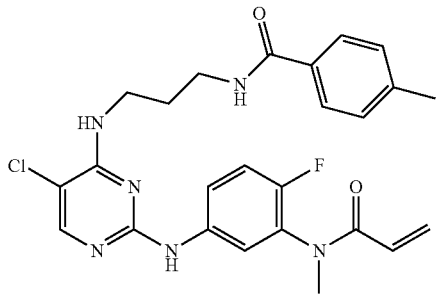 [SMILES: C=CC(=O)N(C)c1cc(Nc2ncc(Cl)c(NCCCNC(=O)c3ccc(C)cc3)n2)ccc1F]

White solid of N-(3-(5-chloro-2-(4-fluoro-3-(N-methylacrylamido)phenylamino)pyrimidinyl-4-amino)propyl)-4-methylbenzamide (200 mg, yield of 34.2%) was prepared from N-(3-(2,5-dichloropyrimidinyl-4-amino)propyl)-4-methylbenzamide (400 mg, 1.18 mmol) and N-(5-amino-2-fluorophenyl)-N-methylacrylamide (400 mg, 2.06 mmol) based on the similar steps according to Example 7. $^1$H-NMR (DMSO-d$_6$) δ 1.76-1.83 (m, 2H, CH$_2$), 2.34 (s, 3H, CH$_3$), 3.19 (s, 3H, CH$_3$), 3.29-3.33 (m, 2H, CH$_2$), 3.44-3.45 (m, 2H, CH$_2$), 5.59 (d, J=9.7 Hz, 1H, CH), 6.03-6.10 (m, 1H, CH), 6.16-6.21 (m, 1H, CH), 7.22-7.26 (m, 4H, Ar—H, pyrimidine-NH), 7.65-7.67 (m, 1H, Ar—H), 7.74 (d, J=8.0 Hz, 2H, Ar—H), 7.89 (d, J=5.2 Hz, 1H, Ar—H), 7.96 (s, 1H, pyrimidine-H), 8.38 (t, J=5.4 Hz, 1H, NH), 9.40 (s, 1H, benzene ring-NH). LC-MS (m/z) 497 (M+1).

Example 84

Preparation of t-butyl ester of 3-benzamidopropylamino formic acid

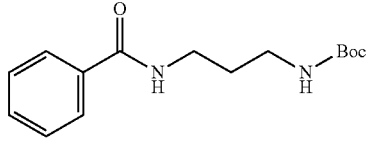 [SMILES: CC(C)(C)OC(=O)NCCCNC(=O)c1ccccc1]

White solid of t-butyl ester of 3-benzamidopropylamino formic acid (700 mg, yield of 88.3%) was prepared from t-butyl ester of 3-aminopropylamino formic acid (400 mg, 2.85 mmol) and benzoyl chloride (500 mg, 3.57 mmol) based on the similar steps according to Example 76. LC-MS (m/z) 279 (M+1).

Example 85

Preparation of N-(3-aminopropyl)benzamide

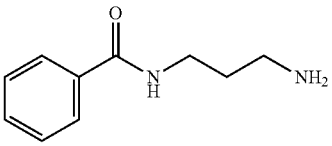 [SMILES: NCCCNC(=O)c1ccccc1]

White solid of t-butyl ester of N-(3-aminopropyl)benzamide (375 mg, yield of 80.4%) was prepared from 3-benzamidopropylamino formic acid (700 mg, 2.62 mmol) based on the similar steps according to Example 5. LC-MS (m/z) 179 (M+1).

Example 86

Preparation of N-(3-(2,5-dichloropyrimidiny-4-amino)propyl)benzamide

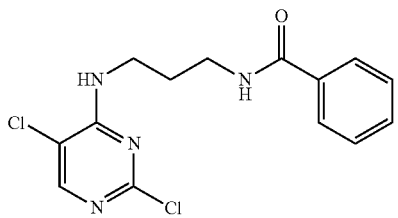 [SMILES: O=C(NCCCNc1nc(Cl)ncc1Cl)c1ccccc1]

White solid of N-(3-(2,5-dichloropyrimidinyl-4-amino)propyl)benzamide (556 mg, yield of 81.7%) was prepared from 2,4,5-trichloropyrimidine (550 mg, 3.00 mmol) and N-(3-aminopropyl)benzamide (375 mg, 2.1 mmol) based on the similar steps according to Example 6. LC-MS (m/z) 325 (M+1).

Example 87

Preparation of N-(3-(5-chloro-2-(4-fluoro-3-(N-methylacrylamido)phenylamino)pyrimidinyl-4-amino)propyl)benzamide

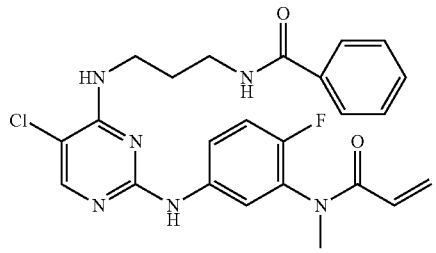 [SMILES: C=CC(=O)N(C)c1cc(Nc2ncc(Cl)c(NCCCNC(=O)c3ccccc3)n2)ccc1F]

White solid of N-(3-(5-chloro-2-(4-fluoro-3-(N-methylacrylamido)phenylamino)pyrimidinyl-4-amino)propyl)benzamide (245 mg, yield of 42.8%) was prepared from N-(3-(2,5-dichloropyrimidinyl-4-amino)benzamide (400 mg, 1.23 mmol) and N-(5-amino-2-fluorophenyl)-N-methylacrylamide (280 mg, 1.44 mmol) based on the similar steps according to Example 7. $^1$H-NMR (DMSO-d$_6$) δ 1.79-1.83 (m, 2H, CH$_2$), 3.19 (s, 3H, CH$_3$), 3.31-3.34 (m, 2H, CH$_2$), 3.44-3.46 (m, 2H, CH$_2$), 5.59 (d, J=9.8 Hz, 1H, CH), 6.03-6.09 (m, 1H, CH), 6.16-6.21 (m, 1H, CH), 7.22-7.27 (m, 2H, Ar—H, pyrimidine-NH), 7.45 (d, J=7.5 Hz, 2H, Ar—H), 7.52 (t, J=7.1 Hz, 1H, Ar—H), 7.65-7.67 (m, 1H, Ar—H), 7.83 (d, J=5.2 Hz, 2H, Ar—H), 7.89 (d, J=7.4 Hz, 1H, Ar—H), 7.96 (s, 1H, pyrimidine-H), 8.46 (t, J=5.2 Hz, 1H, NH), 9.40 (s, 1H, benzene ring-NH). LC-MS (m/z) 483 (M+1).

Example 88

Preparation of t-butyl ester of 3-(3-trifluoromethylbenzamino)propylamino formic acid

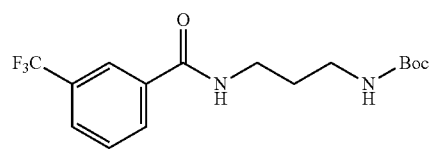 [SMILES: CC(C)(C)OC(=O)NCCCNC(=O)c1cccc(C(F)(F)F)c1]

White solid of t-butyl ester of 3-(3-trifluoromethylbenzamino)propylamino formic acid (640 mg, yield of 79.7%) was prepared from t-butyl ester of 3-aminopropylamino formic acid (400 mg, 2.32 mmol) and 3-trifluoromethyl benzoyl chloride (596 mg, 2.87 mmol) based on the similar steps according to Example 76. LC-MS (m/z) 347 (M+1).

Example 89

Preparation of
N-(3-aminopropyl)-3-trifluoromethylbenzamide

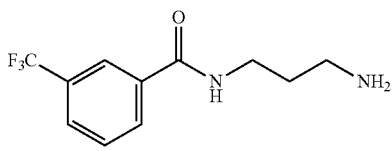 [SMILES: NCCCNC(=O)c1cccc(C(F)(F)F)c1]

White solid of N-(3-aminopropyl)-3-trifluoromethylbenzamide (300 mg, yield of 66.0%) was prepared from t-butyl ester of 3-(3-trifluoromethylbenzamino)propylamino formic acid (640 mg, 1.84 mmol) based on the similar steps according to Example 5. LC-MS (m/z) 247 (M+1).

Example 90

Preparation of N-(3-(2,5-dichloropyrimidinyl-4-amino)propyl)-3-trifluoromethylbenzamide

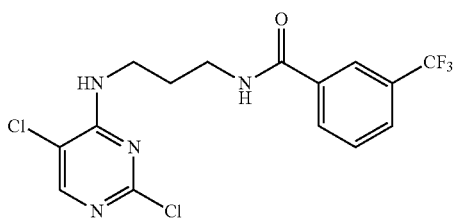 [SMILES: O=C(NCCCNc1nc(Cl)ncc1Cl)c1cccc(C(F)(F)F)c1]

White solid of N-(3-(2,5-dichloropyrimidinyl-4-amino)propyl)-3-trifluoromethylbenzamide (480 mg, yield of 93.2%) was prepared from 2,4,5-trichloropyrimidine (360 mg, 2.21 mmol) and N-(3-aminopropyl)-3-trifluoromethylbenzamide (300 mg, 1.47 mmol) based on the similar steps according to Example 6. LC-MS (m/z) 393 (M+1).

Example 91

Preparation of N-(3-(5-chloro-2-(4-fluoro-3-(N-methylacrylamido)phenylamino)pyrimidinyl-4-amino)propyl)-3-trifluoromethylbenzamide

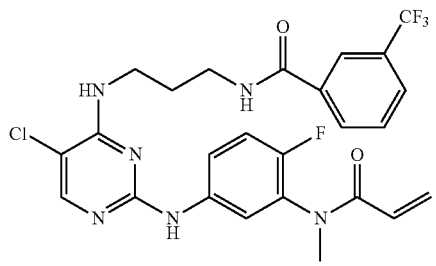 [SMILES: C=CC(=O)N(C)c1cc(Nc2ncc(Cl)c(NCCCNC(=O)c3cccc(C(F)(F)F)c3)n2)ccc1F]

White solid of N-(3-(5-chloro-2-(4-fluoro-3-(N-methylacrylamido)phenylamino)pyrimidinyl-4-amino)propyl)-3-trifluoromethylbenzamide (240 mg, yield of 35.7%) was prepared from N-(3-(2,5-dichloropyrimidinyl-4-amino)propyl)-3-trifluoromethylbenzamide (480 mg, 1.22 mmol) and N-(5-amino-2-fluorophenyl)-N-methylacrylamide (260 mg, 1.34 mmol) based on the similar steps according to Example 7. $^1$H-NMR (DMSO-$d_6$) δ 1.80-1.87 (m, 2H, CH$_2$), 3.19 (s, 3H, CH$_3$), 3.32-3.37 (m, 2H, CH$_2$), 3.44-3.48 (m, 2H, CH$_2$), 5.59 (d, J=9.6 Hz, 1H, CH), 6.03-6.09 (m, 1H, CH), 6.16-6.21 (m, 1H, CH), 7.21-7.25 (m, 2H, Ar—H, pyrimidine-NH), 7.65-7.67 (m, 1H, Ar—H), 7.71 (t, J=7.8 Hz, 1H, Ar—H), 7.88-7.90 (m, 2H, Ar—H), 7.96 (s, 1H, pyrimidine-H), 8.14 (d, J=7.9 Hz, 1H, Ar—H), 8.16 (s, 1H, Ar—H), 8.72 (t, J=5.4 Hz, 1H, NH), 9.40 (s, 1H, benzene ring-NH). LC-MS (m/z) 551 (M+1).

Example 92

Preparation of t-butyl ester of
3-(3-cyano-benzamino)propylamino formic acid

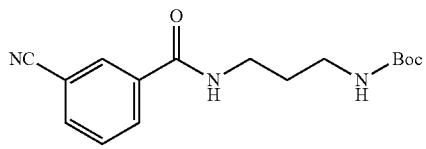 [SMILES: CC(C)(C)OC(=O)NCCCNC(=O)c1cccc(C#N)c1]

White solid of t-butyl ester of 3-(3-cyano-benzamino)propylamino formic acid (740 mg, yield of 80.6%) was prepared from t-butyl ester of 3-aminopropylamino formic acid (600 mg, 3.44 mmol) and 3-cyano-benzoyl chloride (500 mg, 3.02 mmol) based on the similar steps according to Example 76. LC-MS (m/z) 304 (M+1).

Example 93

Preparation of
N-(3-aminopropyl)-3-cyanobenzamide

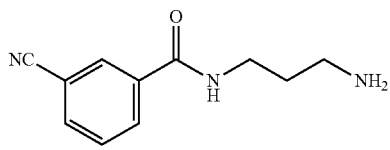 [SMILES: N#Cc1cccc(C(=O)NCCCN)c1]

White solid of N-(3-aminopropyl)-3-cyanobenzamide (300 mg, yield of 86.5%) was prepared from t-butyl ester of 3-(3-cyano-benzamino)propylamino formic acid (740 mg, 2.62 mmol) based on the similar steps according to Example 5. LC-MS (m/z) 204 (M+1).

Example 94

Preparation of N-(3-(2,5-dichloropyrimidinyl-4-amino)propyl)-3-cyanobenzamide

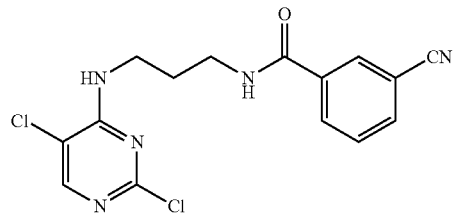 [SMILES: N#Cc1cccc(C(=O)NCCCNc2nc(Cl)ncc2Cl)c1]

White solid of N-(3-(2,5-dichloropyrimidinyl-4-amino)propyl)-3-cyanobenzamide (460 mg, yield of 89.4%) was prepared from 2,4,5-trichloropyrimidine (360 mg, 2.21 mmol) and N-(3-aminopropyl)-3-cyanobenzamide (300 mg, 1.47 mmol) based on the similar steps according to Example 6. LC-MS (m/z) 350 (M+1).

Example 95

Preparation of N-(3-(5-chloro-2-(4-fluoro-3-(N-methylacrylamido)phenylamino)pyrimidinyl-4-amino)propyl)-3-cyanobenzamide

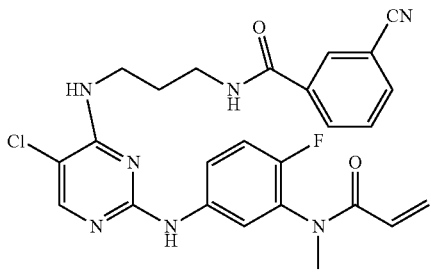 [SMILES: C=CC(=O)N(C)c1cc(Nc2ncc(Cl)c(NCCCNC(=O)c3cccc(C#N)c3)n2)ccc1F]

White solid of N-(3-(5-chloro-2-(4-fluoro-3-(N-methylacrylamido)phenylamino)pyrimidinyl-4-amino)propyl)-3-cyanobenzamide (210 mg, yield of 31.8%) was prepared from N-(3-(2,5-dichloropyrimidinyl-4-amino)propyl)-3-cyanobenzamide (460 mg, 1.31 mmol) and N-(5-amino-2-fluorophenyl)-N-methylacrylamide (280 mg, 1.44 mmol) based on the similar steps according to Example 7. $^1$H-NMR (DMSO-d$_6$) δ 1.80-1.86 (m, 2H, CH$_2$), 3.19 (s, 3H, CH$_3$), 3.31-3.35 (m, 2H, CH$_2$), 3.44-3.48 (m, 2H, CH$_2$), 5.59 (d, J=10.2 Hz, 1H, CH), 6.03-6.09 (m, 1H, CH), 6.16-6.21 (m, 1H, CH), 7.21-7.26 (m, 2H, Ar—H, pyrimidine-NH), 7.64-7.66 (m, 1H, Ar—H), 7.68-7.70 (m, 1H, Ar—H), 7.89-7.90 (m, 1H, Ar—H), 7.96 (s, 1H, pyrimidine-H), 7.98 (d, J=7.7 Hz, 1H, Ar—H), 8.13 (d, J=7.9 Hz, 1H, Ar—H), 8.24 (s, 1H, Ar—H), 8.66 (t, J=5.7 Hz, 1H, NH), 9.40 (s, 1H, benzene ring-NH). LC-MS (m/z) 508 (M+1).

Example 100

Preparation of t-butyl ester of 3-(3-fluoro-4-trifluoromethyl benzamino)propylamino formic acid

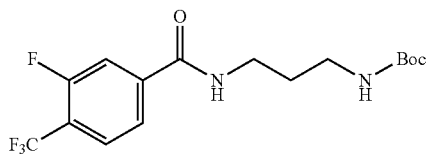 [SMILES: CC(C)(C)OC(=O)NCCCNC(=O)c1ccc(C(F)(F)F)c(F)c1]

Yellow solid of t-butyl ester of 3-(3-fluoro-4-trifluoromethylbenzamino)propylamino formic acid (728 mg, yield of 100%) was prepared from t-butyl ester of 3-aminopropylamino formic acid (348 mg, 2 mmol) and 3-fluoro-4-trifluoromethylbenzoic acid (416 mg, 2 mmol) based on the similar steps according to Example 4. LC-MS (m/z) 365 (M+1).

Example 101

Preparation of N-(3-aminopropyl)-3-fluoro-4-trifluoromethylbenzamide

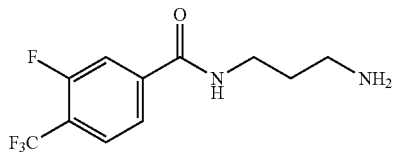 [SMILES: NCCCNC(=O)c1ccc(C(F)(F)F)c(F)c1]

White solid of N-(3-aminopropyl)-3-fluoro-4-trifluoromethylbenzamide (264 mg, yield of 50%) was prepared from t-butyl ester of 3-(3-fluoro-4-trifluoromethylbenzamino)propylamino formic acid (728 mg, 2 mmol) based on the similar steps according to Example 5. LC-MS (m/z) 265 (M+1).

Example 102

Preparation of N-(3-(2,5-dichloropyrimidinyl-4-amino)propyl)-3-fluoro-4-trifluoromethylbenzamide

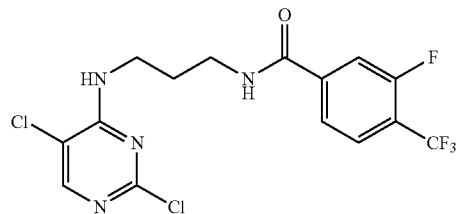 [SMILES: O=C(NCCCNc1nc(Cl)ncc1Cl)c1ccc(C(F)(F)F)c(F)c1]

Yellow solid of N-(3-(2,5-dichloropyrimidinyl-4-amino)propyl)-3-fluoro-4-trifluoromethylbenzamide (200 mg, yield of 49%) was prepared from 2,4,5-trichloropyrimidine (183 mg, 1.00 mmol) and N-(3-aminopropyl)-3-fluoro-4-trifluoromethylbenzamide (264 mg, 1.00 mmol) based on the similar steps according to Example 6. LC-MS (m/z) 411 (M+1).

Example 103

Preparation of N-(3-(5-chloro-2-(4-fluoro-3-(N-methylacrylamido)phenylamino)pyrimidinyl-4-amino)propyl)-3-fluoro-4-trifluoromethylbenzamide

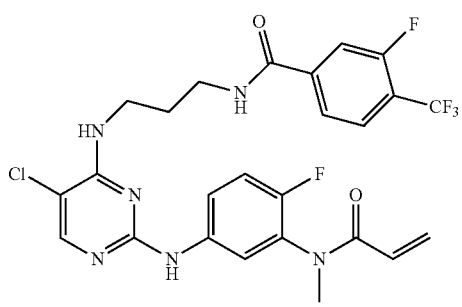 [SMILES: C=CC(=O)N(C)c1cc(Nc2ncc(Cl)c(NCCCNC(=O)c3ccc(C(F)(F)F)c(F)c3)n2)ccc1F]

White solid of N-(3-(5-chloro-2-(4-fluoro-3-(N-methylacrylamido)phenylamino)pyrimidinyl-4-amino)propyl)-3- fluoro-4-trifluoromethylbenzamide (50 mg, yield of 20%) was prepared from N-(3-(2,5-dichloropyrimidinyl-4-amino)propyl)-3-fluoro-4-trifluoromethylbenzamide (205 mg, 0.5 mmol) and N-(5-amino-2-fluorophenyl)-N-methylacrylamide (110 mg, 0.6 mmol) based on the similar steps according to Example 7. $^1$H-NMR (DMSO-$d_6$) δ 1.81-1.86 (m, 2H, CH$_2$), 3.19 (s, 3H, CH$_3$), 3.32-3.36 (m, 2H, CH$_2$), 3.45-3.47 (m, 2H, CH$_2$), 5.59 (d, J=9.4 Hz, 1H, CH), 6.02-6.09 (m, 1H, CH), 6.15-6.20 (m, 1H, CH), 7.20-7.24 (m, 2H, Ar—H, pyrimidine-NH), 7.64-7.66 (m, 1H, Ar—H), 7.83-7.92 (m, 4H, Ar—H), 7.96 (s, 1H, pyrimidine-H), 8.75 (t, J=5.2 Hz, 1H, NH), 9.40 (s, 1H, benzene ring-NH). LC-MS (m/z) 569 (M+1).

Example 104

Preparation of t-butyl ester of 3-(2,3,4,5-tetrafluorobenzamino)propylamino formic acid

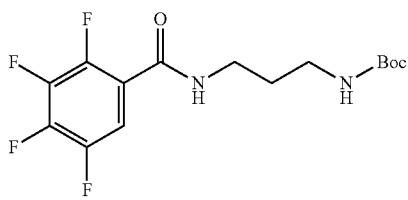 [SMILES: CC(C)(C)OC(=O)NCCCNC(=O)c1cc(F)c(F)c(F)c1F]

White solid of t-butyl ester of 3-(2,3,4,5-tetrafluorobenzamino)propylamino formic acid (400 mg, yield of 57.1%) was prepared from t-butyl ester of 3-aminopropylamino formic acid (348 mg, 2.00 mmol) and 2,3,4,5-tetrafluorobenzoyl chloride (848 mg, 4.00 mmol) based on the similar steps according to Example 76. LC-MS (m/z) 351 (M+1).

Example 105

Preparation of N-(3-aminopropyl)-2,3,4,5-tetrafluorobenzamide

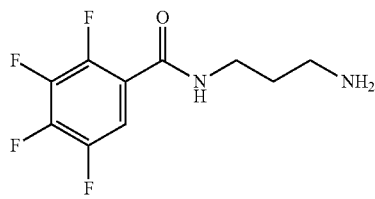 [SMILES: NCCCNC(=O)c1cc(F)c(F)c(F)c1F]

White solid of N-(3-aminopropyl)-2,3,4,5-tetrafluorobenzamide (250 mg, yield of 100%) was prepared from t-butyl ester of 3-(2,3,4,5-tetrafluorobenzamino)propylamino formic acid (350 mg, 1.00 mmol) based on the similar steps according to Example 5. LC-MS (m/z) 251 (M+1).

Example 106

Preparation of N-(3-(2,5-dichloropyrimidinyl-4-amino)propyl)-2,3,4,5-tetrafluorobenzamide

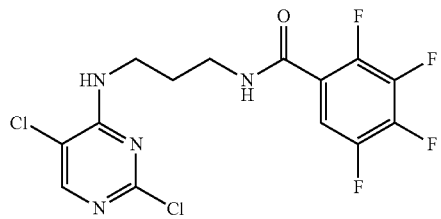 [SMILES: O=C(NCCCNc1nc(Cl)ncc1Cl)c1cc(F)c(F)c(F)c1F]

White solid of N-(3-(2,5-dichloropyrimidinyl-4-amino)propyl)-2,3,4,5-tetrafluorobenzamide (200 mg, yield of 50%) was prepared from 2,4,5-trichloropyrimidine (183 mg, 1.00 mmol) and N-(3-aminopropyl)-2,3,4,5-tetrafluorobenzamide (250 mg, 1.00 mmol) based on the similar steps according to Example 6. LC-MS (m/z) 397 (M+1).

Example 107

Preparation of N-(3-(5-chloro-2-(4-fluoro-3-(N-methylacrylamido)phenylamino)pyrimidinyl-4-amino)propyl)-2,3,4,5-tetrafluorobenzamide

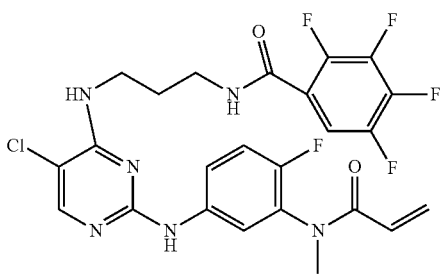 [SMILES: C=CC(=O)N(C)c1cc(Nc2ncc(Cl)c(NCCCNC(=O)c3cc(F)c(F)c(F)c3F)n2)ccc1F]

White solid of N-(3-(5-chloro-2-(4-fluoro-3-(N-methylacrylamido)phenylamino)pyrimidinyl-4-amino)propyl)-2,3,4,5-tetrafluorobenzamide (50 mg, yield of 18%) was prepared from N-(3-(2,5-dichloropyrimidinyl-4-amino)propyl)-2,3,4,5-tetrafluorobenzamide (200 mg, 0.5 mmol) and N-(5-amino-2-fluorophenyl)-N-methylacrylamide (110 mg, 0.6 mmol) based on the similar steps according to Example 7. $^1$H-NMR (DMSO-$d_6$) δ 1.79-1.82 (m, 2H, CH$_2$), 3.19 (s, 3H, CH$_3$), 3.28-3.30 (m, 2H, CH$_2$), 3.44-3.46 (m, 2H, CH$_2$), 5.60 (d, J=9.8 Hz, 1H, CH), 6.03-6.09 (m, 1H, CH), 6.16-6.21 (m, 1H, CH), 7.23-7.27 (m, 2H, Ar—H, pyrimidine-NH), 7.56-7.61 (m, 1H, Ar—H), 7.65-7.67 (m, 1H, Ar—H), 7.88 (d, J=5.4 Hz, 1H, Ar—H), 7.95 (s, 1H, pyrimidine-H), 8.52 (s, 1H, NH), 9.40 (s, 1H, benzene ring-NH). LC-MS (m/z) 555 (M+1).

Example 108

Preparation of t-butyl ester of 3-(4-acetylbenzamino)propylamino formic acid

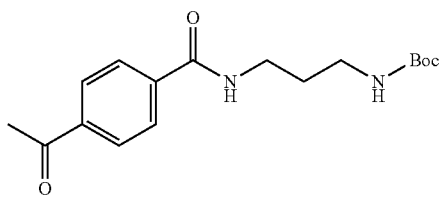 [SMILES: CC(=O)c1ccc(C(=O)NCCCNC(=O)OC(C)(C)C)cc1]

White solid of t-butyl ester of 3-(4-acetylbenzamino)propylamino formic acid (385 mg, yield of 60.2%) was prepared from t-butyl ester of 3-aminopropylamino formic acid (350 mg, 2.01 mmol) and 4-acetylbenzoic acid (328 mg, 2.00 mmol) based on the similar steps according to Example 4. LC-MS (m/z) 321 (M+1).

Example 109

Preparation of 4-acetyl-N-(3-aminopropyl)benzamide

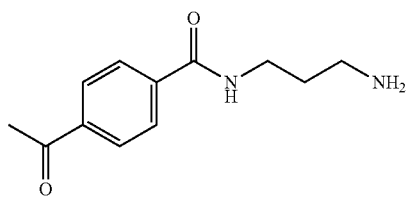 [SMILES: CC(=O)c1ccc(C(=O)NCCCN)cc1]

White solid of 4-acetyl-N-(3-aminopropyl)benzamide (200 mg, yield of 75.8%) was prepared from t-butyl ester of 3-(4-acetylbenzamino)propylamino formic acid (385 mg, 1.20 mmol) based on the similar steps according to Example 5. LC-MS (m/z) 221 (M+1).

Example 110

Preparation of 4-acetyl-N-(3-(2,5-dichloropyrimidinyl-4-amino)propyl)benzamide

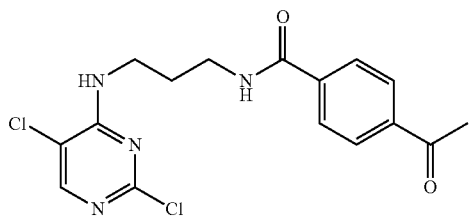 [SMILES: CC(=O)c1ccc(C(=O)NCCCNc2nc(Cl)ncc2Cl)cc1]

White solid of 4-acetyl-N-(3-(2,5-dichloropyrimidinyl-4-amino)propyl)benzamide (120 mg, yield of 36.1%) was prepared from 2,4,5-trichloropyrimidine (180 mg, 0.98 mmol) and 4-acetyl-N-(3-aminopropyl)benzamide (200 mg, 0.91 mmol) based on the similar steps according to Example 6. LC-MS (m/z) 367 (M+1).

Example 111

Preparation of 4-acetyl-N-(3-(5-chloro-2-(4-fluoro-3-(N-methylacrylamido)phenylamino)pyrimidinyl-4-amino)propyl)benzamide

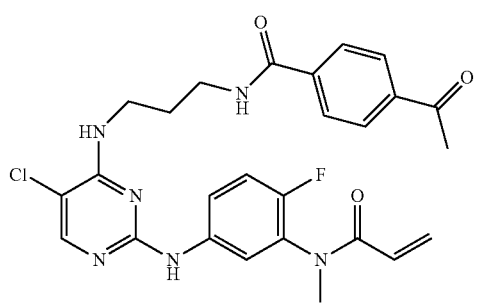 [SMILES: C=CC(=O)N(C)c1cc(Nc2ncc(Cl)c(NCCCNC(=O)c3ccc(C(C)=O)cc3)n2)ccc1F]

White solid of 4-acetyl-N-(3-(5-chloro-2-(4-fluoro-3-(N-methylacrylamido)phenylamino)pyrimidinyl-4-amino)propyl)benzamide (83 mg, yield of 47.9%) was prepared from 4-acetyl-N-(3-(2,5-dichloropyrimidinyl-4-amino)propyl)benzamide (120 mg, 0.33 mmol) and N-(5-amino-2-fluorophenyl)-N-methylacrylamide (70 mg, 0.36 mmol) based on the similar steps according to Example 7. $^1$H-NMR (DMSO-$d_6$) δ 1.79-1.85 (m, 2H, $CH_2$), 2.61 (s, 3H, $CH_3$), 3.19 (s, 3H, $CH_3$), 3.32-3.36 (m, 2H, $CH_2$), 3.45-3.48 (m, 2H, $CH_2$), 5.59 (d, J=9.9 Hz, 1H, CH), 6.02-6.09 (m, 1H, CH), 6.15-6.20 (m, 1H, CH), 7.21-7.28 (m, 2H, pyrimidine-NH, Ar—H), 7.64-7.69 (m, 1H, Ar—H), 7.88-7.89 (m, 1H, Ar—H), 7.94 (d, J=8.3 Hz, 2H, Ar—H), 7.96 (s, 1H, pyrimidine-H), 8.01 (d, J=8.4 Hz, 2H, Ar—H), 8.65 (t, J=5.3 Hz, 1H, NH), 9.40 (s, 1H, benzene ring-NH). LC-MS (m/z) 525 (M+1).

Example 112

Preparation of t-butyl ester of 3-(4-difluoromethylbenzamino)propylamino formic acid

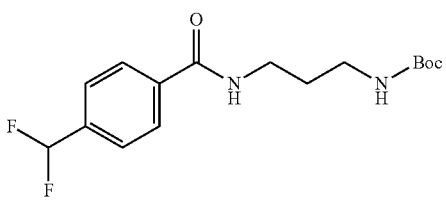 [SMILES: CC(C)(C)OC(=O)NCCCNC(=O)c1ccc(C(F)F)cc1]

White solid of t-butyl ester of 3-(4-difluoromethylbenzamino)propylamino formic acid (780 mg, yield of 84.3%) was prepared from t-butyl ester of 3-aminopropylamino formic acid (49 mg, 2.82 mmol) and 4-difluoromethylbenzoic acid (485 mg, 2.82 mmol) based on the similar steps according to Example 4. LC-MS (m/z) 329 (M+1).

Example 113

Preparation of N-(3-aminopropyl)-4-difluoromethylbenzamide

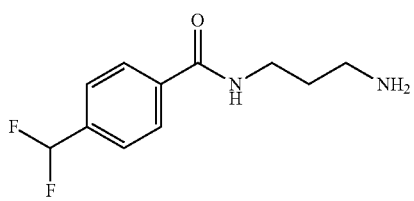 [SMILES: NCCCNC(=O)c1ccc(C(F)F)cc1]

White solid of N-(3-aminopropyl)-4-difluoromethylbenzamide (180 mg, yield of 33.2%) was prepared from t-butyl ester of 3-(4-difluoromethylbenzamino)propylamino formic acid (780 mg, 2.38 mmol) based on the similar steps according to Example 5. LC-MS (m/z) 229 (M+1).

Example 114

Preparation of N-(3-(2,5-dichloropyrimidinyl-4-amino)propyl)-4-difluoromethylbenzamide

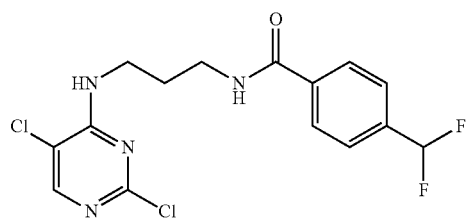 [SMILES: O=C(NCCCNc1nc(Cl)ncc1Cl)c1ccc(C(F)F)cc1]

White solid of N-(3-(2,5-dichloropyrimidinyl-4-amino)propyl)-4-difluoromethylbenzamide (250 mg, yield of 84.5%) was prepared from 2,4,5-trichloropyrimidine (180 mg, 0.98 mmol) and N-(3-aminopropyl)-4-difluoromethylbenzamide (180 mg, 0.79 mmol) based on the similar steps according to Example 6. LC-MS (m/z) 375 (M+1).

Example 115

Preparation of N-(3-(5-chloro-2-(4-fluoro-3-(N-methylacrylamido)phenylamino)pyrimidinyl-4-amino)propyl)-4-difluoromethylbenzamide

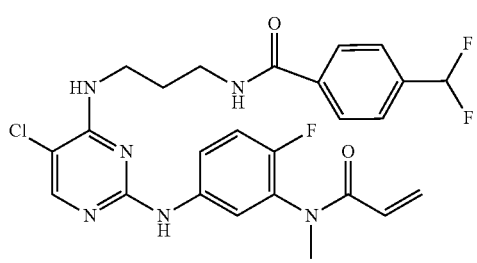 [SMILES: C=CC(=O)N(C)c1cc(Nc2ncc(Cl)c(NCCCNC(=O)c3ccc(C(F)F)cc3)n2)ccc1F]

White solid of N-(3-(5-chloro-2-(4-fluoro-3-(N-methylacrylamido)phenylamino)pyrimidinyl-4-amino)propyl)-4-difluoromethylbenzamide (26 mg, yield of 23.2%) was prepared from N-(3-(2,5-dichloropyrimidinyl-4-amino)propyl)-4-difluoromethylbenzamide (80 mg, 0.21 mmol) and N-(5-amino-2-fluorophenyl)-N-methylacrylamide (50 mg, 0.26 mmol) based on the similar steps according to Example 7. $^1$H-NMR (DMSO-d$_6$) δ 1.81-1.84 (m, 2H, CH$_2$), 3.19 (s, 3H, CH$_3$), 3.32-3.40 (m, 2H, CH$_2$), 3.45-3.47 (m, 2H, CH$_2$), 5.59 (d, J=9.4 Hz, 1H, CH), 6.03-6.09 (m, 1H, CH), 6.16-6.20 (m, 1H, CH), 6.94 (s, 0.4H, CHF$_2$), 7.08 (s, 0.6H, CHF$_2$), 7.22-7.26 (m, 2H, Ar—H, pyrimidine-NH), 7.64-7.66 (m, 3H, Ar—H), 7.89-7.90 (m, 1H, Ar—H), 7.95 (d, J=7.3 Hz, 2H, Ar—H), 7.96 (s, 1H, pyrimidine-H), 8.59 (s, 1H, NH), 9.40 (s, 1H, benzene ring-NH). LC-MS (m/z) 533 (M+1).

Example 120

Preparation of t-butyl ester of 6-(4-cyano-benzamino)hexylamino formic acid

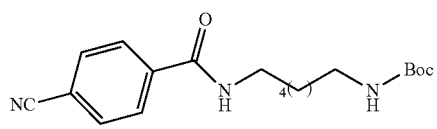

White solid of t-butyl ester of 6-(4-cyano-benzamino)hexylamino formic acid (1300 mg, yield of 73.4%) was prepared from t-butyl ester of 6-hexylamino formic acid (1100 mg, 5.09 mmol) and 4-cyano-benzoyl chloride (900 mg, 5.45 mmol) based on the similar steps according to Example 76. LC-MS (m/z) 346 (M+1).

Example 121

Preparation of N-(6-aminohexyl)-4-cyano-benzamide

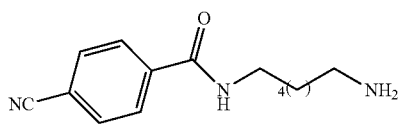

White solid of N-(6-aminohexyl)-4-cyano-benzamide (700 mg, yield of 75.6%) was prepared from t-butyl ester of 6-(4-cyano-benzamino)hexylamino formic acid (1300 mg, 3.76 mmol) based on the similar steps according to Example 5. LC-MS (m/z) 246 (M+1).

Example 122

Preparation of 4-cyano-N-(6-(2,5-dichloropyrimidinyl-4-amino)hexyl)benzamide

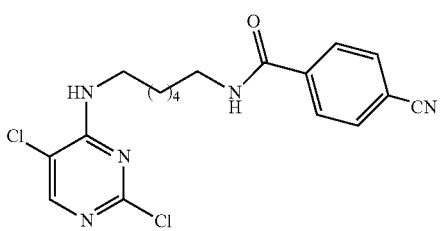

White solid of 4-cyano-N-(6-(2,5-dichloropyrimidinyl-4-amino)hexyl)benzamide (80 mg, yield of 49.7%) was prepared from 2,4,5-trichloropyrimidine (120 mg, 0.66 mmol) and N-(6-aminohexyl)-4-cyano-benzamide (100 mg, 0.41 mmol) based on the similar steps according to Example 6. LC-MS (m/z) 392 (M+1).

Example 123

Preparation of N-(6-(5-chloro-2-(4-fluoro-3-(N-methylacrylamido)phenylamino)pyrimidinyl-4-amino)hexyl)-4-cyanobenzamide

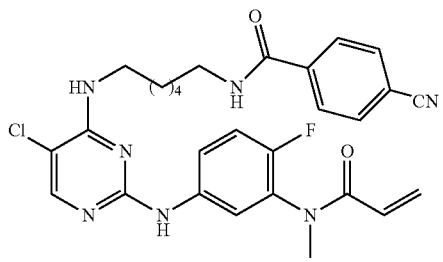

White solid of N-(6-(5-chloro-2-(4-fluoro-3-(N-methylacrylamido)phenylamino)pyrimidinyl-4-amino)hexyl)-4-cyano-benzamide (47 mg, yield of 50.3%) was prepared from 4-cyano-N-(6-(2,5-dichloropyrimidinyl-4-amino)hexyl)benzamide (68 mg, 0.17 mmol) and N-(5-amino-2-fluorophenyl)-N-methylacrylamide (46 mg, 0.24 mmol) based on the similar steps according to Example 7. $^1$H-NMR (DMSO-d$_6$) δ 1.30-1.32 (m, 4H, 2×CH$_2$), 1.52-1.56 (m, 4H, 2×CH$_2$), 3.19 (s, 3H, CH$_3$), 3.26-3.29 (m, 2H, CH$_2$), 3.36-3.37 (m, 2H, CH$_2$), 5.60 (d, J=9.9 Hz, 1H, CH), 6.03-6.10 (m, 1H, CH), 6.17-6.21 (m, 1H, CH), 7.22-7.27 (m, 2H, pyrimidine-NH, Ar—H), 7.59-7.61 (m, 1H, Ar—H), 7.93-7.98 (m, 6H, pyrimidine-NH, Ar—H), 8.64 (s, 1H, NH), 9.38 (s, 1H, benzene ring-NH). LC-MS (m/z) 550 (M+1).

In Vitro Biological Evaluation

These test methods are used for the in vitro activity evaluation of the compounds described herein, including in vitro enzymatic activity assay, cell growth activity assay, and intracellular activity assay.

These assays aim to comprehensively evaluate the properties of in vitro enzymatic inhibitory activity of various compounds on kinases, such as JAK, ITK, BLK, and VEGFR etc., their characteristics of subtype selectivity, and their influences on the biological activities, including cell growth activity and regulation activity on the signaling pathway, of the cell models.

Example A Enzymatic Activity Detection

Principal Principles

The basic principle of in vitro enzymatic activity assay is based on the difference between the intensities of fluorescence signals generated at different wavelengths (445 nm and 520 nm) from the phosphorylated substrate and non-phosphorylated substrate, in which the specific fluorescence-labeled substrate is phosphorylated by the kinase. When different test compounds are added, the inhibition of kinase activity is represented as the different degrees of substrate phosphorylation, and thus as the different intensities of fluorescence signal, based on which the inhibitory activity of the compound on the kinase can be calculated. Basic detection principle is illustrated in FIG. 1.

In an enzymatic inhibitory activity detection, GST-labeled human recombinant JAK kinases, including JAK1/PV4774, JAK2/PV4210, JAK3/PV3855, TYK2/PV4790 and their corresponding specific substrates, including Tyr6 (Z'-LYTE® Kinase Assay Kit-Tyrosine 6 Peptide, JAK1/PV4122), Tyr4 (Z'-LYTE® Kinase Assay Kit-Tyrosine 4 Peptide, JAK2/PV3193), Tyr4 (Z'-LYTE® Kinase Assay Kit-Tyrosine 4 Peptide, JAK3/PV3193), Tyr3 (Z'-LYTE® Kinase Assay Kit-Tyrosine 4 Peptide, TYK2/PV3192) are used. In all tests, development reagent A (PV3297) was used as the test agent. All materials mentioned above were purchased from Invitrogen.

Principal Procedures

The test is carried out according to the manufacture's instruction (Invitrogen). Specific procedure is as follows:

(1) Preparation: kinase reaction buffer (working solution) is prepared according to the instruction; a concentration gradient of the test compound is prepared by dilution using the kinase reaction buffer (the highest compound concentration is 10 μM for JAK1, JAK2, and TYK2 detection, and 1 μM for JAK3 detection, respectively).

(2) 10 μl of reaction system, comprising 2.5 μL test compound, 5 μL kinase reaction buffer and 2.5 μL ATP solution (provided by the kit), is mixed and reaction is performed at room temperature for 1 h.

(3) Controls, including a solvent control without the test compound, a negative control without ATP and a positive control with the phosphorylated substrate, are tested together with the detection. All tests are carried out in triplicate.

(4) After the enzymatic reaction, 5 μL pre-formulated development buffer is added, and reaction is performed at room temperature for 1 h. Subsequently, the reaction is terminated by adding 5 μL stop buffer.

(5) The fluorescence signal in each well is detected by an Ascent Fluoroskan FL reader (Thermo Labsystems) at an excitation wavelength of 400 nm, and emission wavelengths of 445 nm and 520 nm. The proportion of substrate phosphorylation is obtained by reference to the fluorescence signal intensity C445/F520.

(6) The enzymatic inhibitory rate of the test compound can be calculated based on the following equation: Inhibitory rate (%)=1−the proportion of substrate phosphorylation in the detection well/the proportion of substrate phosphorylation in the solvent control well. The half-inhibitory concentration ($IC_{50}$) can be calculated using an $IC_{50}$ calculator based on the inhibitory rates of phosphorylation for the test compounds at different concentration gradients.

Based on the above method, the compounds described herein are enzymatically evaluated in vitro for JAKs (the concentration of the test compound is 30 nM for JAK3 and JAK2 test, and 300 nM for JAK1 test) using Xeljanz (tofacitinib citrate) as the positive control. Data are summarized in Table 2.

TABLE 2

Enzymatic data of the representative compounds in the present invention for JAKs inhibition

| Example | JAK3($RV^a$) % inhibitory rate @30 nM | JAK1($RV^a$) % inhibitory rate @300 nM | JAK2($RV^a$) % inhibitory rate @30 nM |
|---|---|---|---|
| 7 | 63(0.84) | 56(0.58) | 5(0.08) |
| 13 | 79(0.96) | 35(0.40) | 0 |
| 17 | 84(0.97) | 79(0.93) | 1(0.03) |
| 19 | 59(0.68) | 39(0.46) | 0 |
| 21 | 71(0.82) | 59(0.69) | 2(0.07) |
| 22 | 75(0.82) | 18(0.33) | 0 |
| 23 | 81(0.88) | 19(0.35) | 0 |
| 27 | 35(0.59) | 42(0.45) | ND |
| 28 | 81(0.85) | 34(0.40) | 2(0.03) |
| 32 | 89(0.94) | 49(0.57) | 2(0.03) |
| 36 | 104(0.53) | 42(0.25) | 0 |
| 40 | 89(0.46) | 4(0.02) | 0 |
| 44 | 113(0.58) | 58(0.34) | 0 |
| 48 | 109(0.56) | 0 | 0 |
| 52 | 105(0.54) | 14(0.08) | 0 |
| 56 | 116(0.59) | 9(0.05) | 0 |
| 58 | 107(0.79) | 1(0.01) | 0 |
| 60 | 106(0.79) | 0 | 0 |
| 64 | 105(0.78) | 13(0.13) | 0 |
| 68 | 103(0.76) | 15(0.15) | 0 |
| 71 | 95(0.70) | 7(0.70) | 1(0.01) |
| 75 | 121(0.90) | 14(0.14) | 0 |
| 79 | 80(0.96) | 19(0.22) | 0 |
| 83 | 76(0.92) | 36(0.42) | 2(0.04) |
| 87 | 82(0.99) | 43(0.51) | 0 |
| 91 | 82(0.99) | 20(0.24) | 0 |
| 95 | 84(1.01) | 45(0.53) | 0 |
| 103 | 86(1.04) | 74(0.87) | 0 |
| 107 | 84(1.01) | 67(0.79) | 0 |
| 111 | 82(0.99) | 16(0.19) | 0 |
| 115 | 81(0.98) | 42(0.49) | 0 |
| 123 | 79(0.95) | 0 | 0 |

$^a$RV = ratio between the inhibitory rate of the test compound and that of Xeljanz; ND (No data)

As indicated by the above data in the table, the compounds of the invention have selective JAK3 and/or JAK1 kinase inhibitory activity, as compared to the positive control.

A proportion of the compounds of the present invention are subjected to kinase profile screening (KinaseProfiler™)) and enzymatic inhibitory activity ($IC_{50}$Profiler™)) assay by entrusting Eurofins company (http://www.eurofins.com). Besides the kinases in the JAK family, the kinases that have been screened for their activity also include most Group 3F and Group 4 kinases (ITK, BLK, TBK1, VEGFRs, ERBBs, etc.), and blood system related kinases (Zhang J. et al. 2009, *Nat. Rev. Cancer.*, 9: 28-39). The concentration of the test compound for kinase profile screening is 1 μM, and a gradient of 9 semilog concentration gradients are used to determine $IC_{50}$. Detection is carried out according to standard procedure of Eurofins Company. Briefly, according to the requirements of different kinase reactions, 0.2 μL test compound (50 μM, dissolved in dimethyl sulfoxide (DMSO)) is added to reaction buffer containing specific kinase (the buffer system containing 20 mM MOPS, 1 mM EDTA, 0.01% Brij-35, 5% Glycerol, 0.1% β-mercaptoethanol, 1 mg/mL BSA, or 50 mM TRIS, 0.1 mM EGTA, 0.1 mM $Na_3VO_4$, 0.1% β-mercaptoethanol, 1 mg/mL BSA, based on the type of kinase used). Subsequently, a kinase specific substrate at a final concentration of 50 μM (specific substrate used for specific kinase), 10 mM Mg Acetate and isotope-labeled γ-$^{33}$P ATP (radio-activity of about 500 cpm/pmol) are sequentially added to a total volume of 10 μL for the reaction system. After incubation at room temperature for 40 min, the reaction is terminated by adding 3% phosphoric acid solution. The mixture is then transferred to a filter-type low temperature spray dryer (P30 filtermat), and washed by 75 mM phosphoric acid solution for 3 times and by methanol once. After drying, radio-activity is detected. For specific procedure, see the standard procedure provided by Eurofins Company: http://www.eurofins.com/media/9724077/kinaseprofiler_assay_protocol_guide_eurofins_v64.pdf). Data are summarized in the table below (Table 3).

TABLE 3

$IC_{50}$ of the representative compounds of the invention for inhibition on JAKs, ITK, BLK, TBK1 and VEGFR (nM)

| | $IC_{50}$ (nM) | | | | | | | | |
|---|---|---|---|---|---|---|---|---|---|
| Example | JAK3 | JAK1 | JAK2 | TYK2 | ITK | BLK | TBK1 | Flt1 | Flt4 |
| 7 | 11 | 105 | 1404 | >10,000 | 319 | 286 | 162 | 698 | 107 |
| 22 | 21 | 279 | >10,000 | >10,000 | >10,000 | 1658 | >10,000 | >10,000 | >10,000 |
| 23 | 11 | 173 | 1915 | ND | >10,000 | 855 | 664 | 1228 | 42 |

ND (No data)

As indicated by the data in the above table, (1) some compounds of the invention have selective JAK3 and/or JAK1 kinase inhibitory activity. (2) Some compounds of the invention have inhibitory activity on a part of kinases in ITK, BLK, TBK1 and VEGFR family.

Example B Cell Growth Activity Assay

As described above, the expression of JAK kinase is distributed in a specific manner, and besides in the cells of immune system, it is also expressed in some other types of cells. JAK3 is mainly expressed in T cells, while other subtypes are widely distributed. JAK kinase potentially influences the growth activity of the target cell by mediating various cytokine signals. The inhibitors of JAK kinases may have different effects on the growth of model cells by inhibiting different subtypes of JAKs.

MTS assay is a routine method for cell toxicity detection. The basic principle is based on the capacity of dehydrogenase in the mitochondria of living cells to reduce a novel yellow formazan compound MTS to formazan, so that the amount of living cells is proportional to the amount of formazan product by detecting the absorbance at 490 nm (OD), thereby speculating the amount of living cells according to the OD value, and understanding the capacity of the test compound to inhibit the growth of cells or to kill the cells.

In this experiment, the effect of the compounds of the invention on the cell growth activity is evaluated by MTS assay using different types of cell models, so as to further understand their intracellular activities.
(1) CTLL-2 Cell Model
Principal Principles The activity of JAKs has significant effect on the growth of immune cells. For activated proliferative T cells, their growth depends on the activity of the cell growth factor receptor IL-2 and its downstream kinase JAK1 and JAK3.

In this experiment, mouse T-cell line CTLL-2 was used. The proliferation and growth of this cell line strongly depend on IL-2, and it is commonly used to evaluate the active titer of exogenous IL-2. By inhibiting the activity of kinase JAK1/3, the proliferation of CTLL-2 can be inhibited under in vitro culture. The activation and proliferation of T-cell is also important pathological characteristics for various immunological diseases. Thus, this model is also pathologically related.

By comparing the change of absorbance generated by the cells treated by the test compounds using MTS assay, the growth inhibitory activity of the test compounds on the model cells can be realized, and thereby potential inhibitory activity of the compounds on JAK1/3 pathway can be evaluated.
Principal Procedures MTS is performed according to routine procedure in a 96-well plate.

The model cells are inoculated into each well of the 96-well plate at an appropriate concentration (about 20,000 cells/well). After 24 h, the test compounds are added at different concentration gradients (the highest concentration of 10 μM). A solvent control (DMSO) and a negative control are also performed at the same time. Each experiment is repeated for 3 times. The cells are detected after cultured for another 24 h.

CTLL-2 is a suspended cell. After incubation, 20 μL pre-formulated mixture of MTS and PMS (in a ratio of 20:1) is directly added to each well. After incubation at 37° C. for 2 h, it is then detected by a microplate reader (490 nm).

The effect of the test compound on cell growth is calculated by comparing the change of OD values between the test well and the solvent control well, after subtracting the background of the negative control. For the test compounds at different concentration gradients, the inhibitory rates on the growth of model cells and their half-growth inhibitory concentrations ($GI_{50}$) are each calculated.
(2) HeLa and HUVEC Cell Model
Principal Principles HeLa cell is a human cervical cancer cell line, and belongs to epithelial tumor cell line; HUVEC is a human umbilical vein endothelial cell, and belongs to primary endothelial cell; both types of cells express all subtypes except for JAK3.

The change of JAK kinase activity has no significant influence on other cell types except for the immune cells, and both cell models mentioned above are mainly used to evaluate whether there are any other kinase targets besides JAK kinases or there are nonselective cell toxicities.

In this experiment, a cultured cell model is incubated with the test compounds at different concentrations for a specific duration. The effect of the treatment by the test compound on the growth of cells is detected using MTS assay.
Principal Procedures MTS is performed according to routine procedure in a 96-well plate.

The model cells are inoculated into each well of the 96-well plate at an appropriate concentration (about 5000 cells/well). After 24 h, the test compounds are added at different concentration gradients (the highest final concentration is 40 μM). A solvent control (DMSO) and a negative control are also performed at the same time. Each experiment is repeated for 3 times. The cells are detected after cultured for another 72 h.

After all culture medium is aspirated out of the well, 100 μL fresh medium and 20 μL pre-formulated mixture of MTS and PMS (in a ratio of 20:1) are added to each well. After incubation at 37° C. for 2 h, it is then detected by a microplate reader (490 nm).

The cell growth inhibitory rate and $GI_{50}$ of the test compound are calculated as above.

Based on the above method, cytological evaluation is performed to the compounds described herein (for the detection of CTLL-2 cell, the concentration of the test compound is 300 nM; for the detection of HeLa and HUVEC cell, the concentration of the test compound is 10 nM). Data are summarized in the table below (Table 4).

TABLE 4

The growth rates of different cell strains treated by the representative compounds of the invention

| Example | CTLL-2 % growth rate @300 nM | HeLa % growth rate @10 μM | HUVEC % growth rate @10 μM |
| --- | --- | --- | --- |
| 7 | 10 | 98 | 94 |
| 13 | 63 | 1 | ND |
| 17 | 20 | 1 | 1 |
| 19 | 67 | 108 | 136 |
| 21 | 57 | 94 | 102 |
| 22 | 7 | 78 | 116 |
| 23 | 4 | 96 | 112 |
| 27 | 85 | 30 | 6 |
| 28 | 77 | 81 | 98 |
| 32 | 16 | 68 | 72 |
| 36 | 32 | 38 | ND |
| 40 | 39 | 82 | ND |
| 44 | 29 | 39 | ND |

TABLE 4-continued

The growth rates of different cell strains treated by the representative compounds of the invention

| Example | CTLL-2 % growth rate @300 nM | HeLa % growth rate @10 μM | HUVEC % growth rate @10 μM |
|---|---|---|---|
| 48 | 50 | 90 | ND |
| 52 | 29 | 64 | ND |
| 56 | 30 | 60 | ND |
| 58 | 54 | 88 | ND |
| 60 | 79 | 94 | ND |
| 64 | 37 | 78 | ND |
| 68 | 69 | 110 | ND |
| 71 | 70 | 112 | ND |
| 75 | 49 | 102 | ND |
| 79 | 3 | 78 | ND |
| 83 | 4 | 70 | ND |
| 87 | 3 | 22 | ND |
| 91 | 2 | 40 | ND |
| 95 | 3 | 3 | ND |
| 103 | 3 | 55 | ND |
| 107 | 2 | 59 | ND |
| 111 | 3 | 67 | ND |
| 115 | 3 | 71 | ND |
| 123 | 5 | 5 | ND |

ND (No data)

As indicated by the data in the above table, a portion of the compounds of the invention have specific inhibitory activity on CTLL-2 cell.

Based on cytological experimental methods, the compounds of the invention are subjected to in vitro enzymatic $IC_{50}$ assay and $GI_{50}$ assay of different cell strains, using Xeljanz as the positive control. The results are summarized in the table below (Table 5).

TABLE 5

$GI_{50}$ of the representative compounds of the invention in different cell strains (μM)

| Example | CTLL-2 $GI_{50}$(nM) | HeLa $GI_{50}$(μM) | HUVEC $GI_{50}$(μM) |
|---|---|---|---|
| 7 | 116 | >40 | >40 |
| 22 | 249 | >40 | >40 |
| 23 | 140 | ND | >40 |
| Xeljanz | 67 | >40 | >40 |

ND (No data)

As indicated by the data in the above table, the compounds of the invention have highly selective JAK3 kinase inhibitory activity, and these compounds also have favorable specific inhibitory activity on CTLL-2 cells, as compared to the positive control.

Example C Intracellular Activity Assay

Cytokines, JAK kinases and STAT protein signaling pathway make up a complex network. By activating a homodimer of a specific JAK subtype or a heterodimer of different subtypes, different cytokines promote the phosphorylation of different STAT protein members. In different cell models, signals for the phosphorylation of downstream STAT specifically related to the relevant JAK subtype can be detected using specific stimulation of cytokine, while the activity of the pathway is suppressed by the JAK inhibitors through inhibiting the activity of related kinases, so that intracellular inhibitory activity of the test compounds on different JAK subtypes can be evaluated.

In this experiment, western blot (WB) and flow cytometry are used to evaluate the intracellular activities of the test compounds by comparing the relative levels of the signals of phosphorylated and non-phosphorylated STATs in 5 cell models, including U937, THP-1, CTLL-2, UT-7/EPO and activated human periphery blood cell (hPBC). The primary antibody and secondary antibody used in WB hybridization in this experiment are purchased from Cell Signaling Company (http://www.cellsignal.com). The fluorescence-labeled antibodies used in flow cytometry are purchased from eBiosciences Company (http://www.ebioscience.com).

Principal Principles

U937 is a monocytic cell line. Cytokine IFN γ induces the phosphorylation of downstream STAT5a by activating the heterodimer of JAK1/2, and inhibits the phosphorylation of STAT5a by inhibiting the activity of JAK1/2. On such a basis, the intracellular inhibitory activity of the test compounds on JAK1/2 can be evaluated by detecting the change of the phosphorylation level of STAT5.

THP-1 is a monocytic cell line. Cytokine IL-4 induces the phosphorylation of downstream STAT6 by activating the heterodimer of JAK1/3, and a JAK inhibitor suppresses the phosphorylation of STAT6 by suppressing the activity of JAK1/3. The intracellular inhibitory activity of the compounds on JAK1/3 can be evaluated by detecting the change of the phosphorylation level of STAT6.

CTLL-2 is a T-cell line, and its proliferation and growth depends on cytokine IL-2. Cytokine IL-2 induces the phosphorylation of downstream STAT5 by activating the heterodimer of JAK1/3, and a JAK inhibitor suppresses the phosphorylation of STAT5 by suppressing the activity of JAK1/3. The intracellular inhibitory activity of the compounds on JAK1/3 can be evaluated by detecting the change of the phosphorylation level of STAT5.

UT-7/EPO is a cell line formed from the marrow of a patient suffering from giant cell leukaemia after cultured with EPO induction, and it has obvious response to cytokine EPO. The signal for EPO is transmitted via the homodimer of JAK2 and induces the phosphorylation of downstream STAT5, while a JAK inhibitor suppresses the phosphorylation of STAT5 by suppressing the activity of JAK2. The intracellular inhibitory activity of the compounds on JAK2 can be evaluated by detecting the change of the phosphorylation level of STAT5.

Cytokine IL-2 dependent proliferation is formed after activation by co-stimulation of human periphery blood cell (hPBC) with CD3 antibody. The growth signal pathway is mediated by the heterodimer of JAK1/3 and induces the phosphorylation of downstream STAT5. The intracellular inhibitory activity of the compounds on JAK1/3 can be evaluated by detecting the change of the phosphorylation level of STAT5.

Principal Procedures

Western Blot (WB)

(1) Treatment by the compound: the experiment is carried out in a 6-well plate. U937 and THP-1 cell is each cultured to appropriate density, into which the test compound is added at different concentrations. After cultured over night (16 h), IFN γ or IL-4 (10 ng/mL) is added correspondingly. The cells are collected by centrifugation 30 min later.

(2) Protein extraction and WB detection: after extraction, the protein content is determined. The protein is transferred to a membrane after PAGE electrophoresis. The WB detection is performed according to a standard procedure. The secondary antibodies used for hybridization include STAT5 (#9363), STAT6 (#9362) and corresponding phosphorylated STAT5 (#9351), STAT6 (#9361). Detection is performed according to the recommended method in the instruction of antibody.

(3) Signal detection: the hybridization signal is detected by X-ray imaging. The grey scale signal obtained by scanning is converted to digital signal, and the signal intensities for both phosphorylated STATs and STATs are each calculated to evaluate the phosphorylation inhibitory activities of the compounds on STATs.

Flow Cytometry (FCS)

(1) Treatment by the compound: the experiment is carried out in a 6-well plate. THP-1, CTLL-2, UT7/EPO and in vitro activated periphery blood cell (hPBC) from volunteers are each cultured to appropriate density, into which the test compound is added at different concentrations. After cultured over night (16 h), IFN γ, IL-4, IL-2 and EPO (10 ng/mL) are added correspondingly. The cells are collected by centrifugation 30 min later.

(2) Cell fixation and fluorescence labeling: the cells are fixed using paraformaldehyde (30 min), and subsequently treated for membrane permeability in chilled methanol (15 min). After washed by PBS buffer, the cells are suspended, into which phosphorylation-resistant STAT5 and STAT6 antibody (Mouse anti-Human p-STAT5 (pY694)-Fluor®488; Mouse anti-Rabbit p-STAT6 (pY641)-Fluor®488) are added in a ratio of 100:1, and incubated in dark for 30 min. After washed by PBS, the cells are prepared into suspension for loading.

(3) Detection by flow cytometry: the detection is carried out using Guava® easyCyte flow cytometer according to the instruction. The median fluorescent intensity (MFI) of a sample is detected using an appropriate cell population. On such a basis, the relative signal intensities are calculated for the phosphorylated STATs treated by the compounds at different concentrations by reference to the signal of the negative (with no factor stimulation) and the positive control (with both factor stimulation and solvent control) in the experiment, so that the $IC_{50}$ of the compound for the inhibitory activity on STATs phosphorylation can be evaluated.

Based on the above experimental methods, the compounds of the invention are selected for WB and flow cytometry, in which a portion of the compounds inhibited STATs phosphorylation in specific cell models with $IC_{50}$ values are as follows. Data are summarized in the table below (Table 6).

TABLE 6

Inhibition of the compounds of the invention on phosphorylation

| Example | IL-4/JAK1 & 3/STAT6 (THP-1) $IC_{50}(\mu M)$ | EPO/JAK2/STAT5a (UT-7) $IC_{50}(\mu M)$ | IL-2/JAK1 & 3/STAT5 (CTLL-2) $IC_{50}(\mu M)$ | IL-2/JAK1 & 3/STAT5 (hPBC) $IC_{50}(\mu M)$ |
|---|---|---|---|---|
| 7 | 1.69 | >3 | 0.08 | 0.16 |
| 22 | ND | >3 | ND | 0.20 |
| 23 | 1.73 | >3 | 0.13 | 0.24 |

ND (No data)

As indicated by the data in the above table, a portion of the compounds of the invention have intracellular selective JAK3 and/or JAK1 inhibitory activity, which is consistent with the result obtained in in vitro enzymatic evaluation.

Example D Effect of the Test Compounds in the Collagen-Induced Arthritis (CIA) Model of Rats Objective: in this test, arthritis is induced by chicken collagen in Wistar rats. After in vivo administration of the compounds of Example 7 and Example 22, the change of the disease index for arthritis in rats is evaluated to determine the therapeutic effect of the test compounds on rat arthritis.

Experimental animals: 36 female Wistar rats were purchased from the animal experiment center, Sun Yat-Sen University (Guangzhou) with the body weight ranging from 180 to 200 g at the beginning of experiment. Four groups (8 rats in each group) were used as the arthritis model, and another group (4 rats) was used as normal control.

Materials: chicken type II collagen and Freund's complete adjuvant were purchased from Beijing Biolead Science and Technology Development Co., Ltd. Positive control: methotrexat (MTX).

Test compounds: the compounds of Example 7 and Example 22.

Preparation method: the test compounds were prepared by adding them to freshly prepared 0.2% CMC-Na+0.1% Tween-80 solution in sterile water to a desired concentration and thoroughly mixing through ultrasound.

Experiment Methods:

CIA model: the chicken collagen was fully emulsified in equal volume of freud's complete adjuvant, and subcutaneously injected at the tail root of the rat on day 0 for sensitization (250 μL/rat). Another injection was performed at the tail root on day 7 for supplementary immunization (100 μL/rat). After arthritis occurred (on about day 13), the rats were randomly divided into 4 groups with 8 rats in each group. Administration started on day 14 after the first immunization, and lasted for 14 days. The limbs of a rat were visually inspected, and the severity of arthritis was scored in a range from 1 to 4: 0=normal; 1=a slight symptom, with signs, such as red and swollen ankle or wrist; 2=moderate red and swollen ankle or wrist; 3=severe red and swollen paw, including toes; 4=severe swollen joint accompanied with dysfunction; the highest score for each rat was 16. The thickness of toes of posterior limbs and the paw volume were measured at the same time.

Medication: the rats were i.g. administered with the compound of Example 7 at a concentration of 40 mg/kg twice/day; or the rats were i.g. administered with the compound of Example 22 at a concentration of 40 mg/kg twice/day. For the positive control, 5 mg/kg MTX was intraperitoneally injected twice a week. The i.g. administration of solvent was used as the negative control. The data obtained 14 days after administration and before administration were compared. The results are listed in the table below (Table 7).

TABLE 7

Efficacy of the test compounds in the collagen-induced arthritis (CIA) model of rats

| Compound | Inhibitory rate for arthritis score % | Inhibitory rate for toe thickness % | Inhibitory rate for paw volume % | Body weight growth rate % |
|---|---|---|---|---|
| Solvent | 0.0 | 0.0 | 0.0 | 100.0 |
| MTX | 73.1 | 70.2 | 43.1 | 95.4 |
| 7 | 75.0 | 74.3 | 63.6 | 102.2 |
| 22 | 25.5 | 13.9 | 24.6 | 102.0 |

Results:

1. As compared to the solvent group, the swelling degree induced by arthritis in the rats were significantly inhibited when the compound of Example 7 (40 mg/kg) was i.g. administered, and the inhibitory rates for all indices were better than those obtained by the positive control methotrexate; certain inhibitory effect was also observed for arthritis in the rats when the compound of Example 22 (40 mg/kg) was i.g. administered.

2. As compared to the solvent group, the body weight of the rats in the methotrexate group decreased, suggesting certain toxicity of methotrexate to the rats. While the body weight gains of the rats in both groups of the test compound of Example 7 and 22 were better than that in the solvent group, demonstrating that both compounds of Example 7 and 22 have no significant toxicity. The efficacy/safety indices of the compound of Example 7 are better than those of the positive control MTX.

The invention claimed is:

1. A compound of general formula (I),

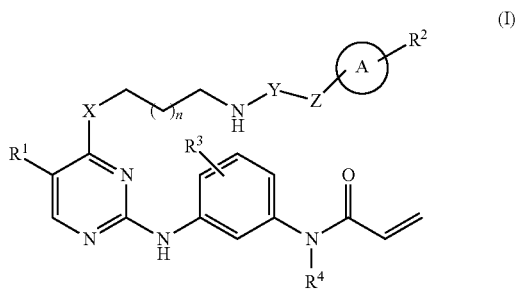

or a pro-drug, stereoisomer, pharmaceutically acceptable salt or hydrate thereof,
wherein,
$R^1$ is halogen or C1-C6 alkyl;
$R^2$ is one or more substituents selected from the group consisting of hydrogen, hydroxy, cyano, halogen, C1-C6 alkyl, C1-C6 alkoxy, C1-C6 haloalkyl, C1-C6 alkylcarbonyl and C1-C6 alkylamino;
$R^3$ is hydrogen or halogen;
$R^4$ is hydrogen or C1-C4 alkyl;
X is NH, O or S;
Y is CO or $S(O)_2$;
Z is a covalent bond, $CH_2$ or $(CH_2)_2$;
n is an integer from 1 to 4; and
Ring A is a benzene ring, pyridine ring or piperidine ring.

2. The compound of general formula (I) according to claim 1, wherein:
$R^1$ is halogen or C1-C6 alkyl;
$R^2$ is one or more substituents selected from the group consisting of hydrogen, hydroxy, cyano, fluoro, methyl, ethyl, methoxyl, difluoromethyl, trifluoromethyl, acetyl and dimethylamino;
$R^3$ is hydrogen or halogen;
$R^4$ is hydrogen or methyl;
X is NH or O;
Y is CO or $S(O)_2$;
Z is a covalent bond, $CH_2$ or $(CH_2)_2$;
n is an integer from 1 to 4; and
Ring A is a benzene ring, pyridine ring or piperidine ring.

3. The compound of general formula (I) according to claim 1, wherein:
$R^1$ is halogen or C1-C6 alkyl;
$R^2$ is one or more substituents selected from the group consisting of hydrogen, hydroxy, cyano, fluoro, methyl, ethyl, methoxyl, difluoromethyl, trifluoromethyl, acetyl and dimethylamino;
$R^3$ is hydrogen or fluoro;
$R^4$ is methyl;
X is NH;
Y is CO;
Z is a covalent bond;
n is an integer from 1 to 4; and
Ring A is a benzene ring, pyridine ring.

4. The compound of general formula (I) according to claim 1, wherein:
$R^1$ is chloro, fluoro or methyl;
$R^2$ is one or more substituents selected from the group consisting of hydrogen, hydroxy, cyano, fluoro, methyl, ethyl, methoxyl, difluoromethyl, trifluoromethyl, acetyl and dimethylamino;
$R^3$ is hydrogen or fluoro;
$R^4$ is methyl;
X is NH;
Y is CO;
Z is a covalent bond;
n is an integer from 1 to 4; and
Ring A is a benzene ring.

5. The compound of general formula (I) according to claim 1, wherein:
$R^1$ is chloro;
$R^2$ is one or more substituents selected from the group consisting of hydrogen, hydroxy, cyano, fluoro, methyl, ethyl, methoxyl, difluoromethyl, trifluoromethyl, acetyl and dimethylamino;
$R^3$ is hydrogen or fluoro;
$R^4$ is methyl;
X is NH;
Y is CO;
Z is a covalent bond;
n is an integer from 1 to 4; and
Ring A is a benzene ring.

6. The compound of general formula (I) according to claim 1, wherein:
$R^1$ is chloro;
$R^2$ is one or more substituents selected from the group consisting of cyano, fluoro and trifluoromethyl;
$R^3$ is hydrogen or fluoro;
$R^4$ is methyl;
X is NH;
Y is CO;
Z is a covalent bond;
n=1; and
Ring A is a benzene ring.

7. The compound of general formula (I) according to claim 1, wherein:
$R^1$ is chloro;
$R^2$ is one or more substituents selected from the group consisting of cyano;
$R^3$ is hydrogen or fluoro;
$R^4$ is methyl;
X is NH;
Y is CO;
Z is a covalent bond;
n=1; and
Ring A is a benzene ring.

8. The compound according to claim 1, wherein the compound is selected from the group consisting of:
N-(3-(5-chloro-2-(4-fluoro-3-(N-methylacrylamido)phenylamino)pyrimidinyl-4-amino)propyl)-4-cyanobenzamide;
N-(3-(2-(3-acrylamido-4-fluoro-phenylamino)-5-chloropyrimidinyl-4-amino)propyl)-4-trifluoromethylbenzamide;
N-(3-(2-(3-acrylamido-4-fluoro-phenylamino)-5-chloropyrimidinyl-4-amino)propyl)-4-fluorobenzamide;

4-fluoro-N-(3-(2-(4-fluoro-3-(N-methylacrylamido)phenylamino)-5-methylpyrimidinyl-4-amino)propyl)benzamide;

N-(3-(2-(4-fluoro-3-(N-methylacrylamido)phenylamino)-5-methylpyrimidinyl-4-amino)propyl)-4-trifluoromethylbenzamide;

N-(3-(5-chloro-2-(4-fluoro-3-(N-methylacrylamido)phenylamino)pyrimidinyl-4-amino)propyl)-4-trifluoromethylbenzamide;

N-(3-(5-chloro-2-(4-fluoro-3-(N-methylacrylamido)phenylamino)pyrimidinyl-4-amino)propyl)-4-fluorobenzamide;

N-(3-(5-chloro-2-(4-fluoro-3-(N-methylacrylamido)phenylamino)pyrimidinyl-4-amino)propyl)-1-methylpiperidinyl-4-formamide;

N-(3-(2-(3-acrylamido-4-fluorophenylamino)-5-chloropyrimidinyl-4-amino)propyl)-4-cyanobenzamide;

N-(3-(5-chloro-2-(4-fluoro-3-(N-methylacrylamido)phenylamino)pyrimidinyl-4-amino)propyl)-4-dimethylaminobenzamide;

N-(3-(5-chloro-2-(4-fluoro-3-(N-methylacrylamido)phenylamino)pyrimidinyl-4-amino)propyl)-2,4,6-trifluorobenzamide;

N-(3-(5-chloro-2-(4-fluoro-3-(N-methylacrylamido)phenylamino)pyrimidinyl-4-amino)propyl)-4-methoxylbenzamide;

N-(3-(5-chloro-2-(4-fluoro-3-(N-methylacrylamido)phenylamino)pyrimidinyl-4-amino)propyl)-6-cyanonicotinamide;

N-(3-(5-chloro-2-(4-fluoro-3-(N-methylacrylamido)phenylamino)pyrimidinyl-4-amino)propyl)-4-hydroxybenzamide;

N-(3-(5-chloro-2-(4-fluoro-3-(N-methylacrylamido)phenylamino)pyrimidinyl-4-amino)propyl)-4-cyano-2-fluorobenzamide;

N-(3-(5-chloro-2-(4-fluoro-3-(N-methylacrylamido)phenylamino)pyrimidinyl-4-amino)propyl)-4-cyano-3-fluorobenzamide;

4-cyano-N-(3-(2-(4-fluoro-3-(N-methylacrylamido)phenylamino)-5-methylpyrimidinyl-4-amino)propyl)-benzamide;

4-cyano-N-(3-(5-fluoro-2-(4-fluoro-3-(N-methylacrylamido)phenylamino)pyrimidinyl-4-amino)propyl)benzamide;

N-(5-(5-chloro-4-(3-(2-(4-cyanophenyl)acetamino)propylamino)pyrimidinyl-2-amido)-2-fluorophenyl)-N-methylacryloyl;

N-(5-(5-chloro-4-(3-(4-cyanophenylsulfonamino)propylamino)pyrimidinyl-2-amido)-2-fluorophenyl)-N-methylacryloyl;

N-(3-(5-chloro-2-(4-fluoro-3-(N-methylacrylamido)phenylamino)pyrimidinyl-4-oxo)propyl)-4-cyanobenzamide;

N-(3-(5-chloro-2-(4-fluoro-3-(N-methylacrylamido)phenylamino)pyrimidinyl-4-amino)propyl)-isonicotinamide;

N-(3-(5-chloro-2-(4-fluoro-3-(N-methylacrylamido)phenylamino)pyrimidinyl-4-amino)propyl)-4-ethylbenzamide;

N-(3-(5-chloro-2-(4-fluoro-3-(N-methylacrylamido)phenylamino)pyrimidinyl-4-amino)propyl)-4-methylbenzamide;

N-(3-(5-chloro-2-(4-fluoro-3-(N-methylacrylamido)phenylamino)pyrimidinyl-4-amino)propyl)benzamide;

N-(3-(5-chloro-2-(4-fluoro-3-(N-methylacrylamido)phenylamino)pyrimidinyl-4-amino)propyl)-3-trifluoromethylbenzamide;

N-(3-(5-chloro-2-(4-fluoro-3-(N-methylacrylamido)phenylamino)pyrimidinyl-4-amino)propyl)-3-cyanobenzamide;

N-(3-(5-chloro-2-(4-fluoro-3-(N-methylacrylamido)phenylamino)pyrimidinyl-4-amino)propyl)-3-fluoro-4-trifluoromethylbenzamide;

N-(3-(5-chloro-2-(4-fluoro-3-(N-methylacrylamido)phenylamino)pyrimidinyl-4-amino)propyl)-2,3,4,5-tetrafluorobenzamide;

4-acetyl-N-(3-(5-chloro-2-(4-fluoro-3-(N-methylacrylamido)phenylamino)pyrimidinyl-4-amino)propyl)benzamide;

N-(3-(5-chloro-2-(4-fluoro-3-(N-methylacrylamido)phenylamino)pyrimidinyl-4-amino)propyl)-4-difluoromethylbenzamide; and N-(6-(5-chloro-2-(4-fluoro-3-(N-methylacrylamido)phenylamino)pyrimidinyl-4-amino)hexyl)-4-cyanobenzamide.

9. A method for preparing the compound of general formula (I) according to claim 1, comprising reacting a compound of general formula (IV)

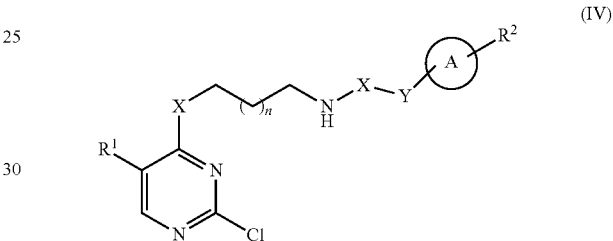

with a compound of general formula (V)

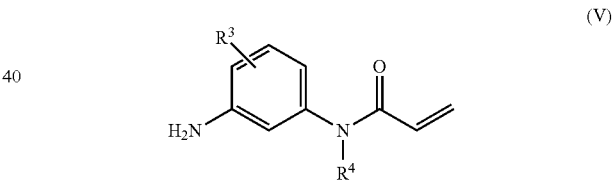

under organic solvent and a catalyst to form the compound of general formula (I), wherein $R^1$ is halogen or C1-C6 alkyl;

$R^2$ is one or more substituents selected from the group consisting of hydrogen, hydroxy, cyano, halo, C1-C6 alkyl, C1-C6 alkoxy, C1-C6 haloalkyl, C1-C6 alkylcarbonyl and C1-C6 alkyl amino;

$R^3$ is hydrogen or halogen;

$R^4$ is hydrogen or C1-C4 alkyl;

X is NH, O or S;

Y is CO or $S(O)_2$;

Z is a covalent bond, $CH_2$ or $(CH_2)_2$;

n is an integer from 1 to 4; and ring A is a benzene ring, pyridine ring or piperidine ring.

10. The preparation method according to claim 9, wherein the catalyst is selected from the group consisting of trifluoroacetic acid, hydrochloric acid and methanesulfonic acid.

11. The preparation method according to claim 9, wherein the organic solvent is selected from the group consisting of isopropanol and n-butanol.

12. A method for preparing a compound of general formula (IV),

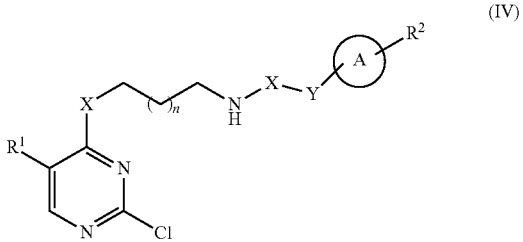

comprising reacting a compound of general formula (III)

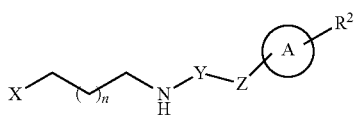

with a compound of general formula (II)

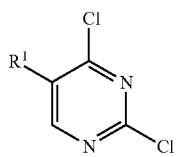

under organic solvent and an alkali to form the compound of general formula (IV), wherein
$R^1$ is halogen or C1-C6 alkyl;
$R^2$ is one or more substituents selected from the group consisting of hydrogen, hydroxy, cyano, halo, C1-C6 alkyl, C1-C6 alkoxy, C1-C6 haloalkyl, C1-C6 alkylcarbonyl and C1-C6 alkyl amino;
X is NH or O;
Y is CO or $S(O)_2$;
Z is a covalent bond, $CH_2$ or $(CH_2)_2$;
n is an integer from 1 to 4; and
ring A is a benzene ring, pyridine ring or piperidine ring.

13. The preparation method according to claim 12, wherein the alkali is selected from the group consisting of triethylamine and diisopropylethylamine.

14. The preparation method according to claim 9, wherein the organic solvent is selected from the group consisting of ethanol, methanol and n-butanol.

15. A pharmaceutical composition comprising the compound of general formula (I) according to claim 1 as the active ingredient and a pharmaceutically acceptable carrier, adjuvant or diluent.

16. The pharmaceutical composition according to claim 15, which is in the form of tablet, capsule, powder, syrup, liquor, suspension, injection or ointment.

17. A method of treating a disease related to abnormal activities of JAK3 and/or JAK1 kinases in a human patient, comprising administering the human patient the compound according to claim 1, wherein the disease related to abnormal activities of JAK3 and/or JAK1 kinases is selected from the group consisting of autoimmune diseases, cancers, bone resorption diseases graft-versus-host diseases.

18. A method of treating a disease related to abnormal activities of JAK3 and/or JAK1 kinases in a human patient, comprising administering the human patient the compound according to claim 1, wherein the disease related to abnormal activities of JAK3 and/or JAK1 kinases is selected from the group consisting of psoriasis, systemic lupus erythematosus, multiple sclerosis, type I diabetes, leukaemia, and lymphoma.

19. A method of treating a disease related to abnormal activities of JAK3 and/or JAK1 kinases in a human patient, comprising administering the human patient the pharmaceutical composition according to claim 15, wherein the disease related to abnormal activities of JAK3 and/or JAK1 kinases is selected from the group consisting of autoimmune diseases, cancers, bone resorption diseases and graft-versus-host diseases.

20. A method of treating a disease related to abnormal activities of JAK3 and/or JAK1 kinases in a human patient, comprising administering the human patient the pharmaceutical composition according to claim 15, wherein the disease related to abnormal activities of JAK3 and/or JAK1 kinases is selected from the group consisting of rheumatoid arthritis, psoriasis, systemic lupus erythematosus, multiple sclerosis, type I diabetes, leukaemia, and lymphoma.

21. The pharmaceutical composition according to claim 16, wherein the formulation thereof has a unit dosage ranging from 0.0001 to 200 mg.

* * * * *